US008889855B2

(12) United States Patent (10) Patent No.: US 8,889,855 B2
Deng (45) Date of Patent: Nov. 18, 2014

(54) PREPARATION OF MAYTANSINOID ESTERS

(71) Applicant: Bio-Thera Solutions, Ltd., Co., Guangzhou (CN)

(72) Inventor: Xiaobin Deng, Guangzhou (CN)

(73) Assignee: Bio-Thera Solutions Ltd., Co., Guangzhou Science City (CN)

( * ) Notice: Subject to any disclaimer, the term of this patent is extended or adjusted under 35 U.S.C. 154(b) by 0 days.

(21) Appl. No.: 13/836,469

(22) Filed: Mar. 15, 2013

(65) Prior Publication Data

US 2014/0179917 A1 Jun. 26, 2014

(30) Foreign Application Priority Data

Dec. 21, 2012 (CN) .......................... 2012 1 0564206
Mar. 14, 2013 (CN) .......................... 2013 1 0081867

(51) Int. Cl.
  *C07D 491/12* (2006.01)
  *C07D 498/06* (2006.01)
  *C07D 498/18* (2006.01)
  *C07D 498/08* (2006.01)

(52) U.S. Cl.
  CPC ............ *C07D 498/18* (2013.01); *C07D 498/08* (2013.01)
  USPC ....................................................... 540/456

(58) Field of Classification Search
  USPC ....................................................... 540/456
  See application file for complete search history.

(56) References Cited

U.S. PATENT DOCUMENTS

| 3,896,111 | A | 7/1975 | Kupchan et al. |
| 4,137,230 | A | 1/1979 | Hashimoto et al. |
| 4,256,746 | A | 3/1981 | Miyashita et al. |
| 4,260,608 | A | 4/1981 | Miyashita et al. |
| 5,208,020 | A | 5/1993 | Chari et al. |
| 5,416,064 | A | 5/1995 | Chari et al. |
| 6,333,410 | B1 | 12/2001 | Chari et al. |
| 2006/0167245 | A1 | 7/2006 | Widdison et al. |
| 2012/0121615 | A1 | 5/2012 | Flygare et al. |

FOREIGN PATENT DOCUMENTS

EP 0021173 A1 1/1981

OTHER PUBLICATIONS

Cassady, John M., et al., Recent Developments in the Maytansinoid Antitumor Agents, Chem. Pharm. Bull., Jan. 2004, pp. 1-26, vol. 52, No. 1, Pharmaceutical Society of Japan.
Desmyter, Aline, et al., Crystal structure of a camel single-domain VH antibody fragment in complex with lysozyme, Nature Structural Biology, Sep. 1996, pp. 803-811, vol. 3, No. 9, Nature Publishing Group, http://www.nature.com/nsmb.
Greenberg, A.S., et al., A new antigen receptor gene family that undergoes rearrangement and extensive somatic diversification in sharks, Nature, Mar. 9, 1995, pp. 168-173, vol. 374.
Greene, T.W., et al., Protecting Groups in Organic Synthesis, 1999, Third Edition, Wiley, New York.
Hudziak, R.M., et al.,p185HER2 Monoclonal Antibody Has Antiproliferative Effects In Vitro and Sensitizes Human Breast Tumor Cells to Tumor Necrosis Factor, Molecular and Cellular Biology, Mar. 1989, pp. 1165-1172, vol. 9, No. 3, American Society for Microbiology.
Ishiyama, Munetaka, et al., A Combined Assay of Cell Viability and in Vitro Cytotoxicity with a Highly Water-Soluble Tetrazolium Salt, Neutral Red and Crystal Violet, Biol. Pharm. Bull. 1996, vol. 19, No. 11, Pharmaceutical Society of Japan.
Issel, B., et al., Maytansine, 5 Cancer Treatment Reviews, 1978, pp. 199-207.
Kawai, Akiyoshi, et al., Chemical Modification of Ansamitocins. III. Synthesis and Biological Effects of 3-Acyl Esters of Maytansinol, Chem. Pharm., Bull., 1984, Chem. Pharm. Bull., pp. 3441-3451, vol. 32, No. 9.
Kupchan, S.M., et al., Maytansine, a novel antileukemic ansa macrolide from Maytenus ovatus, J. Am. Chem. Soc., 1972, pp. 1354-1356, vol. 94, No. 4.
Mossner, Ekkehard, et al., Increasing the efficacy of CD290 antibody therapy through the engineering of a new type II anti-CD20 antibody with enhanced direct and immune effector cell-mediated B-cell cytotoxicity, Blood, Jun. 3, 2010, pp. 4393-4402, vol. 115, No. 22.
Nisonoff, A., et al., Separation of Univalent Fragments from the Bivalent Rabbit Antibody Molecule by Reduction of Disulfide Bonds, 1960, pp. 230-244, Archives of Biochemistry and Biophysics 89.
O'Keefe, Donald O., et al., Characterization of a Transferrin-Diphtheria Toxin Conjugate, The Journal of Biological Chemistry, 1985, pp. 932-937, vol. 260, No. 2, American Society of Biological Chemists, Inc.
Parham, Peter, On the Fragmentation of Monoclonal IgG1, IgG2a, and IgG2b from BALB/c Mice, The Journal of Immunology, Dec. 1983, pp. 2895-2902, vol. 131, No. 6, American Association of Immunologists.
Remillard, Stephen et al., Antimitotic Activity of the Potent Tumor Inhibitor Maytansine, Science, Sep. 1975, pp. 1002-1005, vol. 189,Dept. of Biology, University of Virginia.
Smith, C.R. Jr., et al., Alkaloids, 1984, ed. Pelletier, S.W., 2, pp. 149-204, Wiley, NY.
Spring, Susan B., et al., The Journal of Immunology, Aug. 1974, pp. 470-478, vol. 113, No. 2, The Williams & Wilkins Co.

(Continued)

*Primary Examiner* — Bruck Kifle
(74) *Attorney, Agent, or Firm* — Buchanan Ingersoll & Rooney PC

(57) ABSTRACT

Provided are efficient methods for direct coupling of a maytansinoid with a carboxylic acid to prepare a maytansinoid C-3 ester in high yield using a rare earth metal-based or trifluoromethanesulfonate-based Lewis acid catalyst and a base together with a coupling reagent. Also provided are compositions used in such methods.

44 Claims, No Drawings

(56) References Cited

OTHER PUBLICATIONS

Stanfield, Robyn L., et al., Crystal Structure of a Shark Single-Domain Antibody V Region in Complex with Lysozyme, *Science*, Sep. 17, 2004, pp. 1770-1773, vol. 305, www.sciencemag.org.

Stewart, Ross, et al., A variant human IgG1-Fc mediates improved ADCC, Protein Engineering, Design & Selection, May 18, 2011, pp. 671-678, vol. 24, No. 9, Oxford University Press, doi:10.1093/protein/gzr015.

Widdison, Wayne C., et al., Semisynthetic Maytansine Analogues for the Targeted Treatment of Cancer, J. Med. Chem., J. Med. Chem., 2006, pp. 4392-4408, vol. 49, American Chemical Society.

Wolpert-Defilippes, Mary K., et al., Initial Studies on Maytansine-Induced Metaphase Arrest in L1210 Murine Leukemia Cells, Biochemical Pharmacology, 1975, pp. 1735-1738, vol. 24, Pergamon Press, Great Britain.

Wood, Clive R., et al., High Level Synthesis of Immunoglobulins in Chinese Hamster Ovary Cells, Journal of Immunology, Nov. 1, 1990, pp. 3011-3016, vol. 145, No. 9, American Assn. of Immunologists.

Yu, Tin-Wein, et al., The biosynthetic gene cluster of the maytansinoid antitumor agent ansamitocin from Actinosynnema pretiosum, PNAS, Jun. 11, 2002, pp. 7968-7973, vol. 99, No. 12, www.pnas.org/cgi/doi/10.1073/pnas.092697199.

PREPARATION OF MAYTANSINOID ESTERS

CROSS REFERENCE TO RELATED APPLICATIONS

This application claims priority under 35 U.S.C. §119 to CN 201210564206.8, filed on Dec. 21, 2012 and CN 201310081867.X, filed on Mar. 14, 2013, the contents of which is hereby expressly incorporated by reference in their entirety for all purposes and are assigned to the assignee hereof.

FIELD

The present invention relates to preparation of maytansinoid esters by direct coupling of maytansinol with a carboxylic acid. In one embodiment, the invention relates to a catalytic method for preparation of maytansinoid C-3 chiral amino acid esters by direct coupling of maytansinol with a chiral amino acid derivative. The maytansinoid esters are useful in the preparation of maytansinoid conjugates useful in treating cancers.

BACKGROUND

Maytansinoids are potent antimitotic agents that interfere with the formation of microtubules through the inhibition of the assembly of tubulin (Remillard, et al. (1975) Science 189: 1002-1005). It has been shown that maytansinoids are 100 to 1000 fold more cytotoxic than conventional cancer chemotherapeutic agents like methotrexate, daunorubicin, and vincristine (U.S. Pat. No. 3,896,111). However, use of maytansinoids in human clinical trials was intolerable because they displayed an inadequate therapeutic window in vivo. A much wider therapeutic window can be obtained when maytansinoids are conjugated with antibodies that target specific cells to form antibody-drug conjugates (ADCs). Due to their high potency, maytansinoids are ideal candidates as payloads of ADCs. It was found that C-3 esters with derivatives of N-methyl-L-alanine were much more cytotoxic than the corresponding esters of simple carboxylic acid and 100 times more cytotoxic than their epimers corresponding to N-methyl-D-alanine (U.S. Pat. Nos. 4,137,230; 4,260,608; Kawai, et al. (1984) Chem. Pharm. Bull. 32: 3441-3451; Widdison, et al. (2006) J. Med. Chem. 49: 4392-4408).

The current method for direct coupling of maytansinol with a carboxylic acid by DCC/$ZnCl_2$ has the drawbacks of low yields and poor reproducibility. Further, when chiral amino acid derivatives such as N-methyl-L-alanine derivatives are coupled with maytansinol, complete epimerization of side chain chiral center occurred giving L and D-aminoacyl ester in a 1:1 ratio. This greatly reduced the yield of the desired product in the total coupled products. Furthermore, tedious chromatographic separation (both column and HPLC) of the desired product from the unwanted diastereomer was needed. (U.S. Pat. Nos. 4,137,230; 4,260,608; 5,208,020; 5,416,064; 6,333,410; Kawai, et al. (1984) Chem. Pharm. Bull. 32: 3441-3451; Widdison, et al. (2006) J. Med. Chem. 49: 4392-4408).

Another method for preparation of maytansinol C-3 ester is through forming an anion of maytansinol with a suitable base such as metal hexamethyldisilazide (metal=Li, Na, K, Zn) followed by reacting the anion with an activated carboxy compounds such as anhydride and acyl fluoride. Additional reaction steps are needed for conversion of carboxylic acid to its anhydride or acyl fluoride, which are typically unstable intermediates. Because of high water and air sensitivity of metal hexamethyldisilazide, strict water free and oxygen free conditions under low temperatures are required. Furthermore, large excess of expensive zinc hexamethyldisilazide is required to generate the coupling product in a good yield. While US Patent Application Publication No. 2006/0167245 asserts that little epimerization of chiral center occurred, no reaction yield was given.

Because the starting material maytansinol is very expensive and the existing methods for coupling maytansinol with carboxylic acid resulted in low yield and/or epimerization of side chain chiral center, a method for preparation of maytansinoid esters with high yield and high diastereoselectivity by direct coupling of maytansinol with a carboxylic acid, especially a chiral amino acid such as N-methyl-L-alanine derivative, is greatly needed to speed up the research and development process of cell binding agent maytansinoid conjugates for target cancer therapy.

SUMMARY

The present invention provides an efficient method for esterification of a maytansinoid with a carboxylic acid to prepare a maytansinoid C-3 ester in high yield using a rare earth metal-based or trifluoromethanesulfonate-based Lewis acid catalyst and a base together with a coupling reagent.

In some embodiments, the present invention provides a method for stereoselective C-3 esterification of a maytansinoid with a chiral amino acid derivative, such as N-methyl-L-alanine, L-cysteine and L-methionine derivatives, to prepare a maytansinoid C-3 ester, such as maytansinoid C-3 N-methyl-L-alanine, L-cysteine or L-methionine ester, in high yield and high diastereo selectivity, which are useful in the preparation of cell-binding agent maytansinoid conjugates.

In some embodiments, provided is a method of preparing a compound of Formula I or a salt thereof:

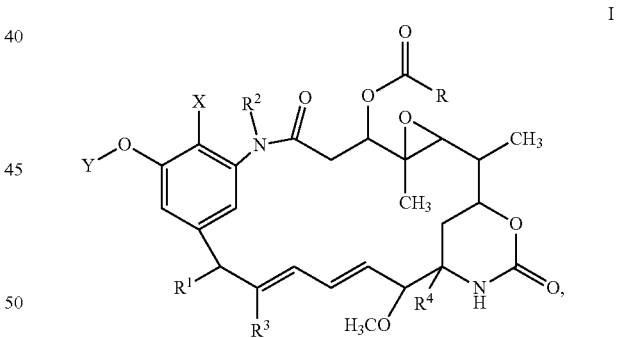

comprising contacting a compound of Formula I-A:

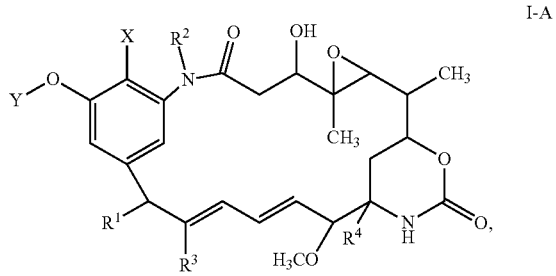

with a carboxylic acid of the formula R—COOH in the presence of a coupling reagent, a rare earth metal-based or trifluoromethanesulfonate-based Lewis acid catalyst and a base to form the compound of Formula I, or a salt thereof;
wherein
X is hydrogen or halo;
Y is selected from the group consisting of hydrogen, $C_1$-$C_6$ alkyl, $C_3$-$C_6$ cycloalkyl, benzyl, and —C(=O)$R^5$;
$R^1$ is hydrogen, —OH or —O$R^{17}$;
$R^2$ is hydrogen or $C_1$-$C_6$ alkyl;
$R^3$ is methyl, —CH$_2$OH or CH$_2$O$R^{17}$
$R^4$ is —OH, —O$R^{17}$ or —SH;
$R^5$ is $C_1$-$C_6$ alkyl or benzyl;
$R^{17}$ is a hydroxy protecting group;
R is selected from the group consisting of alkyl, aryl, cycloalkyl, cycloalkenyl, heteroaryl, and heterocyclic, wherein the alkyl, aryl, cycloalkyl, cycloalkenyl, heteroaryl, or heterocyclic is optionally substituted with one to three $R^{10}$, or is

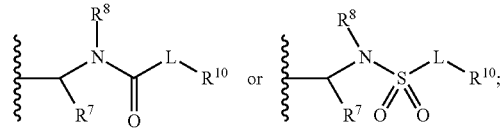

L is selected from optionally substituted $C_1$-$C_{20}$ alkylene, $C_3$-$C_8$ cycloalkylene, optionally substituted $C_1$-$C_{20}$ alkylene wherein one or more of the —CH$_2$— group is independently replaced with $C_3$-$C_8$ cycloalkylene, —O—, —S—, —N$R^8$—, —C(O)—, —C(=O)N$R^8$—, —N$R^8$C(=O)—, —SO$_2$N$R^8$—, or —N$R^8$SO$_2$—;
substituted $C_1$-$C_{20}$ alkylene is $C_1$-$C_{20}$ alkylene substituted with 1 to 4-SO$_3$H, —P(O)(OH)$_2$ or $R^{23}$, wherein each $R^{23}$ is independently $C_{1-6}$ alkyl optionally substituted with 1 or 2 substituents independently selected from the group consisting of SH, S—$C_{1-4}$ alkyl, —CON$R^{11}R^{11}$, and —N$R^{11}$Pr;
$R^7$ is hydrogen, $C_1$-$C_6$ alkyl or an amino acid side chain;
$R^8$ is hydrogen or $C_{1-6}$ alkyl;
each $R^{10}$ is independently selected from the group consisting of —N$R^{11}$Pr, —N$R^{11}$COCH$_2$Br, —COO$R^{12}$, —CON$R^{11}R^{11}$, N$R^{11}$CO$R^{13}$,

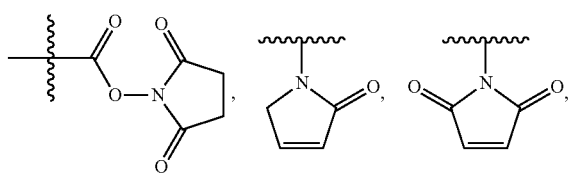

—S—S—$R^{13}$, —Si($R^{13}$)$_3$, alkyl, aryl, cycloalkyl, cycloalkenyl, heteroaryl, and heterocyclic;
each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo;
Pr is an amino protecting group;
$R^{12}$ is $C_1$-$C_6$ alkyl, or benzyl; and
$R^{13}$ is selected from the group consisting of alkyl, aryl, cycloalkyl, heteroaryl, and heterocyclic.

In some embodiments, provided is a method of preparing a compound of Formula II or a salt thereof:

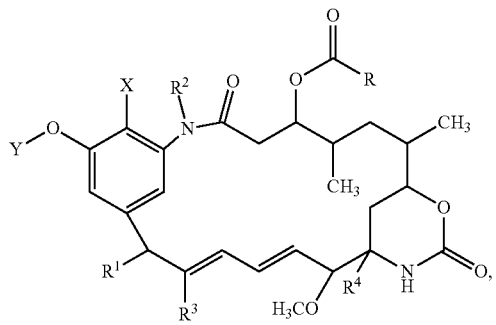

comprising contacting a compound of Formula II-A:

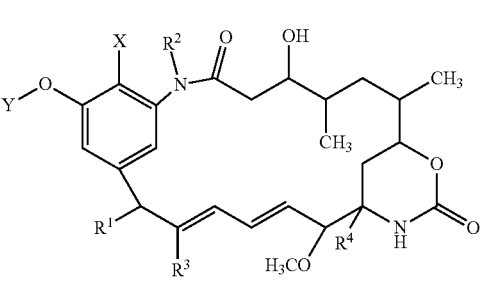

with a carboxylic acid of the formula R—COOH in the presence of a coupling reagent, a rare earth metal-based or trifluoromethanesulfonate-based Lewis acid catalyst and a base to form the compound of Formula II, or a salt thereof;
wherein
X is hydrogen or halo;
Y is selected from the group consisting of hydrogen, $C_1$-$C_6$ alkyl, $C_3$-$C_6$ cycloalkyl, benzyl, and —C(=O)$R^5$;
$R^1$ is hydrogen, —OH or —O$R^{17}$;
$R^2$ is hydrogen or $C_1$-$C_6$ alkyl;
$R^3$ is methyl, —CH$_2$OH or CH$_2$O$R^{17}$;
$R^4$ is —OH, —O$R^{17}$ or —SH;
$R^5$ is $C_1$-$C_6$ alkyl or benzyl;
$R^{17}$ is a hydroxy protecting group;
R is selected from the group consisting of alkyl, aryl, cycloalkyl, cycloalkenyl, heteroaryl, and heterocyclic, wherein the alkyl, aryl, cycloalkyl, cycloalkenyl, heteroaryl, or heterocyclic is optionally substituted with one to three $R^{10}$, or is

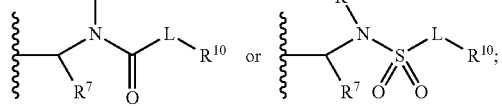

L is selected from optionally substituted $C_1$-$C_{20}$ alkylene, $C_3$-$C_8$ cycloalkylene, optionally substituted $C_1$-$C_{20}$ alkylene wherein one or more of the —CH$_2$— group is independently replaced with $C_3$-$C_8$ cycloalkylene, —O—, —S—, —N$R^8$—, —C(O)—, —C(=O)N$R^8$—, —N$R^8$C(=O)—, —SO$_2$N$R^8$—, or —N$R^8$SO$_2$—;

substituted $C_1$-$C_{20}$ alkylene is $C_1$-$C_{20}$ alkylene substituted with 1 to 4-$SO_3H$, —$P(O)(OH)_2$ or $R^{23}$, wherein each $R^{23}$ is independently $C_{1-6}$ alkyl optionally substituted with 1 or 2 substituents independently selected from the group consisting of SH, S—$C_{1-4}$ alkyl, —$CONR^{11}R^{11}$, and —$NR^{11}Pr$;

$R^7$ is hydrogen, $C_1$-$C_6$ alkyl or an amino acid side chain;

$R^8$ is hydrogen or $C_{1-6}$ alkyl;

each $R^{10}$ is independently selected from the group consisting of —$NR^{11}Pr$, —$NR^{11}COCH_2Br$, —$COOR^{12}$, —$CONR^{11}R^{11}$, —$NR^{11}COR^{13}$,

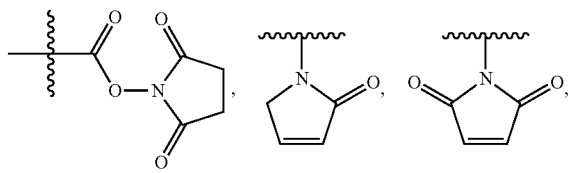

—S—S—$R^{13}$, —Si($R^{13}$)$_3$, alkyl, aryl, cycloalkyl, cycloalkenyl, heteroaryl, and heterocyclic;

each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo;

Pr is an amino protecting group;

$R^{12}$ is $C_1$-$C_6$ alkyl, or benzyl; and $R^{13}$ is selected from the group consisting of alkyl, aryl, cycloalkyl, heteroaryl, and heterocyclic.

In another aspect, provided is a method of preparing a compound of Formula III, or a salt thereof:

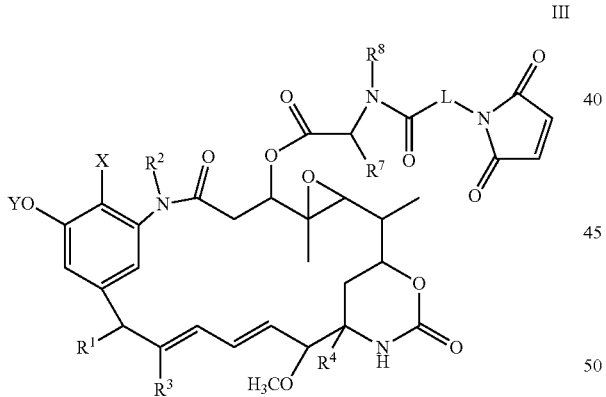

comprising contacting a compound of Formula III-A:

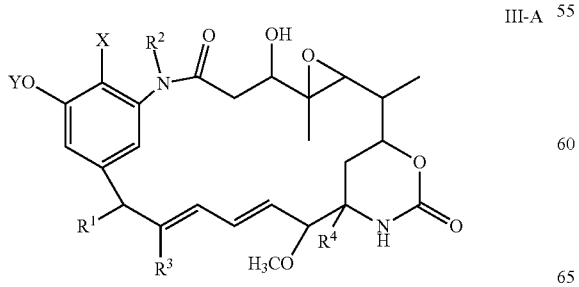

with a carboxylic acid of Formula III-B

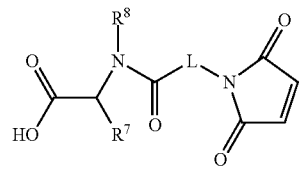

in the presence of a coupling reagent, a rare earth metal-based or trifluoromethanesulfonate-based Lewis acid catalyst and a base to form the compound of Formula III, or a salt thereof;

wherein

X is hydrogen or halo;

Y is selected from the group consisting of hydrogen, $C_1$-$C_6$ alkyl, $C_3$-$C_6$ cycloalkyl, and —C(=O)$R^5$;

$R^1$ is selected from the group consisting of hydrogen, —OH, or —$OR^{17}$;

$R^2$ is hydrogen or $C_1$-$C_6$ alkyl;

$R^3$ is methyl, —$CH_2OH$, or —$CH_2OR^{17}$;

$R^4$ is —OH, —$OR^{17}$ or —SH;

$R^5$ is $C_1$-$C_6$ alkyl or benzyl;

$R^{17}$ is a hydroxy protecting group;

$R^7$ is hydrogen, $C_1$-$C_6$ alkyl or an amino acid side chain;

$R^8$ is hydrogen or $C_{1-6}$ alkyl; and

L is selected from optionally substituted $C_1$-$C_{20}$ alkylene, $C_3$-$C_8$ cycloalkylene, and optionally substituted $C_1$-$C_{20}$ alkylene wherein one or more of the —$CH_2$— group is independently replaced with $C_3$-$C_8$ cycloalkylene, —O—, —S—, —$NR^8$—, —C(O)—, —C(=O)$NR^8$—, —$NR^8C(=O)$—, —$SO_2NR^8$—, or —$NR^8SO_2$—; wherein substituted $C_1$-$C_{20}$ alkylene is $C_1$-$C_{20}$ alkylene substituted with 1 to 4-$SO_3H$, —$P(O)(OH)_2$ or $R^{23}$, wherein each $R^{23}$ is independently $C_{1-6}$ alkyl optionally substituted with 1 or 2 substituents independently selected from the group consisting of SH, S—$C_{1-4}$ alkyl, —$CONR^{11}R^{11}$, and —$NR^{11}Pr$.

In another aspect, provided is a method of preparing a compound of Formula X

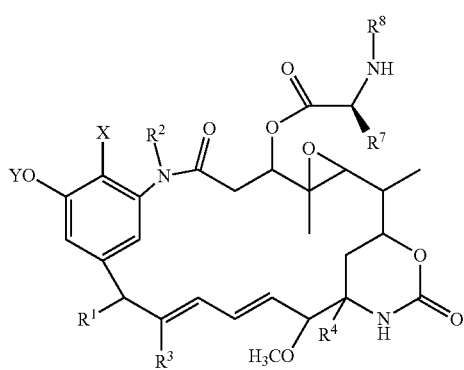

comprising deprotection of a compound of Formula X-A:

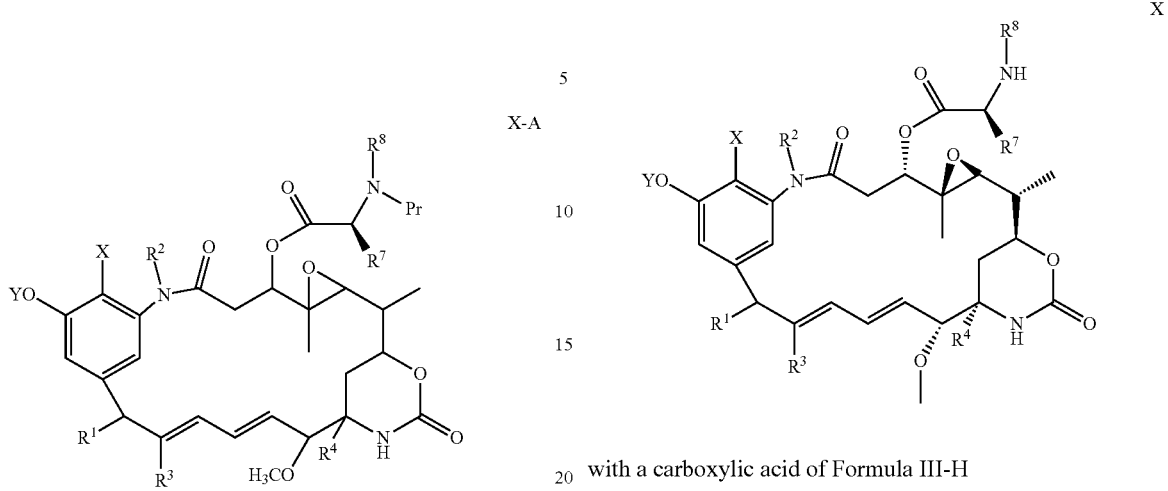

wherein
  X is hydrogen or halo;
  Y is selected from the group consisting of hydrogen, $C_1$-$C_6$ alkyl, $C_3$-$C_6$ cycloalkyl, and —C(=O)$R^5$;
  $R^1$ is selected from the group consisting of hydrogen, —OH, and —$OR^{17}$;
  $R^2$ is hydrogen or $C_1$-$C_6$ alkyl;
  $R^3$ is methyl, —$CH_2OH$, or —$CH_2OR^{17}$;
  $R^4$ is —OH, —$OR^{17}$ or —SH;
  $R^5$ is $C_1$-$C_6$ alkyl or benzyl;
  $R^{17}$ is a hydroxy protecting group;
  $R^7$ is hydrogen, $C_1$-$C_6$ alkyl or an amino acid side chain;
  $R^8$ is hydrogen or $C_{1-6}$ alkyl; and
  Pr is an amino protecting group, such as Boc or Fmoc.

In another aspect, provided is a method of preparing a compound of Formula XII,

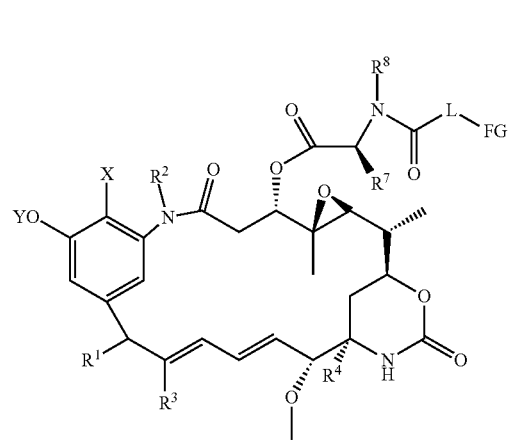

or a salt thereof, comprising contacting a compound of Formula X:

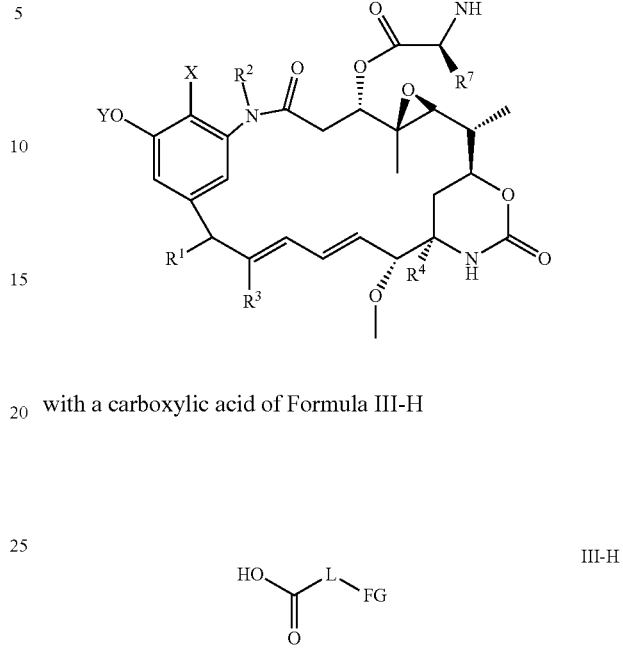

with a carboxylic acid of Formula III-H $$HO\underset{O}{\overset{}{\diagdown}}\overset{L}{\diagup}FG \qquad \text{III-H}$$

in the presence of a coupling reagent or directly with its active ester to form the compound of Formula XII, or a salt thereof;
wherein
  X is hydrogen or halo;
  Y is selected from the group consisting of hydrogen, $C_1$-$C_6$ alkyl, $C_3$-$C_6$ cycloalkyl, and —C(=O)$R^5$;
  $R^1$ is selected from the group consisting of hydrogen, —OH, and —$OR^{17}$;
  $R^2$ is hydrogen or $C_1$-$C_6$ alkyl;
  $R^3$ is methyl, —$CH_2OH$, or —$CH_2OR^{17}$;
  $R^4$ is —OH, —$OR^{17}$ or —SH;
  $R^5$ is $C_1$-$C_6$ alkyl or benzyl;
  $R^{17}$ is a hydroxy protecting group;
  $R^7$ is hydrogen, $C_1$-$C_6$ alkyl or an amino acid side chain;
  $R^8$ is hydrogen or $C_{1-6}$ alkyl; and
  L is selected from optionally substituted $C_1$-$C_{20}$ alkylene, $C_3$-$C_8$ cycloalkylene, and optionally substituted $C_1$-$C_{20}$ alkylene wherein one or more of the —$CH_2$— group is independently replaced with $C_3$-$C_8$ cycloalkylene, —O—, —S—, —C(O)—, —$NR^{10}$—, —C(=O)$NR^{10}$—, —$NR^{10}$C(=O)—, —$SO_2NR^{10}$—, or —$NR^{10}SO_2$—;
  substituted $C_1$-$C_{20}$ alkylene is $C_1$-$C_{20}$ alkylene substituted with 1 to 4-$SO_3H$, —P(O)(OH)$_2$ or $R^{23}$, wherein each $R^{23}$ is independently $C_{1-6}$ alkyl optionally substituted with 1 or 2 substituents independently selected from the group consisting of SH, S—$C_{1-4}$ alkyl, —$CONR^{11}R^{11}$, and —$NR^{11}$Pr;
  FG is independently selected from the group consisting of —$NR^{11}$Pr, —$NR^{11}COCH_2Br$, —$COOR^{12}$, $CONR^{11}R^{11}$, —$NR^{11}COR^{13}$,

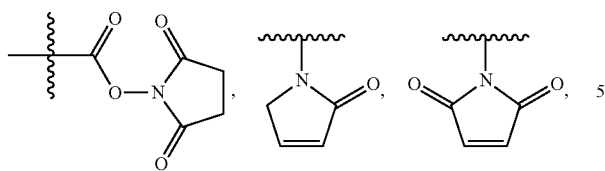

—S—S—$R^{13}$, —Si($R^{13}$)$_3$, alkyl, aryl, cycloalkyl, cycloalkenyl, heteroaryl, and heterocyclic;

each $R^{10}$ or $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo;

Pr is an amino protecting group;

$R^{12}$ is $C_1$-$C_6$ alkyl, or benzyl; and each $R^{13}$ is independently selected from the group consisting of alkyl, aryl, cycloalkyl, heteroaryl, and heterocyclic.

In another aspect, provided is a method of preparing a compound of Formula III, or a salt thereof:

III

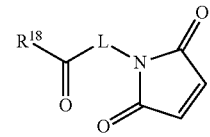

comprising contacting a compound of Formula X:

X

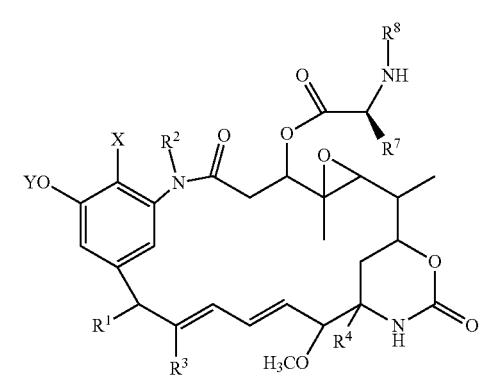

with a carboxylic acid of Formula III-C

III-C

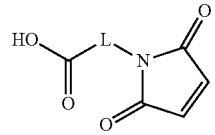

in the presence of a coupling reagent or with a compound of Formula III-F

III-F

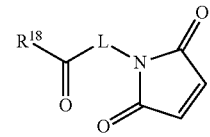

wherein $R^{18}$ is halo or —O—$R^{19}$, wherein $R^{19}$ is selected from the group consisting of —CH=CH$_2$, -cyanomethyl, -pyridyl, halo or nitro substituted phenyl (e.g., 4-nitrophenyl, 2,4,6-trichlorophenyl, pentachlorophenyl, pentafluorophenyl), phthalimido, succinimido, N-benxotriazolyl, to form the compound of Formula III, or a salt thereof;

wherein

X is hydrogen or halo;

Y is selected from the group consisting of hydrogen, $C_1$-$C_6$ alkyl, $C_3$-$C_6$ cycloalkyl, and —C(=O)$R^5$;

$R^1$ is selected from the group consisting of hydrogen, —OH, and —O$R^{17}$;

$R^2$ is hydrogen or $C_1$-$C_6$ alkyl;

$R^3$ is methyl, —CH$_2$OH, or —CH$_2$O$R^{17}$;

$R^4$ is —OH, —O$R^{17}$ or —SH;

$R^5$ is $C_1$-$C_6$ alkyl or benzyl;

$R^{17}$ is a hydroxy protecting group;

$R^7$ is hydrogen, $C_1$-$C_6$ alkyl or an amino acid side chain;

$R^8$ is hydrogen or $C_{1-6}$ alkyl; and

L is selected from optionally substituted $C_1$-$C_{20}$ alkylene, $C_3$-$C_8$ cycloalkylene, and optionally substituted $C_1$-$C_{20}$ alkylene wherein one or more of the —CH$_2$— group is independently replaced with $C_3$-$C_8$ cycloalkylene, —O—, —S—, —N$R^8$—, —C(O)—, —C(=O)N$R^8$—, —N$R^8$C(=O)—, —SO$_2$N$R^8$—, or —N$R^8$SO$_2$—; wherein substituted $C_1$-$C_{20}$ alkylene is $C_1$-$C_{20}$ alkylene substituted with 1 to 4-SO$_3$H, —P(O)(OH)$_2$ or $R^{23}$, wherein each $R^{23}$ is independently $C_{1-6}$ alkyl optionally substituted with 1 or 2 substituents independently selected from the group consisting of SH, S—$C_{1-4}$ alkyl, —CON$R^{11}R^{11}$, and —N$R^{11}$Pr.

In another aspect, provided is a method of preparing a compound of Formula XIV,

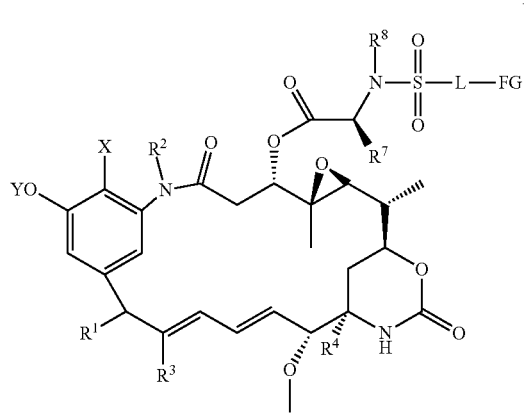

or a salt thereof, comprising contacting a compound of Formula X:

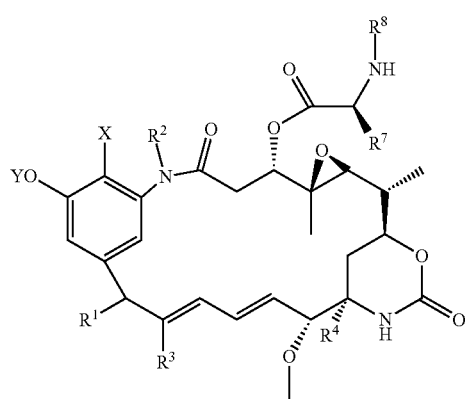

with a sulfonyl chloride of Formula XIV-A

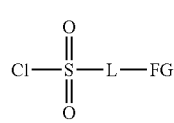

in the presence of a base to form the compound of Formula XIV, or a salt thereof;
wherein
X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, and —O$R^{17}$;
$R^2$ is hydrogen or $C_1$-$C_6$ alkyl;
$R^3$ is methyl, —CH$_2$OH, or —CH$_2$O$R^{17}$;
$R^4$ is —OH, —O$R^{17}$ or —SH;
$R^5$ is $C_1$-$C_6$ alkyl or benzyl;
$R^{17}$ is a hydroxy protecting group;
$R^7$ is hydrogen, $C_1$-$C_6$ alkyl or an amino acid side chain;
$R^8$ is hydrogen or $C_{1-6}$ alkyl; and
L is selected from optionally substituted $C_1$-$C_{20}$ alkylene, $C_3$-$C_8$ cycloalkylene, and optionally substituted $C_1$-$C_{20}$ alkylene wherein one or more of the —CH$_2$— group is independently replaced with $C_3$-$C_8$ cycloalkylene, —O—, —S—, —C(O)—, —N$R^{10}$—, —C(=O)N$R^{10}$—, —N$R^{10}$C(=O)—, —SO$_2$N$R^{10}$—, or —N$R^{10}$SO$_2$—;
substituted $C_1$-$C_{20}$ alkylene is $C_1$-$C_{20}$ alkylene substituted with 1 to 4-SO$_3$H, —P(O)(OH)$_2$ or $R^{23}$, wherein each $R^{23}$ is independently $C_{1-6}$ alkyl optionally substituted with 1 or 2 substituents independently selected from the group consisting of SH, S—$C_{1-4}$ alkyl, —CON$R^{11}R^{11}$, and —N$R^{11}$Pr;
FG is independently selected from the group consisting of —N$R^{11}$Pr, —N$R^{11}$COCH$_2$Br, —COO$R^{12}$, —CON$R^{11}R^{11}$, —N$R^{11}$CO$R^{13}$,

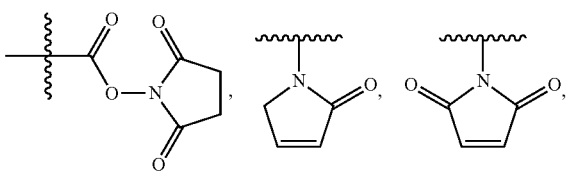

—S—S—$R^{13}$, —Si($R^{13}$)$_3$, alkyl, aryl, cycloalkyl, cycloalkenyl, heteroaryl, and heterocyclic;
each $R^{10}$ or $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo;
Pr is an amino protecting group;
$R^{12}$ is $C_1$-$C_6$ alkyl, or benzyl; and
each $R^{13}$ is independently selected from the group consisting of alkyl, aryl, cycloalkyl, heteroaryl, and heterocyclic.

In another aspect, provided is a method of preparing a compound of Formula XV, or a salt thereof:

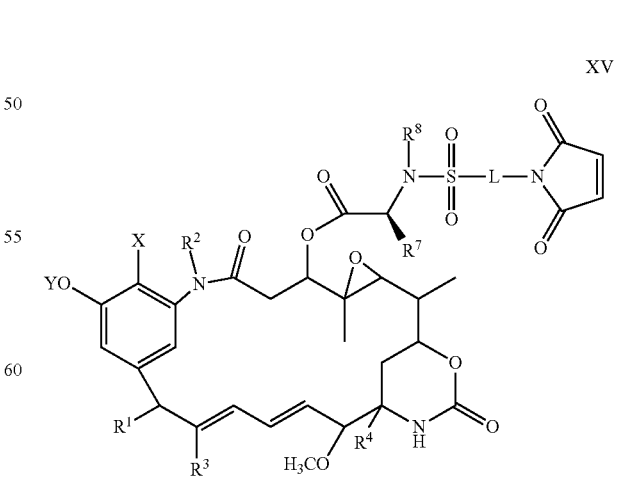

comprising contacting a compound of Formula X:

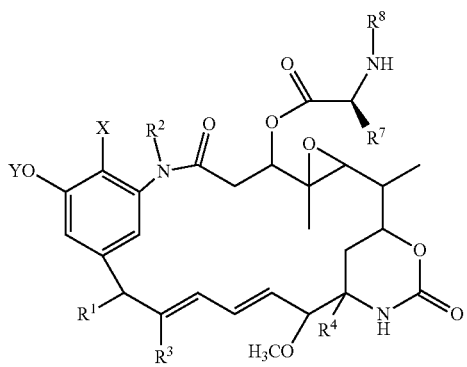

with a sulfonyl chloride of Formula XV-A

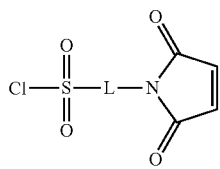

in the presence of a base to form the compound of Formula XV, or a salt thereof;
wherein
X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, and —O$R^{17}$;
$R^2$ is hydrogen or $C_1$-$C_6$ alkyl;
$R^3$ is methyl, —CH$_2$OH, or —CH$_2$O$R^{17}$;
$R^4$ is —OH, —O$R^{17}$ or —SH;
$R^5$ is $C_1$-$C_6$ alkyl or benzyl;
$R^{17}$ is a hydroxy protecting group;
$R^7$ is hydrogen, $C_1$-$C_6$ alkyl or an amino acid side chain;
$R^8$ is hydrogen or $C_{1-6}$ alkyl; and
L is selected from optionally substituted $C_1$-$C_{20}$ alkylene, $C_3$-$C_8$ cycloalkylene, and optionally substituted $C_1$-$C_{20}$ alkylene wherein one or more of the —CH$_2$— group is independently replaced with $C_3$-$C_8$ cycloalkylene, —O, S, C(O)—, —N$R^8$—, —C(=O)N$R^8$—, —N$R^8$C(=O)—, —SO$_2$N$R^8$—, or —N$R^8$SO$_2$—; wherein substituted $C_1$-$C_{20}$ alkylene is $C_1$-$C_{20}$ alkylene substituted with 1 to 4-SO$_3$H, —P(O)(OH)$_2$ or $R^{23}$, wherein each $R^{23}$ is independently $C_{1-6}$ alkyl optionally substituted with 1 or 2 substituents independently selected from the group consisting of SH, S—$C_{1-4}$ alkyl, —CON$R^{11}R^{11}$, and —N$R^{11}$Pr.

DETAILED DESCRIPTION

Definitions

As used herein, unless otherwise stated, the singular forms "a," "an," and "the" include plural reference. Thus, for example, a reference to "a compound" includes a plurality of compounds.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% or plus or minus 5%, or plus or minus 1% of the particular term.

As used herein, the term "comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

As used herein, "maytansinoid" refers to a maytansine analogue having a 3-hydroxy group. Maytansine can be isolated from plants of the genus Maytenus (U.S. Pat. No. 3,896,111). It is of the formula:

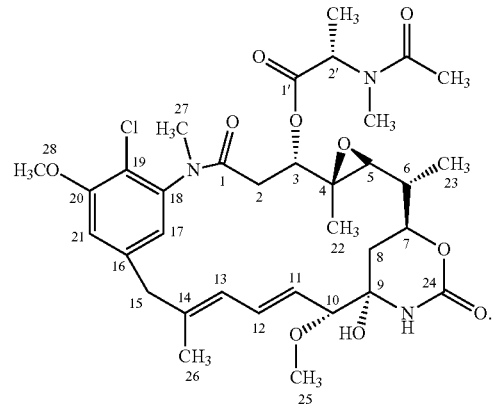

Maytansinoids that can be used on the processes described herein are the 3-hydroxy derivatives of maytansine or a stereoisomer of maytansine such as a compound of the formula:

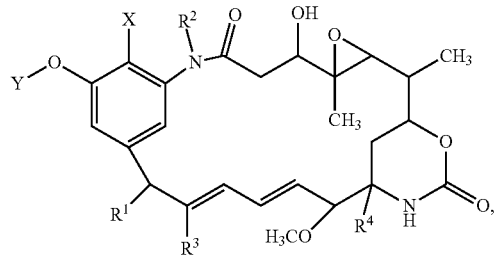

wherein X, Y, $R^1$, $R^2$, $R^3$, and $R^4$ are as defined herein, including pure stereoisomers thereof. Certain maytansinoids are described in J. M. CASSADY, et al., Recent Developments in the Maytansinoid Antitumor Agents, *Chem. Pharm. Bull.* 52(1) 1-26 (2004), U.S. Pat. Nos. 4,256,746, 6,333,410, which are incorporated by reference in their entirety. In some embodiments, the maytansinoid is of the formula:

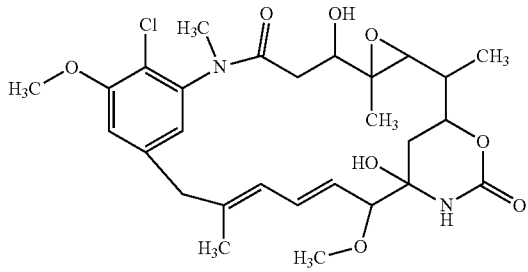 [SMILES: COc1cc2cc(c1Cl)N(C)C(=O)CC(O)C1(C)OC1C(C)C1CC(O)(NC(=O)O1)C(OC)/C=C/C=C(\C)C2]

including pure stereoisomers thereof. "Maytansinol" refers to a maytansinoid of the formula:

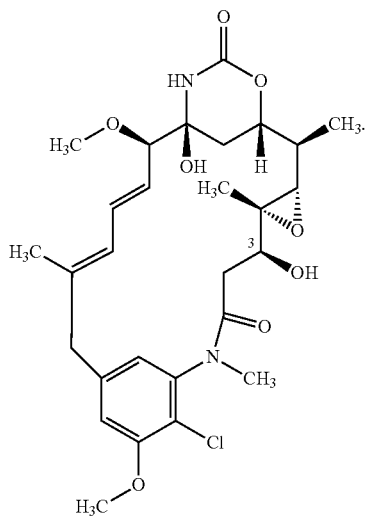

"Maytansinoid C-3 ester" refers to the product of a coupling reaction of a maytansinoid with a carboxylic acid where the 3-hydroxy group of the maytansinoid is esterified by the carboxylic acid. Such a coupling reaction is also referred to as "maytansinoid C-3 esterification."

"Rare earth metal-based Lewis acid" is a Lewis acid comprising at least one rare earth metal atom. "Trifluoromethanesulfonate-based Lewis acid" is a Lewis acid comprising at least one trifluoromethanesulfonate group. A Lewis acid is a molecule that is an electron-pair acceptor and capable of reacting with a Lewis base to form a Lewis adduct, by sharing the electron pair furnished by the Lewis base. Examples of rare earth metal-based Lewis acid include, but are not limited to, lanthanide-based Lewis acid, such as lanthanide triflates ($Ln(OTf)_3$), ytterbium triflate, vanadyl triflate, and scandium-based Lewis acid such as scandium triflate ($Sc(OTf)_3$). Examples of trifluoromethanesulfonate-based Lewis acid include, but are not limited to, lanthanide triflates, vanadyl triflate and scandium triflate.

"Coupling reagent" refers to a reagent that may be used to form an ester bond between a hydroxy (OH) group and a carboxy group or an amide bond between an amino group and a carboxy group. Examples of coupling reagents include, but are not limited to, carbodiimides such as N—N'-dicyclohexylcarbodiimide (DCC), N—N'-diisopropylcarbodiimide (DIC), and 1-ethyl-3-(3'-dimethylaminopropyl)carbodiimide (EDCI); aminium compounds such as N-[(dimethylamino)-1H-1,2,3-triazolo[4,5-b]pyridine-1-ylmethylene]-N-methyl-methanaminium hexafluorophosphate N-oxide (HATU), N-[(1H-benzotriazol-1-yl)(dimethylamino)methylene]-N-methylmethanaminium hexafluorophosphate N-oxide (HBTU), N-[(1H-6-chlorobenzotriazol-1-yl)(dimethylamino)methylene]-N-methylmethanaminium hexafluorophosphate N-oxide (HCTU), N-[(1H-benzotriazol-1-yl)(dimethylamino)methylene]-N-methylmethanaminium tetrafluoroborate N-oxide (TBTU), and N-[(1H-6-chlorobenzotriazol-1-yl)(dimethylamino)methylene]-N-methylmethanaminium tetrafluoroborate N-oxide (TCTU); and phosphonium compounds such as 7-azabenzotriazol-1-yl-N-oxy-tris(pyrrolidino)phosphonium hexafluorophosphate (PyAOP) and benzotriazol-1-yl-N-oxy-tris(pyrrolidino)phosphonium hexafluorophosphate (PyBOP).

"Alkyl" refers to monovalent saturated aliphatic hydrocarbyl groups having from 1 to 10 carbon atoms and preferably 1 to 6 carbon atoms. $C_v$ alkyl wherein v is an integer represents an alkyl having v carbons. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkylene" is a divalent saturated aliphatic hydrocarbyl groups having from 1 to 10 carbon atoms and preferably 1 to 6 carbon atoms.

"Alkenyl" refers to straight or branched hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—$CH_2$C≡CH).

"Amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When R' is hydrogen and R" is alkyl, the substituted amino group is sometimes referred to herein as alkylamino. When R' and R" are alkyl, the substituted amino group is sometimes referred to herein as dialkylamino. —$NH_2$ is also referred as unsubstituted amino. When referring to a monosubstituted amino, it is meant that either R' and R" is hydrogen but not both. When referring to a disubstituted amino, it is meant that neither R' and R" are hydrogen.

"Amino protecting group" is a group that prevents an amino group from interfering with a chemical reaction in which the amino group is not intended to participate, which group can be removed to release the free amino group when needed. Amino protecting groups are known in the field and illustrated by N-tert-butoxycarbonyl (t-Boc), 9-fluorenylmethoxycarbonyl (Fmoc), carboxybenzyl (Cbz), acetyl (Ac), benzoyl (Bz), p-methoxybenzyl carbonyl (Moz or MeOZ), benzyl (Bn), p-methoxybenzyl (PMB), 3,4-dimethoxybenzyl (DMPM), p-methoxyphenyl (PMP), etc, and others described in T. W. Greene and G. M. Wuts, *Protecting Groups in Organic Synthesis*, Third Edition, Wiley, New York, 1999, and references cited therein.

"Protected amino group" is an unsubstituted amino or monosubstituted amino group wherein one or both of the hydrogen is replaced with an amino protecting group.

"Amino acid" refers any compound, whether natural, unnatural or synthetic, which includes both an amino group and a carboxy group. Examples of amino acid include, but are not limited to glycine ($NH_2CH_2COOH$), cysteine, alanine, N-methyl-L-alanine, including both the D and L optical isomers. "Amino acid side chain" refers to the substituent that replaces a hydrogen of the methylene group of glycine. Examples of an amino acid side chain include, but are not limited to the side chains of the natural amino acids, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic.

"N-protected amino acid" refers to an amino acid wherein the amino group is protected with an amino protecting group.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Carbonyl" refers to the divalent group —C(O)— which is equivalent to —C(=O)—.

"Carboxy" or "carboxyl" refers to —COOH or $CO_2H$, or salts thereof.

"Carboxylic acid" refers to a compound having at least one carboxy.

"Cyano" refers to the group —CN.

"Cycloalkyl" refers to cyclic alkyl groups of from 3 to 10 carbon atoms having single or multiple cyclic rings including fused, bridged, and spiro ring systems. One or more of the rings can be aryl, heteroaryl, or heterocyclic provided that the point of attachment is through the non-aromatic, non-heterocyclic ring carbocyclic ring. Examples of suitable cycloalkyl groups include, for instance, cyclopropyl, cyclobutyl, cyclopentyl, and cyclooctyl. Other examples of cycloalkyl groups include bicycle[2,2,2,]octanyl, norbornyl, and spirobicyclo groups such as spiro[4.5]dec-8-yl:

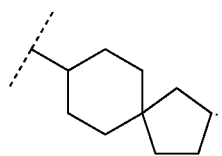

"Cycloalkenyl" refers to non-aromatic cyclic alkyl groups of from 3 to 10 carbon atoms having single or multiple cyclic rings and having at least one >C=C< ring unsaturation and preferably from 1 to 2 sites of >C=C< ring unsaturation.

"Halo" or "halogen" refers to fluoro, chloro, bromo and iodo and preferably is fluoro or chloro.

"Haloalkyl" refers to alkyl groups substituted with 1 to 5, 1 to 3, or 1 to 2 halo groups, wherein alkyl and halo are as defined herein.

"Hydroxy" or "hydroxyl" refers to the group —OH.

"Hydroxy protecting group" refers to a protecting group for an OH group. Suitable hydroxy protecting groups as well as suitable conditions for protecting and deprotecting particular functional groups are well known in the art. For example, numerous such protecting groups are described in T. W. Greene and P. G. M. Wuts, Protecting Groups in Organic Synthesis, Third Edition, Wiley, New York, 1999. Such hydroxy protecting groups include $C_{1-6}$ alkyl ethers, benzyl ethers, p-methoxybenzyl ethers, silyl ethers (—O—Si—$R^{21}R^{21}R^{21}$ (wherein each $R^{21}$ is independently selected from the group consisting of alkyl, alkenyl, alkynyl, aryl, cycloalkyl, cycloalkenyl, heteroaryl, and heterocyclic) such as trimethylsilyl (TMS), tert-butyldiphenylsilyl (TBDPS), tert-butyldimethylsilyl (TBS/TBDMS) and triisopropylsilyl (TIPS)), esters (—O—C(=O)$R^{21}$), carbonates (—O—C(=O)O$R^{21}$), and the like.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the heteroaryl is a 5- or 6-membered heteroaryl which has 5 or 6 ring atoms with 1 to 4 heteroatoms. In one embodiment, the nitrogen and/or the sulfur ring atom(s) of the heteroaryl group are optionally oxidized to provide for the N-oxide (N→O), or sulfonyl moieties. Preferred heteroaryls include pyridinyl, pyrrolyl, indolyl, thiophenyl, and furanyl.

"Heterocycle" or "heterocyclic" or "heterocycloalkyl" or "heterocyclyl" refers to a saturated or partially saturated, but not aromatic, group having from 3 to 10 ring carbon atoms and from 1 to 4 ring heteroatoms selected from the group consisting of nitrogen, sulfur, or oxygen. In one embodiment, the heterocycle is a 5-, 6- or 7-membered heteroaryl which has 5, 6 or 7 ring atoms with 1 to 4 heteroatoms. Heterocycle encompasses single ring or multiple condensed rings, including fused bridged and spiro ring systems. In fused ring systems, one or more the rings can be cycloalkyl, aryl, or heteroaryl provided that the point of attachment is through the non-aromatic ring. In one embodiment, the nitrogen and/or sulfur atom(s) of the heterocyclic group are optionally oxidized to provide for the N-oxide, or sulfonyl moieties.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Substituted alkyl," "substituted alkenyl," "substituted alkynyl," "substituted cycloalkyl," "substituted cycloalkenyl," "substituted aryl," "substituted heteroaryl" or "substituted heterocyclic" refers to an alkyl, alkenyl, alkynyl, cycloalkyl, cycloalkenyl, aryl, heteroaryl or heterocyclic group, respectively, which is substituted with 1 to 5, preferably 1 to 3, or more preferably 1 to 2 substituents selected from the group consisting of alkyl, halo alkyl, —O—$R^{20}$, —S—$R^{20}$, alkenyl, alkynyl, oxo, —C(=O)$R^{20}$, —C(=S)$R^{20}$, —C(=O)O$R^{20}$, —N$R^{20}$C(=O)$R^{21}$, —OC(=O)$R^{21}$, —N$R^{20}R^{20}$, —C(=O)N$R^{20}R^{20}$, —C(=S)N$R^{20}R^{20}$, —N$R^{20}R^{20}$, —N$R^{20}$C(=S)N$R^{20}R^{20}$, —OC(=O)N$R^{20}R^{20}$, —SO$_2$N$R^{20}R^{20}$, —OSO$_2$N$R^{20}R^{20}$, —N$R^{20}$SO$_2$N$R^{20}R^{20}$, —C(=N$R^{20}$)N$R^{20}R^{20}$, aryl, —N$R^{20}$C(=O)O$R^{21}$, —OC(=O)O$R^{21}$, cyano, cycloalkyl, cycloalkenyl, —N$R^{20}$C(=N$R^{20}$)N$R^{20}R^{20}$, halo, hydroxy, heteroaryl, heterocyclic, nitro, —SO$_3$H, —SO$_2R^{21}$, and —OSO$_2R^{21}$, wherein each $R^{20}$ is independently selected from the group consisting of hydrogen, alkyl, alkenyl, alkynyl, aryl, cycloalkyl, cycloalkenyl, heteroaryl, and heterocyclic, or two $R^{20}$ with the atom(s) bound thereto form a heterocyclic ring, and $R^{21}$ is selected from the group consisting of alkyl, alkenyl, alkynyl, aryl, cycloalkyl, cycloalkenyl, heteroaryl, and heterocyclic.

"Nitro" refers to the group —NO$_2$.

"Oxo" refers to the atom (=O) or (—O$^-$).

"Spiro ring systems" refers to bicyclic ring systems that have a single ring carbon atom common to both rings.

"Dithio" refers to the group —S—S—$R^{20}$ or —S—S—$R^{21}$.

"Compound" or "compounds" as used herein is meant to include the stereoisomers and tautomers of the indicated formulas.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

Esterfication Process

In one aspect, provided is an efficient method for esterification of a maytansinoid with a carboxylic acid to prepare a maytansinoid C-3 ester in high yield using a rare earth metal-based or trifluoromethanesulfonate-based Lewis acid catalyst and a base together with a coupling reagent.

The carboxylic acid used in the coupling reaction can be any type of carboxylic acid, for example, carboxylic acids further substituted with a functional group such as ester, amide, dithio.

In some embodiments, the present invention provides a method of preparing a maytansinoid C-3 ester compound of Formula I, or a salt thereof:

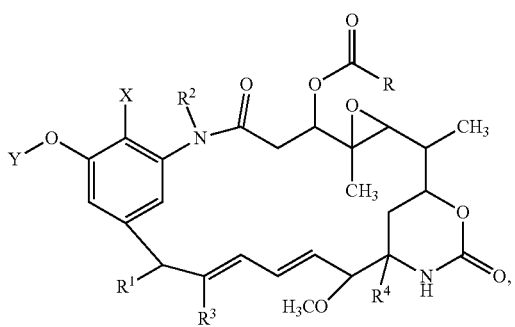

comprising contacting a maytansinoid compound of Formula I-A:

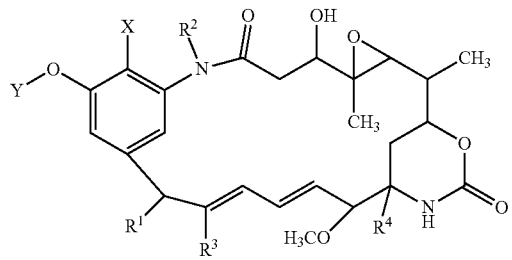

with a carboxylic acid of the formula R—COOH in the presence of a coupling reagent, a rare earth metal-based or trifluoromethanesulfonate-based Lewis acid catalyst and a base to form the compound of Formula I, or a salt thereof;

wherein
X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, and —O$R^{17}$;
$R^2$ is hydrogen or $C_1$-$C_6$ alkyl;
$R^3$ is methyl, —CH$_2$OH, or —CH$_2$O$R^{17}$;
$R^4$ is —OH, —O$R^{17}$ or —SH;
$R^5$ is $C_1$-$C_6$ alkyl or benzyl;
$R^{17}$ is a hydroxy protecting group;
R is selected from the group consisting of alkyl, aryl, cycloalkyl, cycloalkenyl, heteroaryl, and heterocyclic, wherein the alkyl, aryl, cycloalkyl, cycloalkenyl, heteroaryl, or heterocyclic is optionally substituted with one to three $R^{10}$, or is

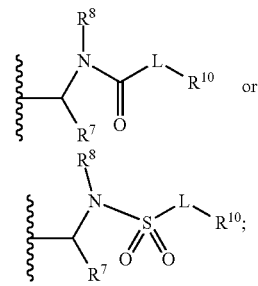

L is selected from optionally substituted $C_1$-$C_{20}$ alkylene, $C_3$-$C_8$ cycloalkylene, and optionally substituted $C_1$-$C_{20}$ alkylene wherein one or more of the —CH$_2$— group is independently replaced with $C_3$-$C_8$ cycloalkylene, —O—, —S—, —N$R^8$—, —C(O)—, —C(=O)N$R^8$—, —N$R^8$C(=O)—, —SO$_2$N$R^8$—, or —N$R^8$SO$_2$—;

substituted $C_1$-$C_{20}$ alkylene is $C_1$-$C_{20}$ alkylene substituted with 1 to 4-SO$_3$H, —P(O)(OH)$_2$ or $R^{23}$, wherein each $R^{23}$ is independently $C_{1-6}$ alkyl optionally substituted with 1 or 2 substituents independently selected from the group consisting of SH, S—$C_{1-4}$ alkyl, —CONR$^{11}R^{11}$, and —NR$^{11}$Pr;

$R^7$ is hydrogen, $C_1$-$C_6$ alkyl or an amino acid side chain;
$R^8$ is hydrogen or $C_{1-6}$ alkyl;
each $R^{10}$ is independently selected from the group consisting of —NR$^{11}$Pr, —NR$^{11}$COCH$_2$Br, —COO$R^{12}$, —CONR$^{11}R^{11}$, —NR$^{11}$COR$^{13}$,

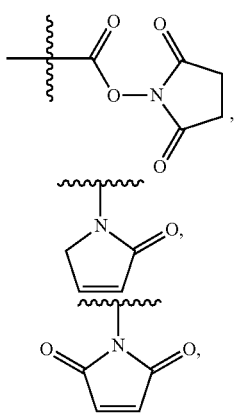

—S—S—$R^{13}$, —Si($R^{13}$)$_3$, alkyl, aryl, cycloalkyl, cycloalkenyl, heteroaryl, and heterocyclic;

each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo;

Pr is an amino protecting group;

$R^{12}$ is $C_1$-$C_6$ alkyl, or benzyl; and $R^{13}$ is selected from the group consisting of alkyl, aryl, cycloalkyl, heteroaryl, and heterocyclic.

In some embodiments, the present invention provides a method of preparing a compound of Formula II, or a salt thereof:

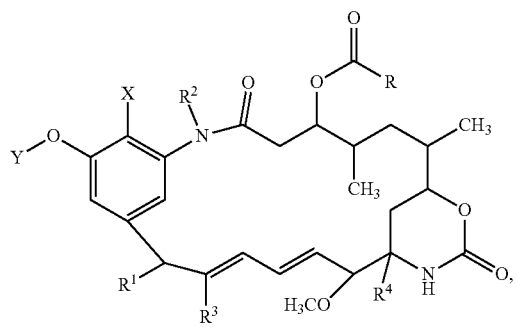

II comprising contacting a compound of Formula II-A:

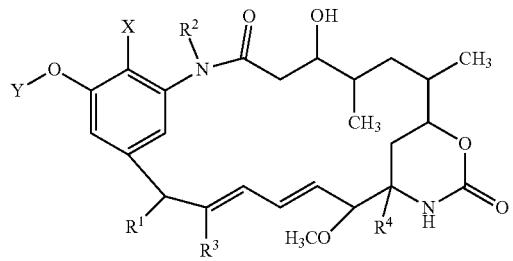

II-A with a carboxylic acid of the formula R—COOH in the presence of a coupling reagent, a rare earth metal-based or trifluoromethanesulfonate-based Lewis acid catalyst and a base to form the compound of Formula II, or a salt thereof;

wherein

X is hydrogen or halo;

Y is selected from the group consisting of hydrogen, $C_1$-$C_6$ alkyl, $C_3$-$C_6$ cycloalkyl, and —C(=O)$R^5$;

$R^1$ is selected from the group consisting of hydrogen, —OH, and —OR$^{17}$;

$R^2$ is hydrogen or $C_1$-$C_6$ alkyl;

$R^3$ is methyl, —CH$_2$OH, or CH$_2$OR$^{17}$;

$R^4$ is —OH, —OR$^{17}$ or —SH;

$R^5$ is $C_1$-$C_6$ alkyl or benzyl;

$R^{17}$ is a hydroxy protecting group;

R is selected from the group consisting of alkyl, aryl, cycloalkyl, cycloalkenyl, heteroaryl, and heterocyclic, wherein the alkyl, aryl, cycloalkyl, cycloalkenyl, heteroaryl, or heterocyclic is optionally substituted with one to three $R^{10}$, or is

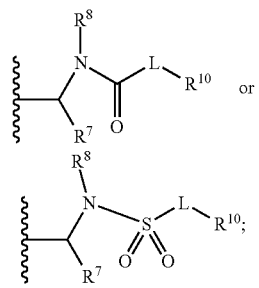

L is selected from optionally substituted $C_1$-$C_{20}$ alkylene, $C_3$-$C_8$ cycloalkylene, and optionally substituted $C_1$-$C_{20}$ alkylene wherein one or more of the —CH$_2$— group is independently replaced with $C_3$-$C_8$ cycloalkylene, —O—, —S—, —NR$^8$—, —C(O)—, —C(=O)NR$^8$—, —NR$^8$C(=O)—, —SO$_2$NR$^8$—, or —NR$^8$SO$_2$—;

substituted $C_1$-$C_{20}$ alkylene is $C_1$-$C_{20}$ alkylene substituted with 1 to 4-SO$_3$H, —P(O)(OH)$_2$ or $R^{23}$, wherein each $R^{23}$ is independently $C_{1-6}$ alkyl optionally substituted with 1 or 2 substituents independently selected from the group consisting of SH, S—$C_{1-4}$ alkyl, —CONR$^{11}$R$^{11}$, and —NR$^{11}$Pr;

$R^7$ is hydrogen, $C_1$-$C_6$ alkyl or an amino acid side chain;

$R^8$ is hydrogen or $C_{1-6}$ alkyl;

each $R^{10}$ is independently selected from the group consisting of —NR$^{11}$Pr, —NR$^{11}$COCH$_2$Br, —COOR$^{12}$, —CONR$^{11}$R$^{11}$, —NR$^{11}$COR$^{13}$,

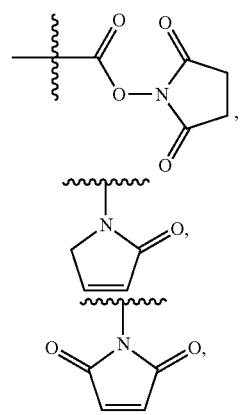

—S—S—R$^{13}$, —Si(R$^{13}$)$_3$, alkyl, aryl, cycloalkyl, cycloalkenyl, heteroaryl, and heterocyclic;

each R$^{11}$ is independently hydrogen, alkyl, aryl, cycloalkyl, cycloalkenyl, heteroaryl, and heterocyclic, or the two R$^{11}$ together with the nitrogen form a heterocyclic, wherein the heterocyclic is optionally substituted with one or two oxo;

Pr is an amino protecting group;

R$^{12}$ is C$_1$-C$_6$ alkyl, or benzyl; and

R$^{13}$ is selected from the group consisting of alkyl, aryl, cycloalkyl, heteroaryl, and heterocyclic.

In some embodiments, the carboxylic acid (or R—COOH) is:

1) simple carboxylic acid such as acetic acid, isobutric acid or adipic acid mono 2-trimethylsilylethyl ester (exemplified in Scheme 1);
2) N-protected amino acid, such as N-acylated-N-methylalanine derivatives (exemplified in Scheme 2) or N-Fmoc-N-methyl-alanine derivatives (exemplified in Example 10); or
3) N- and S-protected cysteine or methionine derivates (exemplified in Scheme 3).

In some embodiments, R is C$_1$-C$_6$ alkyl, or C$_1$-C$_6$ alkyl substituted with —Si(R$^{13}$)$_3$.

In some embodiments, R is C$_1$-C$_6$ alkyl substituted with —NR$^{11}$Pr. In some embodiments, Pr is Fmoc. In some embodiments, R—COOH is

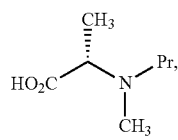

for example,

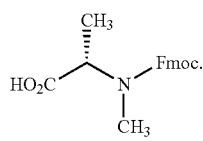

In some embodiments, R is C$_1$-C$_6$ alkyl substituted with —NR$^{11}$COR$^{13}$ and —S—S—R$^{13}$, wherein R$^{11}$ and R$^{13}$ are as defined herein and R$^{13}$ can be the same or different.

In some embodiments, R$^{11}$ is C$_1$-C$_6$ alkyl, for example, methyl. In some embodiments, R$^{13}$ is C$_1$-C$_{10}$ alkyl, for example, methyl. In some embodiments, R$^{13}$ is heteroaryl, for example, pyridyl. In some embodiments, R$^{13}$ is aryl, for example, phenyl.

In some embodiments, R—COOH is

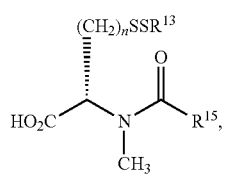

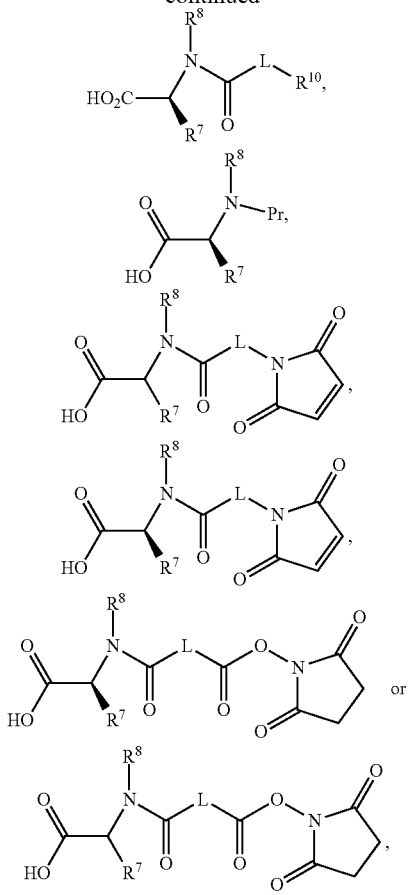

wherein L, R$^7$, R$^8$ and R$^{10}$ are as defined herein, Pr is an amino protecting group, n is 1 or 2, R$^{13}$ is C$_1$-C$_6$ alkyl, for example, methyl, or heteroaryl, for example, pyridyl, and R$^{15}$ is C$_1$-C$_{10}$ alkyl, for example, methyl, or aryl, for example, phenyl. In some embodiments, Pr is Fmoc.

In some embodiments, R—COOH is

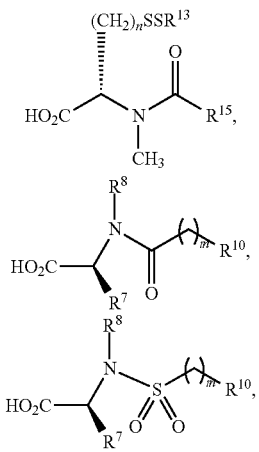

wherein m is selected from an integer of 1 to 20, preferably 1 to 10, more preferably 5 to 10; n is 1 or 2; R$^{13}$ is C$_1$-C$_6$ alkyl, for example, methyl, or heteroaryl, for example, pyridyl; R$^{15}$ is C$_1$-C$_6$ alkyl, for example, methyl, or aryl, for example, phenyl; R$^7$, R$^8$ and R$^{10}$ are as defined herein.

In some embodiments, R—COOH is an amino acid or amino acid derivative, such as N-methyl-L-alanine, L-cysteine or L-methionine or a derivative, wherein the amino group is protected by a Pr group. If the amino acid comprises two or more amino groups, such as lysine, the amino groups can be protected by the same or different Pr groups. If the amino acid comprises two or more carboxy groups, such as aspartic acid or glutamic acid, the other carboxy group(s) can be protected by a carboxy protecting group, such as alkyl ester, or a benzyl ester, leaving one free carboxy group for coupling with the maytansinoid. Other functional groups on an amino acid or amino acid derivative can be protected by protecting groups known in the art. For example, protecting groups are described in T. W. Greene and G. M. Wuts, Protecting Groups in Organic Synthesis, Third Edition, Wiley, New York, 1999, and references cited therein.

In some embodiments, R—COOH is selected from the group consisting of $CH_3COOH$, $(CH_3)_2CHCOOH$, and $(CH_3)_3Si(CH_2)_2C(=O)(CH_2)_4COOH$.

In some embodiments, R—COOH is selected from the group consisting

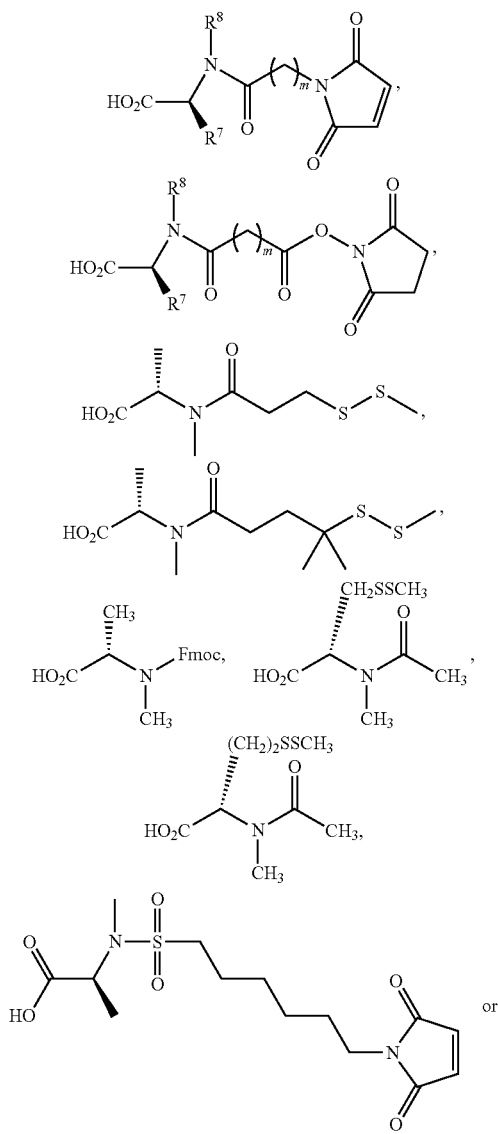

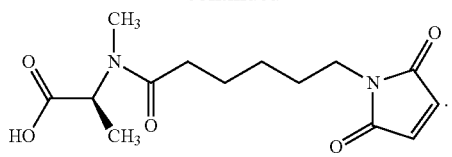

In some embodiments, the present invention provides a method for stereoselective C-3 esterification of a maytansinoid with a chiral amino acid derivative, such as N-methyl-L-alanine, L-cysteine and L-methionine derivatives, to prepare a maytansinoid C-3 ester, such as maytansinoid C-3 N-methyl-L-alanine, L-cysteine and L-methionine esters, in high yield and high diastereo selectivity, which are useful in the preparation of cell-binding agent maytansinoid conjugates.

In some embodiments, X is hydrogen. In some embodiments, X is halo, for example, chloro. In some embodiments, Y is hydrogen. In some embodiments, Y is $C_1$-$C_6$ alkyl, for example, methyl. In some embodiments, $R^1$ is hydrogen. In some embodiments, $R^2$ is hydrogen. In some embodiments, $R^2$ is methyl. In some embodiments, $R^3$ is methyl. In some embodiments, $R^4$ is —OH.

In some embodiments, the compound of formula I is:

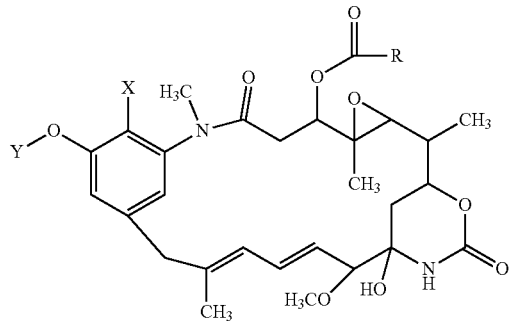

and the compound of formula I-A is:

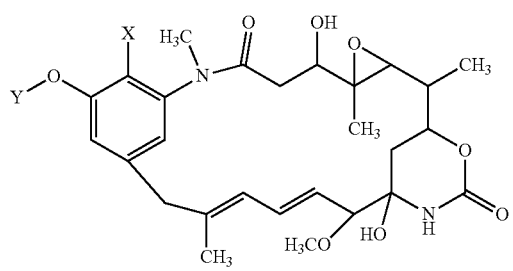

wherein X is hydrogen or Cl, Y is hydrogen or methyl, and R is as defined herein.

In some embodiments, the compound of Formula I-A is maytansinol.

In some embodiments, the present invention provides a method of preparing a compound of Formula III, or a salt thereof:

III

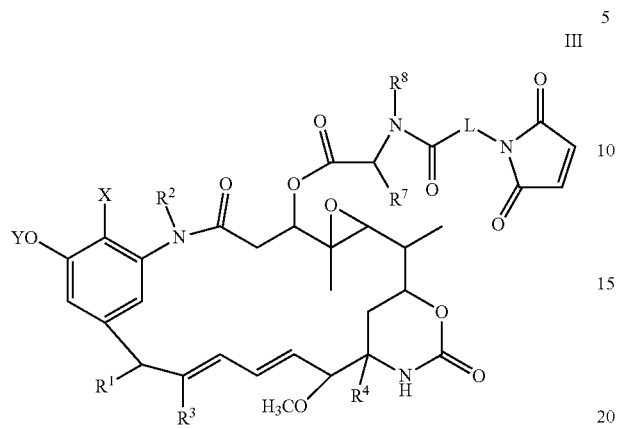

comprising contacting a compound of Formula III-A:

III-A with a carboxylic acid of Formula III-B

III-B in the presence of a coupling reagent, a rare earth metal-based or trifluoromethanesulfonate-based Lewis acid catalyst and a base to form the compound of Formula III, or a salt thereof; wherein X is hydrogen or halo;

Y is selected from the group consisting of hydrogen, $C_1$-$C_6$ alkyl, $C_3$-$C_6$ cycloalkyl, and —C(=O)$R^5$;

$R^1$ is selected from the group consisting of hydrogen, —OH, and —O$R^{17}$;

$R^2$ is hydrogen or $C_1$-$C_6$ alkyl;

$R^3$ is methyl, —CH$_2$OH, or CH$_2$O$R^{17}$;

$R^4$ is —OH, —O$R^{17}$ or —SH;

$R^5$ is $C_1$-$C_6$ alkyl or benzyl;

$R^{17}$ is a hydroxy protecting group;

$R^7$ is hydrogen, $C_1$-$C_6$ alkyl or an amino acid side chain;

$R^8$ is hydrogen or $C_{1-6}$ alkyl; and

L is selected from optionally substituted $C_1$-$C_{20}$ alkylene, $C_3$-$C_8$ cycloalkylene, and optionally substituted $C_1$-$C_{20}$ alkylene wherein one or more of the —CH$_2$— group is independently replaced with $C_3$-$C_8$ cycloalkylene, —O—, —S—, —C(O)—, —N$R^8$—, —C(=O)N$R^8$—, —N$R^8$C(=O)—, —SO$_2$N$R^8$—, or —N$R^8$SO$_2$—; wherein substituted $C_1$-$C_{20}$ alkylene is $C_1$-$C_{20}$ alkylene substituted with 1 to 4-SO$_3$H, —P(O)(OH)$_2$ or $R^{23}$, wherein each $R^{23}$ is independently $C_{1-6}$ alkyl optionally substituted with 1 or 2 substituents independently selected from the group consisting of SH, S—$C_{1-4}$ alkyl, —CON$R^{11}R^{11}$, and —N$R^{11}$Pr.

In some embodiments, the compound of Formula III is the isomer:

and the carboxylic acid of Formula III-B is the isomer IV-B:

IV-B

In some embodiments, the present invention provides a method of preparing a compound of Formula IV, or a salt thereof:

IV comprising contacting a compound of Formula IV-A:

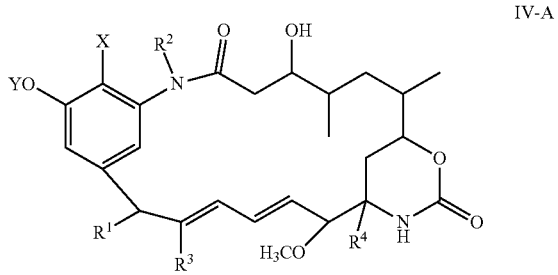

with a carboxylic acid of Formula IV-B

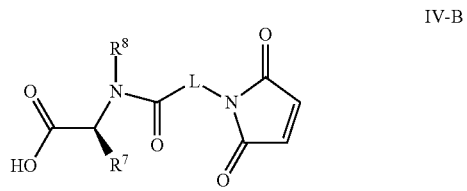

in the presence of a coupling reagent, a rare earth metal-based or trifluoromethanesulfonate-based Lewis acid catalyst and a base to form the compound of Formula IV, or a salt thereof; wherein
  X is hydrogen or halo;
  Y is selected from the group consisting of hydrogen, $C_1$-$C_6$ alkyl, $C_3$-$C_6$ cycloalkyl, and —C(=O)$R^5$;
  $R^1$ is selected from the group consisting of hydrogen, —OH, and —O$R^{17}$;
  $R^2$ is hydrogen or $C_1$-$C_6$ alkyl;
  $R^3$ is methyl, —$CH_2$OH, or $CH_2$O$R^{17}$;
  $R^4$ is —OH, or —O$R^{17}$ or —SH;
  $R^5$ is $C_1$-$C_6$ alkyl or benzyl;
  $R^{17}$ is a hydroxy protecting group;
  $R^7$ is hydrogen, $C_1$-$C_6$ alkyl or an amino acid side chain;
  $R^8$ is hydrogen or $C_{1-6}$ alkyl; and
  L is selected from optionally substituted $C_1$-$C_{20}$ alkylene, $C_3$-$C_8$ cycloalkylene, and optionally substituted $C_1$-$C_{20}$ alkylene wherein one or more of the —$CH_2$— group is independently replaced with $C_3$-$C_8$ cycloalkylene, —O—, —S—, —C(O)—, —$NR^8$—, —C(=O)$NR^8$—, —$NR^8$C(=O)—, —$SO_2NR^8$—, or —$NR^8SO_2$—; wherein substituted $C_1$-$C_{20}$ alkylene is $C_1$-$C_{20}$ alkylene substituted with 1 to 4-$SO_3$H, —P(O)(OH)$_2$ or $R^{23}$, wherein each $R^{23}$ is independently $C_{1-6}$ alkyl optionally substituted with 1 or 2 substituents independently selected from the group consisting of SH, S—$C_{1-4}$ alkyl, —CON$R^{11}R^{11}$, and —$NR^{11}$Pr.

In some embodiments, X is hydrogen. In some embodiments, X is chloro. In some embodiments, Y is hydrogen. In some embodiments, Y is $C_1$-$C_6$ alkyl, for example, methyl. In some embodiments, $R^1$ is hydrogen. In some embodiments, $R^1$ is —OC(=O)$R^5$ or —O$R^5$. In some embodiments, $R^2$ is methyl. In some embodiments, $R^3$ is methyl. In some embodiments, $R^3$ is $CH_2$OC(=O)$R^6$, wherein $R^6$ is $C_1$-$C_6$ alkyl, phenyl or benzyl. In some embodiments, $R^4$ is —OH. In some embodiments, $R^7$ is an amino acid side chain. In some embodiments, $R^7$ is methyl. In some embodiments, $R^8$ is methyl.

In some embodiments, L is unsubstituted $C_1$-$C_{20}$ alkylene. In some embodiments, L is substituted $C_1$-$C_{20}$ alkylene. In some embodiments, L is unsubstituted $C_1$-$C_{10}$ alkylene. In some embodiments, L is substituted $C_1$-$C_{10}$ alkylene. In some embodiments, L is —($CH_2$)$_5$—. In some embodiments, L is unsubstituted $C_1$-$C_{20}$ alkylene wherein one or two of the —$CH_2$— group is independently replaced with $C_3$-$C_8$ cycloalkylene, —O—, —S—, —$NR^8$—, —C(=O)$NR^8$—, —$NR^8$C(=O)—, —$SO_2NR^8$—, or —$NR^8SO_2$—. In some embodiments, L is substituted $C_1$-$C_{20}$ alkylene wherein one or two of the —$CH_2$— group is independently replaced with $C_3$-$C_8$ cycloalkylene, —O—, —S—, —$NR^8$—, —C(=O)$NR^8$—, —$NR^8$C(=O)—, —$SO_2NR^8$—, or —$NR^8SO_2$—.

In some embodiments, the present invention provides a method of preparing a compound of Formula V, or a salt thereof:

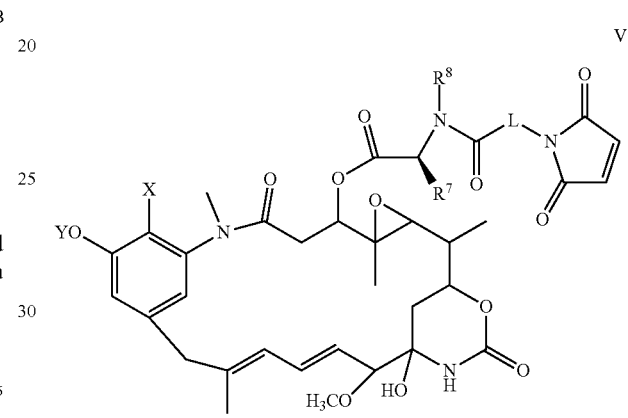

comprising contacting a compound of Formula V-A:

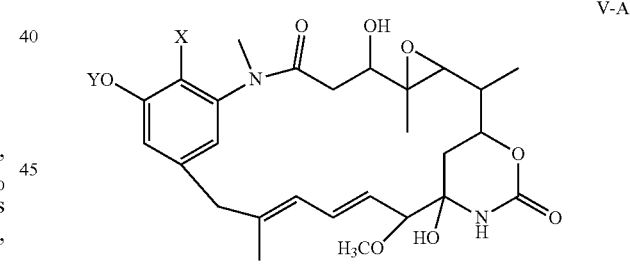

with a carboxylic acid of Formula IV-B

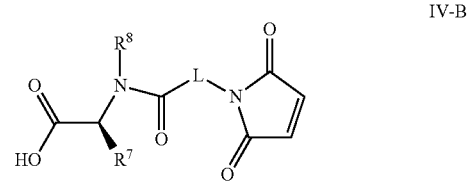

in the presence of a coupling reagent, a rare earth metal-based or trifluoromethanesulfonate-based Lewis acid catalyst and a base to form the compound of Formula V, or a salt thereof; wherein
  X is H or Cl;
  Y is H or methyl;

$R^7$ is hydrogen, $C_1$-$C_6$ alkyl or an amino acid side chain;

$R^8$ is hydrogen or $C_1$-$C_6$ alkyl; and

L is selected from optionally substituted $C_1$-$C_{20}$ alkylene, $C_3$-$C_8$ cycloalkylene, and optionally substituted $C_1$-$C_{20}$ alkylene wherein one or more of the —$CH_2$— group is independently replaced with $C_3$-$C_8$ cycloalkylene, —O—, —S—, —$NR^8$—, —C(=O)$NR^8$—, —$NR^8$C(=O)—, —$SO_2NR^8$—, or —$NR^8SO_2$—; wherein substituted $C_1$-$C_{20}$ alkylene is $C_1$-$C_{20}$ alkylene substituted with 1 to 4 —$SO_3H$, —$P(O)(OH)_2$ or $R^{23}$, wherein each $R^{23}$ is independently $C_{1-6}$ alkyl optionally substituted with 1 or 2 substituents independently selected from the group consisting of SH, S—$C_{1-4}$ alkyl, —$CONR^{11}R^{11}$, and —$NR^{11}Pr$.

In some embodiments, the present invention provides a method of preparing a compound of Formula VI, or a salt thereof:

VI

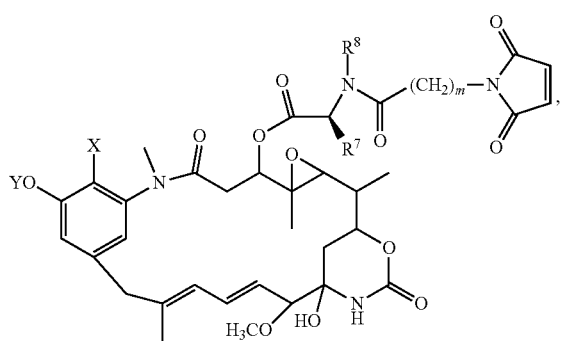

comprising contacting a compound of Formula V-A:

V-A

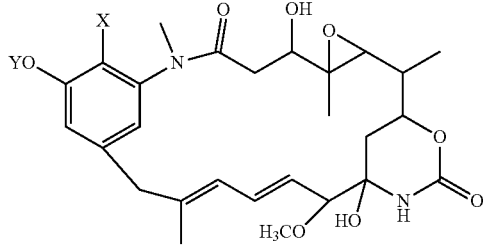

with a carboxylic acid of Formula VI-B

VI-B

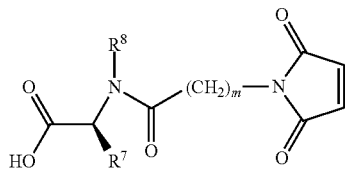

in the presence of a coupling reagent, a rare earth metal-based or trifluoromethanesulfonate-based Lewis acid catalyst and a base to form the compound of Formula VI, or a salt thereof;

wherein

X is H or Cl;

Y is H or methyl;

$R^7$ is hydrogen or an amino acid side chain;

$R^8$ is hydrogen or $C_1$-$C_6$ alkyl; and m is an integer of 1 to 20, preferably 1 to 10, more preferably 5 to 10.

In some embodiments, the present invention provides a method of preparing N'$_2$-deacetyl-N'$_2$-(6-maleimido-1-oxohexyl)maytansine, named batansine, or a salt thereof. Batansine is represented by Formula VII:

VII

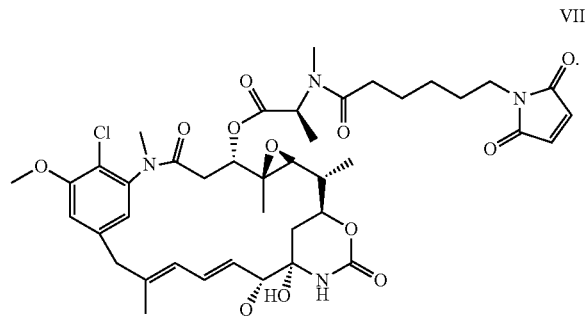

The method comprising contacting a compound of Formula VII-A:

VII-A

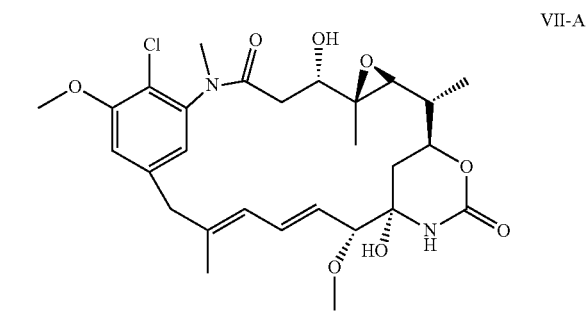

with a carboxylic acid of Formula VII-B

VII-B

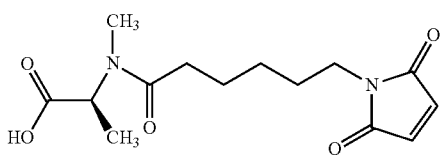

in the presence of a coupling reagent, a rare earth metal-based or trifluoromethanesulfonate-based Lewis acid catalyst and a base to form the compound of Formula VII or a salt thereof.

In some embodiments, the carboxylic acid of Formula III-B is prepared by a method comprising contacting a compound of Formula III-C

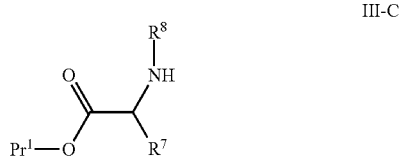

wherein $Pr^1$ is a carboxy protecting group such as $C_1$-$C_6$ alkyl or benzyl, with a compound of Formula III-D

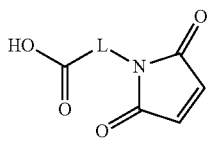

under coupling conditions to form the compound of Formula III-E:

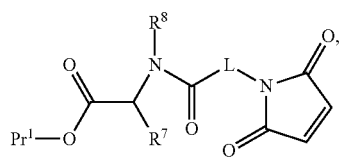

and deprotecting the compound of Formula III-E to form the compound of Formula III-B.

In some embodiments, the coupling conditions to form the compound of Formula III-B comprises an coupling reagent, such as, but not limited to, N-[(dimethylamino)-1H-1,2,3-triazolo[4,5-b]pyridine-1-ylmethylene]-N-methylmethanaminium hexafluorophosphate N-oxide (HATU), N-[(1H-benzotriazol-1-yl)(dimethylamino)methylene]-N-methylmethanaminium hexafluorophosphate N-oxide (HBTU), N-[(1H-benzotriazol-1-yl)(dimethylamino)methylene]-N-methylmethanaminium tetrafluoroborate N-oxide (TBTU), benzotriazole-1-yl-oxy-tris-(dimethylamino)-phosphonium hexafluorophosphate (BOP), benzotriazol-1-yl-N-oxy-tris(pyrrolidino)phosphonium hexafluorophosphate (PyBOP), 1-ethyl-3-(3-dimethylaminopropyl) carbodiimide (EDC) and N,N'-dicyclohexylcarbodiimide (DCC).

Carboxy protecting groups and methods of deprotection are known in the art, for example, those described in T. W. Greene and G. M. Wuts, *Protecting Groups in Organic Synthesis*, Third Edition, Wiley, New York, 1999, and references cited therein. Examples of carboxy protecting group including $C_1$-$C_6$ alkyl, such as methyl or ethyl, which can be deprotected by hydrolysis with a base (e.g., sodium hydroxide or potassium carbonate), t-butyl (t-Bu) which can be deprotected by acid hydrolysis (e.g., hydrochloric acid (HCl) or trifluoroacetic acid (TFA)), or benzyl which can be deprotected by hydrogenation with hydrogen in the presence of a catalyst, such as palladium.

The carboxylic acid of Formula IV-B, VI-B or VII-B can be prepared similarly using appropriate starting materials.

In some embodiments, the maytansinoid C-3 esters prepared by the methods described herein and the corresponding starting material maytansinoids are as in Table 1:

TABLE 1

| maytansinoid C-3 ester | maytansinoid |
|---|---|
| 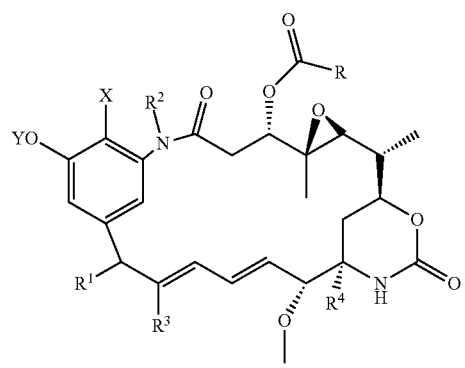 | 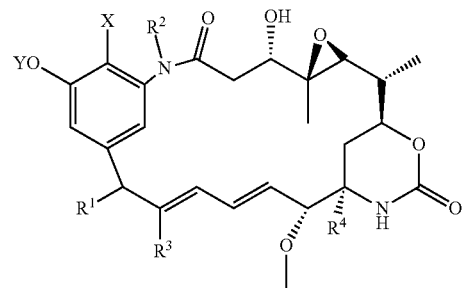 |

TABLE 1-continued
| maytansinoid C-3 ester | maytansinoid |
|---|---|
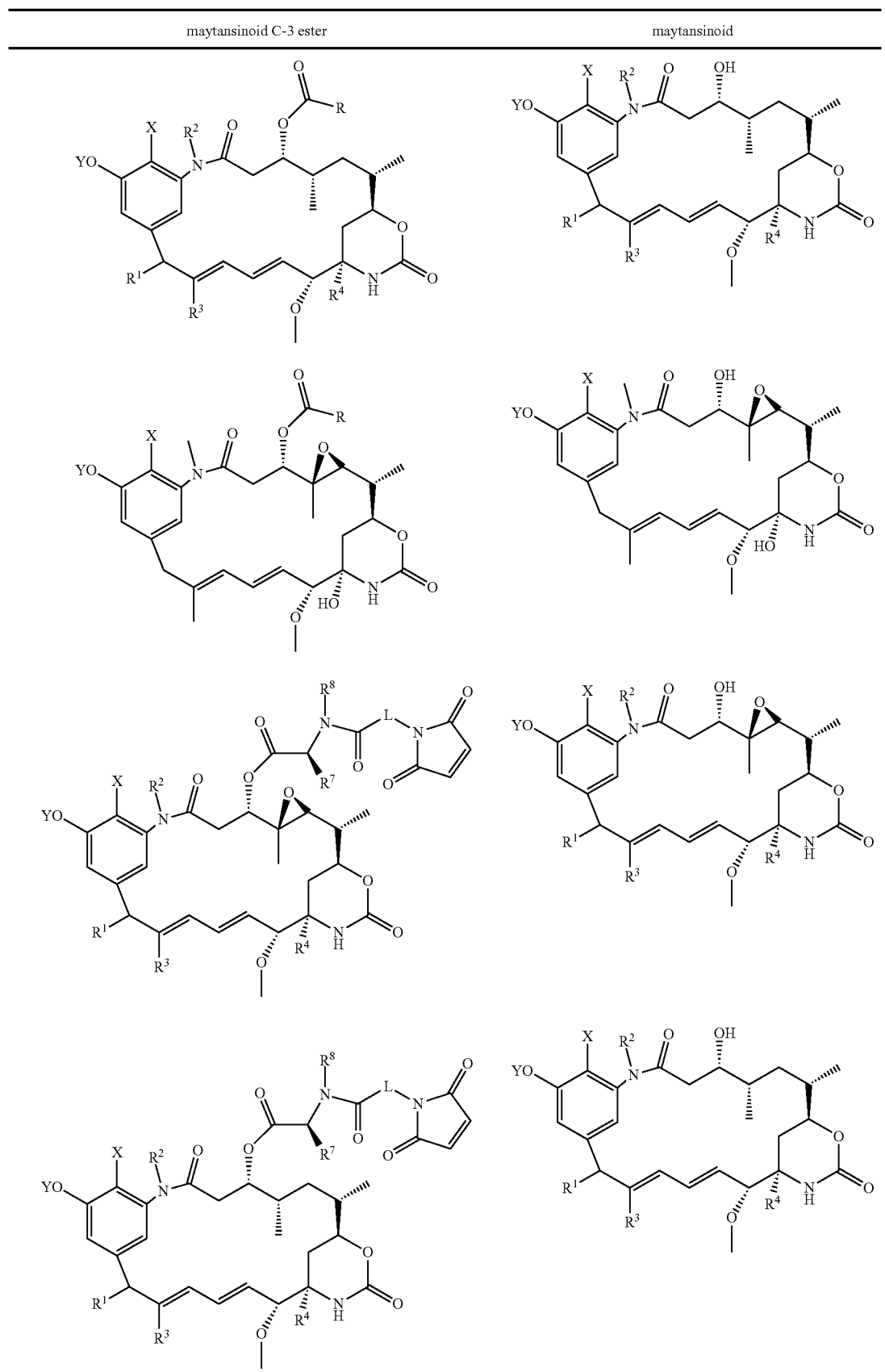

TABLE 1-continued

| maytansinoid C-3 ester | maytansinoid |
|---|---|

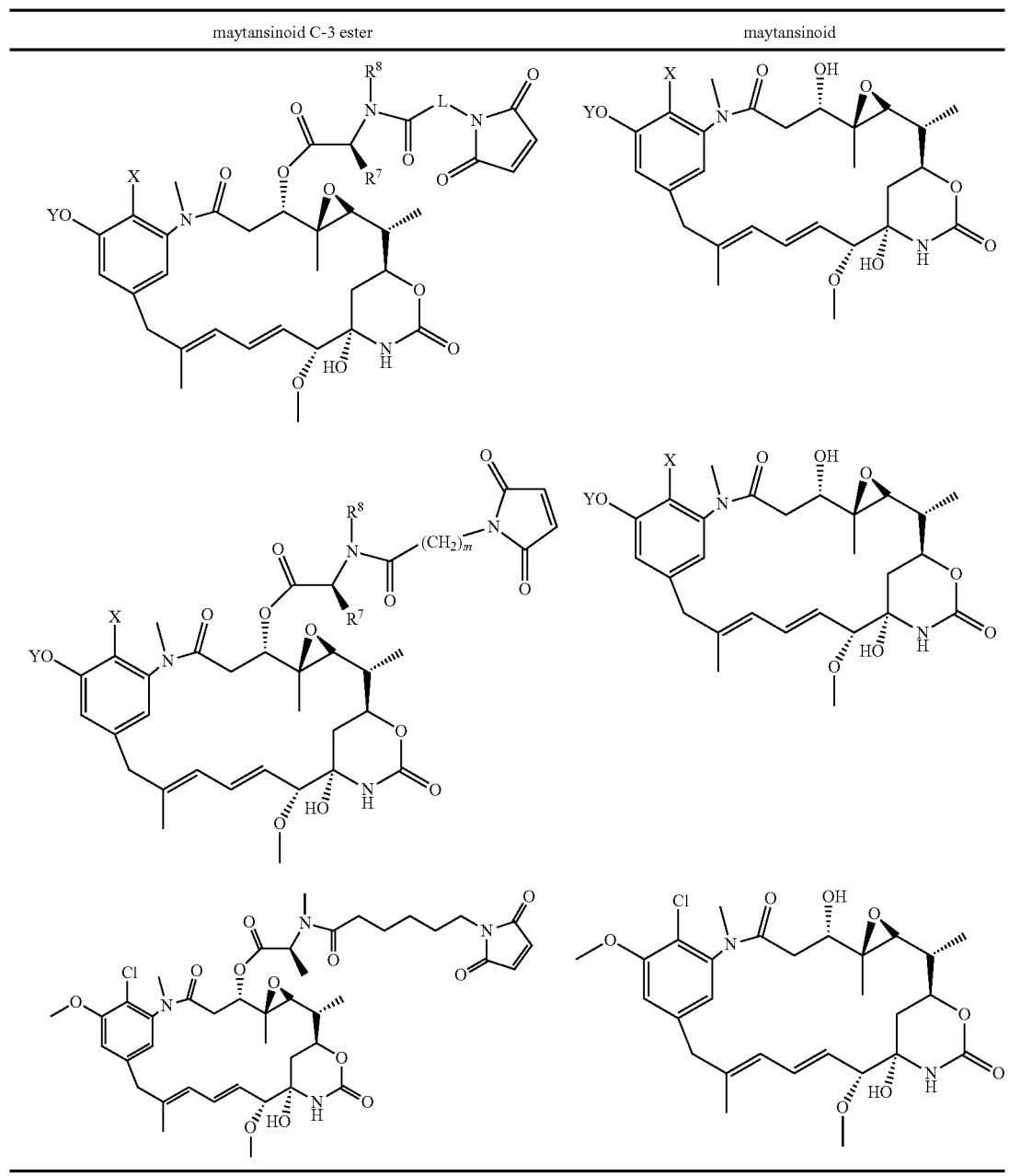

To ensure the expensive maytansinol is completely converted to the ester, at least one equivalent of the carboxylic acid can be used. Typically, the amount of the carboxylic acid used in the coupling reaction ranges from 3-20 equivalents per equivalent of maytansinol. The specific amount of carboxylic acid depends on the reaction condition applied.

The rare earth metal-based or trifluoromethanesulfonate-based Lewis acid catalyst used in the coupling reaction of maytansinoid is highly active Lewis acid catalyst. In some embodiments, the Lewis acid is a lanthanide, scandium or ytterbium compound. In some embodiments, the Lewis acid is a trifluoromethanesulfonate (triflate) compound. In some embodiments, the Lewis acid is a lanthanide trifluoromethanesulfonate (lanthanide triflate or $Ln(OTf)_3$). In some embodiments, the Lewis acid is scandium triflate (Sc $(OTf)_3$) or vanadyl triflate. In some embodiments, the Lewis acid is ytterbium triflate ($Yb(OTf)_3$). In some embodiments, the amount of the Lewis acid catalyst ranges from 0.1 to 1 equivalents or about 0.3-0.6 equivalents per equivalent of maytansinoid.

Suitable base used in the coupling reaction includes, but is not limited to, 4-dialkylaminopyridine such as DMAP or 4-pyrrolidinopyridine. The amount of base ranges from 1-5 equivalents or about 3 equivalents per equivalent of maytansinoid.

A variety of coupling reagents can be used for the coupling reaction. Examples of coupling reagents include, but not limited to, carbodiimide type reagents such as DCC (dicyclohexylcarbodiimide), DIC (diisopropylcarbodiimide), or EDC (1-ethyl-3-(3-dimethylaminopropyl)-dicarbodiimide). In some embodiments, at least 1 equivalent of the coupling reagent per equivalent of carboxylic acid is used. In some embodiments, the amount of the coupling reagent ranges from 1-2 equivalents per equivalent of carboxylic acid. In some embodiments, the amount of the coupling reagent is 1.0-1.2 equivalents per equivalent of carboxylic acid.

In some embodiments, the maytansinoid, the carboxylic acid, the Lewis acid catalyst and the base are stirred for a period of time, such as 10, 15, 20, 30 minutes, before the coupling reagent is added.

The progress of the coupling reaction can be monitored by conventional analytical methods, such as HPLC or TLC. Typically, a reaction is complete within a few hours depending on the reaction temperature and concentration of the reaction. In some embodiments, the reaction temperature is in the range of −10° C. to 20° C.

Suitable solvents for the reaction include, but are not limited to, halohydrocarbon such as methylene chloride ($CH_2Cl_2$) or chloroform ($CHCl_3$), ethers such tetrahydrofuran (THF), dimethoxyethane (DME), dioxane or a mixture thereof.

The product can be isolated by conventional methods, for example, insoluble material in the reaction mixture, such as $Sc(OTf)_3$, can be removed by filtration. The resulting filtrate can be washed with, for example, an acid such as hydrochloric acid and/or with a base such as sodium or potassium carbonate, sodium or potassium bicarbonate.

The product can be further purified by column chromatography on silica gel or alumina, preparative reversed phase or normal phase HPLC or recrystallization.

The present process enables clean and complete conversion of the starting material maytansinol, which has not been achieved by any other method already published. 100% conversion of the starting material maytansinol to the coupled maytansinol C-3 ester can be seen by HPLC. The yield of the isolated product depends on the carboxylic acid, reaction conditions, purification process employed, usually in the range of 50% to 90%.

In some embodiments, the carboxylic acid is a chiral amino acid derivative. Coupling of a maytansinoid, such as maytansinol, with a chiral amino acid derivative such as an N-methyl-L-alanine derivative, by $DCC/ZnCl_2$ typically results in formation of a mixture of 1:1 diastereomers. In some embodiments, the present process is able to provide the coupling product with stereoselectivity. The percent of diastereomeric excess (% de) of desired product L-diastereomer over unwanted D-epimer depends on the amino acid and the reaction conditions employed. In some embodiments, the % de is in the range of about 3% de to more than 99% de. In some embodiments, the % de is at least about 20%, about 30%, about 40%, about 50%, about 60% or about 70%. In some embodiments, the % de is at least about 80%. In some embodiments for direct coupling of maytansinol with Fmoc-N-Me-L-Ala, the % de of desired Fmoc-N-Me-L-Ala-MDC over the unwanted isomer was as low as 3%-9%. The two diastereomers can be separated by conventional methods, such as column chromatography, preparative reversed phase HPLC or preparative normal phase cyano-bonded HPLC column.

In some embodiments, the method is illustrated in Schemes 1-3.

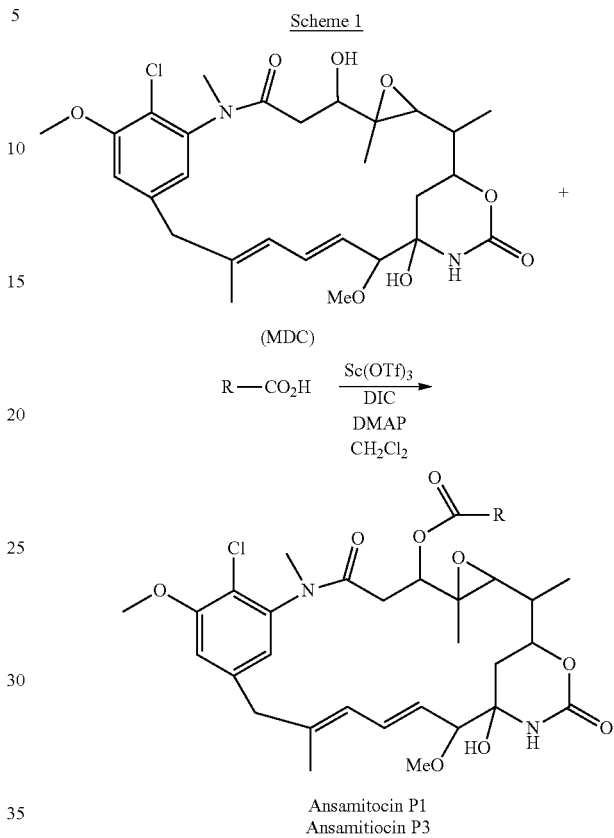

Scheme 1

(MDC)

$R—CO_2H$ $\xrightarrow[\text{DMAP}]{\text{Sc(OTf)}_3 \text{ DIC}}$ $CH_2Cl_2$

Ansamitocin P1
Ansamitocin P3

R = $CH_3$
$CH(CH_3)_2$
$(CH_2)_4CO_2CH_2CH_2SiMe_3$

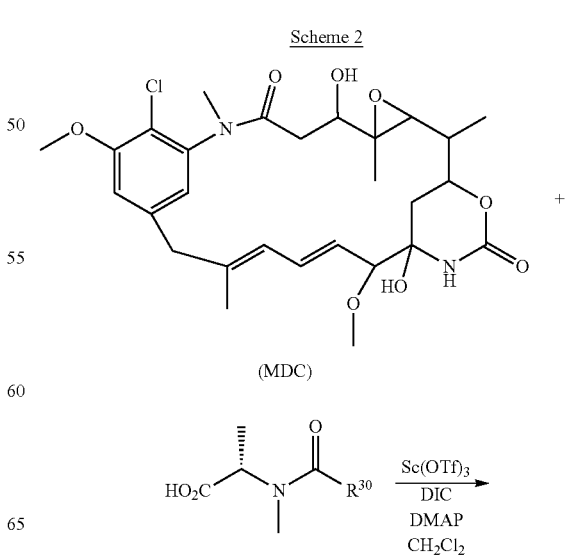

Scheme 2

(MDC)

$\xrightarrow[\text{DMAP}]{\text{Sc(OTf)}_3 \text{ DIC}}$ $CH_2Cl_2$

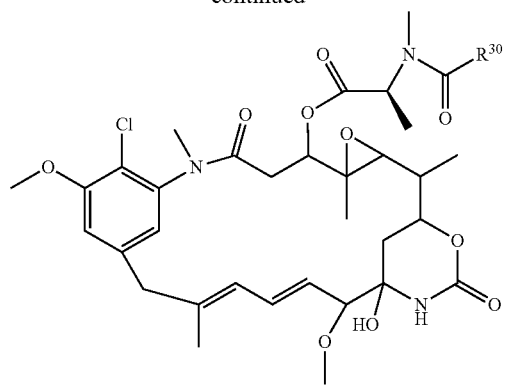

(L-)

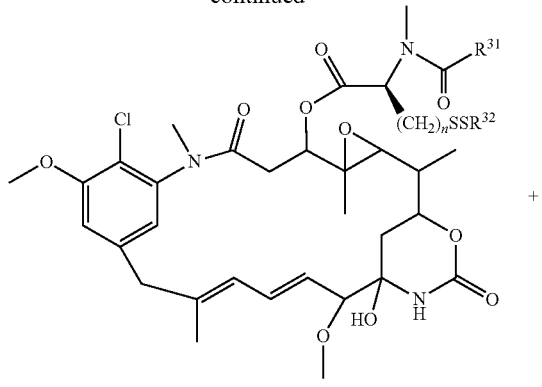

(L-)

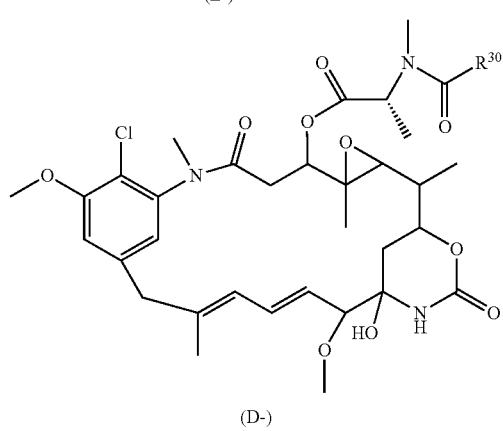

(D-)

R = CH₃
   CH₂CH₂SSCH₃
   CH₂CH₂C(CH₃)₂SSCH₃
   (CH₂)₄CO₂CH₂CH₂SiMe₃
$R^{30}$ = CH₃
   CH₂CH₂SSCH₃
   CH₂CH₂C(CH₃)₂SSCH₃
   (CH₂)₄CO₂CH₂CH₂SiMe₃
Maytansine
DM1-SMe
DM4-SMe Scheme 3

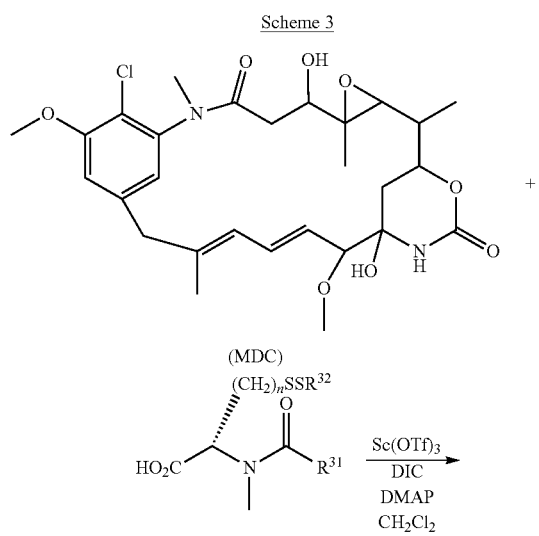

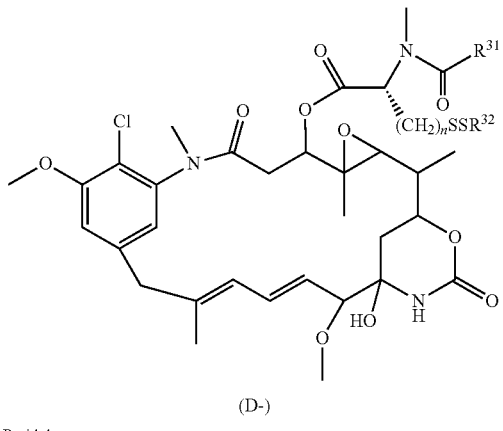

(D-)

$R^{32}$ = CH₃, Pyridyl
$R^{31}$ = $C_1$-$C_6$ alkyl, aryl
n = 1 or 2

In some embodiments, both $R^{31}$ and $R^{32}$ are methyl.

In some embodiments, the methods further comprises converting one or more of —$OR^{17}$ to —OH.

Compositions

In another aspect, provided is a composition comprising a maytansinoid, a carboxylic acid and a rare earth metal-based or trifluoromethanesulfonate-based Lewis acid. In some embodiments, the composition further comprises a base and a coupling reagent as described herein.

In some embodiments, the maytansinoid is a compound of any one of the maytansinoids described herein, for example, a compound of any one of Formula I-A, II-A, III-A, IV-A, V-A, VII-A, and those in Table 1. In some embodiments, the maytansinoid is maytansinol. In some embodiments, the carboxylic acid is any one of the carboxylic acids described herein, for example, a compound of the formula R—COOH as described herein, or a compound of any one of Formula III-B, IV-B, VI-B, and VII-B. In some embodiments, the rare earth metal-based or trifluoromethanesulfonate-based Lewis acid is as described herein, for example, a lanthanide compound, a scandium compound or a trifluoromethanesulfonate (triflate) compound. In some embodiments, the Lewis acid is a lanthanide trifluoromethanesulfonate. In some embodiments, the Lewis acid is scandium triflate.

In some embodiments, the composition further comprises a suitable solvent. In some embodiments, the solvent is halohydrocarbon such as methylene chloride ($CH_2Cl_2$) or chloroform ($CHCl_3$), ethers such as tetrahydrofuran (THF), dimethoxyethane (DME), dioxane or a mixture thereof.

Such compositions are useful in preparing maytansinoid C-3 esters.

Use of the Maytansinoid C-3 Ester Prepared by the Present Process

Direct coupling of maytansinol with Fmoc-N-methyl-L-alanine (Fmoc-N-Me-L-Ala) leading to Fmoc-N-Me-L-Ala-MDC were studied. Many coupling reagents and catalysts including: DCC/ZnCl$_2$, DCC/DMAP, Boc$_2$O/pyridine/DMAP, 2-PDS/PPh$_3$, 1,1'-carbonylbis(3-Methylimidazolium)triflate (CBMIT) are examined, but none of them resulted in any desired product. Conversion of Fmoc-N-methyl-L-alanine to its acyl chloride and then reaction with maytansinol under a variety of bases such as Et$_3$N, DIEA and DMAP failed too. However, under the present process of this invention, direct coupling of maytansinol with Fmoc-N-methyl-L-alanine gave Fmoc-N-methyl-alanine-MDC in excellent yield (100% conversion and about 90% isolated yield) in a few hours. The percent of diastereomeric excess (% de) of desired product L-Ala over unwanted D-Ala was low (about 3~9%).

The maytansinoid C-3 esters, such as Fmoc-N-Me-Ala-MDC, are useful as intermediates for the preparation of maytansinoid conjugates. For example, the protecting group of Fmoc-N-Me-Ala-MDC can be removed to provide the free amino group N-Me-Ala-MDC in excellent yield, which can be coupled with another carboxylic acid. Although N-Me-Ala-MDC can also be prepared by deprotection of Boc-N-Me-Ala-MDC, the yield for coupling of maytansinol with Boc-N-methyl-L-alanine to give Boc-N-Me-Ala-MDC is very very low (1.4%) and the yield for Boc deprotection of Boc-N-Me-Ala-MDC is very low too (12.1%) (EP 0021173). Furthermore, almost no coupled Boc-N-Me-Ala-MDC can be found under the reaction conditions we tried. Deprotection of Fmoc group of Fmoc-N-Me-Ala-MDC can be done under various conditions, such as in a solution comprising a base and a solvent. In some embodiments, the solvent is selected from the group consisting of CH$_3$CN, DMF, CH$_2$Cl$_2$, THF and MeOH, and a mixture thereof. In some embodiments, the base is selected from the group consisting of piperidine, morpholine and diethylamine (Et$_2$NH) and mixture thereof. In some embodiments, deprotection of diastereo pure Fmoc-N-Me-L-Ala-MDC under the above conditions gives diastereo pure N-Me-L-Ala-MDC. In some embodiments, the reaction is clean as monitored by HPLC. The resulting crude N-Me-Ala-MDC may be purified, for example using HPLC, or used directly in the next step.

A variety of carboxylic acid can be used to couple with N-Me-Ala-MDC. For example, an active ester form such as N-hydroxysuccinimide ester of the carboxylic acid may be used in the coupling reaction with N-Me-Ala-MDC. Alternatively, direct coupling of N-Me-Ala-MDC with carboxylic acid can be performed with a suitable coupling reagent such as, but not limited to, HATU, HBTU, TBTU, BOP, PyBOP, EDC and DCC.

In some embodiments, provided is a method of preparing a compound of Formula X

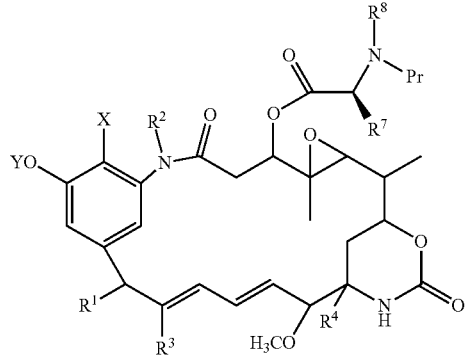

comprising deprotection of a compound of Formula X-A:

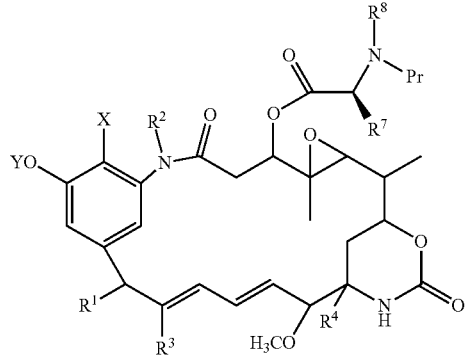

wherein

X is hydrogen or halo;

Y is selected from the group consisting of hydrogen, C$_1$-C$_6$ alkyl, C$_3$-C$_6$ cycloalkyl, and —C(=O)R$^5$;

R$^1$ is selected from the group consisting of hydrogen, —OH, and —OR$^{17}$;

R$^2$ is hydrogen or C$_1$-C$_6$ alkyl;

R$^3$ is methyl, —CH$_2$OH, or —CH$_2$OR$^{17}$;

R$^4$ is —OH, —OR$^{17}$ or —SH;

R$^5$ is C$_1$-C$_6$ alkyl or benzyl;

R$^{17}$ is a hydroxy protecting group;

R$^7$ is hydrogen, C$_1$-C$_6$ alkyl or an amino acid side chain;

R$^8$ is hydrogen or C$_{1-6}$ alkyl; and

Pr is an amino protecting group, such as Boc or Fmoc.

In some embodiments Pr is Fmoc and the deprotection is conducted under conditions comprising a base, such as diethylamine, piperidine, or morpholine.

In another aspect, provided is a method of preparing a compound of Formula XI,

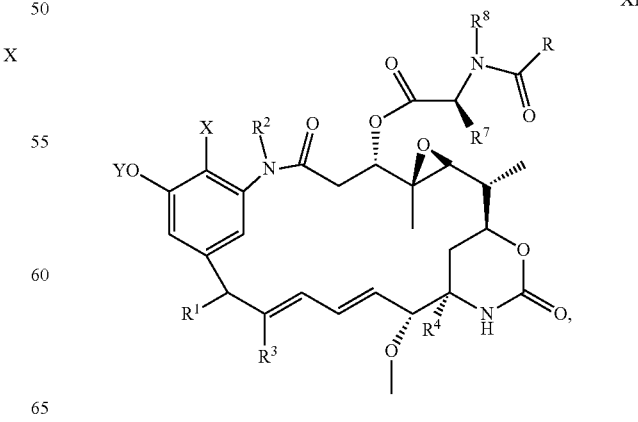

or a salt thereof, comprising contacting a compound of Formula X:

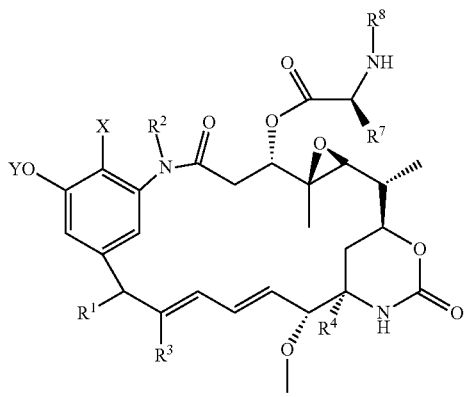

with a carboxylic acid of Formula III-G

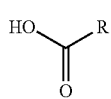

in the presence of a coupling reagent, or
with its active ester to form the compound of Formula XI, or a salt thereof;
wherein
  X is hydrogen or halo;
  Y is selected from the group consisting of hydrogen, $C_1$-$C_6$ alkyl, $C_3$-$C_6$ cycloalkyl, and —C(=O)$R^5$;
  $R^1$ is selected from the group consisting of hydrogen, —OH, and —O$R^{17}$;
  $R^2$ is hydrogen or $C_1$-$C_6$ alkyl;
  $R^3$ is methyl, —CH$_2$OH, or —CH$_2$O$R^{17}$;
  $R^4$ is —OH, —O$R^{17}$ or —SH;
  $R^5$ is $C_1$-$C_6$ alkyl or benzyl;
  $R^{17}$ is a hydroxy protecting group;
  $R^7$ is hydrogen, $C_1$-$C_6$ alkyl or an amino acid side chain;
  $R^8$ is hydrogen or $C_{1-6}$ alkyl; and
  R is hydrogen, alkyl, aryl, cycloalkyl, cycloalkenyl, heteroaryl.

In another aspect, provided is a method of preparing a compound of Formula XIII,

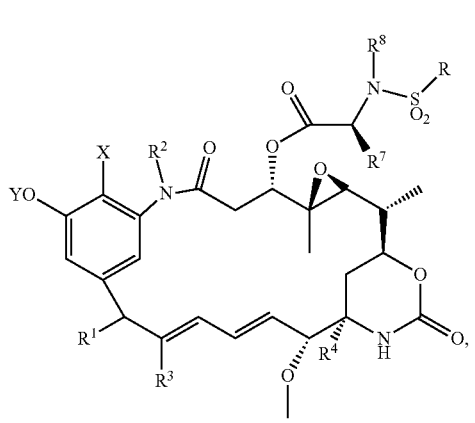

or a salt thereof, comprising contacting a compound of Formula X:

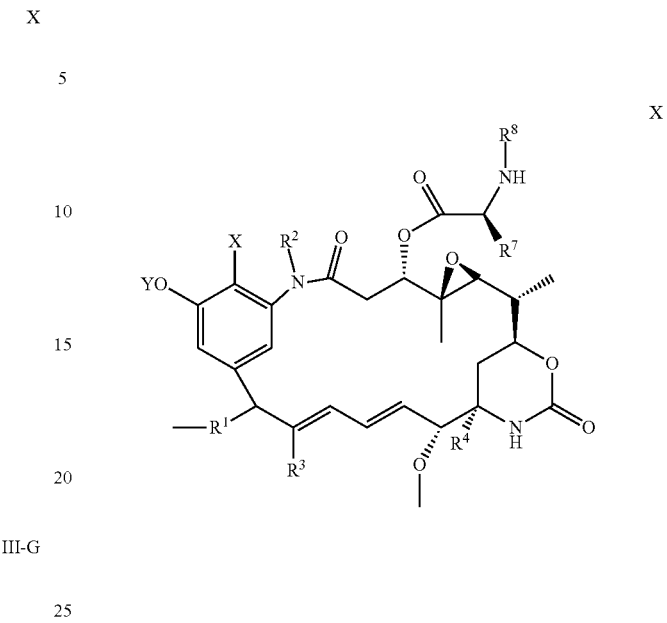

with RSO$_2$Cl to form the compound of Formula XIII, or a salt thereof;
wherein
  X is hydrogen or halo;
  Y is selected from the group consisting of hydrogen, $C_1$-$C_6$ alkyl, $C_3$-$C_6$ cycloalkyl, and —C(=O)$R^5$;
  $R^1$ is selected from the group consisting of hydrogen, —OH, and —O$R^{17}$;
  $R^2$ is hydrogen or $C_1$-$C_6$ alkyl;
  $R^3$ is methyl, —CH$_2$OH, or —CH$_2$O$R^{17}$;
  $R^4$ is —OH, —O$R^{17}$ or —SH;
  $R^5$ is $C_1$-$C_6$ alkyl or benzyl;
  $R^{17}$ is a hydroxy protecting group;
  $R^7$ is hydrogen, $C_1$-$C_6$ alkyl or an amino acid side chain;
  $R^8$ is hydrogen or $C_{1-6}$ alkyl; and
  R is hydrogen, alkyl, aryl, cycloalkyl, cycloalkenyl, heteroaryl.

In some embodiments, the contacting of the compound of Formula X with the carboxylic acid of Formula III-G, its active ester, or RSO$_2$Cl is in the presence of a base, such as triethylamine, DIEA, or pyridine, and a solvent such as halohydrocarbon such as methylene chloride (CH$_2$Cl$_2$) or chloroform (CHCl$_3$), ethers such tetrahydrofuran (THF), dimethoxyethane (DME), dioxane or a mixture thereof.

In some embodiments, the active ester is $R^{18}$OC(O)R, wherein $R^{18}$ is halo or —O—$R^{19}$, wherein $R^{19}$ is selected from the group consisting of —CH=CH$_2$, -cyanomethyl, -pyridyl, halo or nitro substituted phenyl (e.g., 4-nitrophenyl, 2,4,6-trichlorophenyl, pentachlorophenyl, pentafluorophenyl), phthalimido, succinimido, N-benxotriazolyl.

In another aspect, provided is a method of preparing a compound of Formula XII,

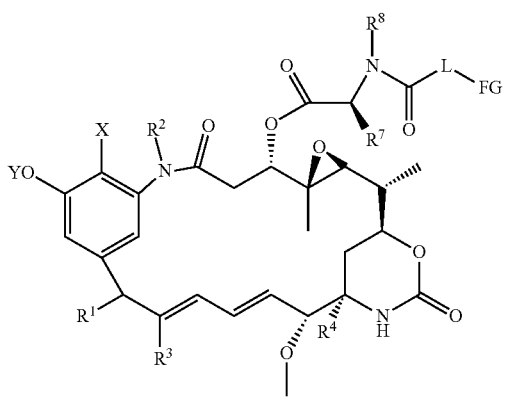

or a salt thereof, comprising contacting a compound of Formula X:

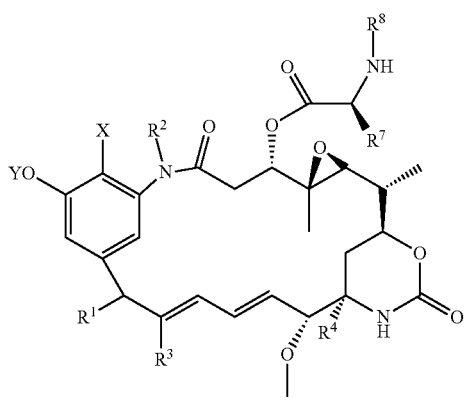

with a carboxylic acid of Formula III-H

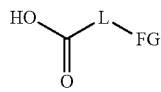

in the presence of a coupling reagent or directly with its active ester to form the compound of Formula XII, or a salt thereof; wherein
- X is hydrogen or halo;
- Y is selected from the group consisting of hydrogen, $C_1$-$C_6$ alkyl, $C_3$-$C_6$ cycloalkyl, and —C(=O)$R^5$;
- $R^1$ is selected from the group consisting of hydrogen, —OH, and —O$R^{17}$;
- $R^2$ is hydrogen or $C_1$-$C_6$ alkyl;
- $R^3$ is methyl, —CH$_2$OH, or —CH$_2$O$R^{17}$;
- $R^4$ is —OH, —O$R^{17}$ or —SH;
- $R^5$ is $C_1$-$C_6$ alkyl or benzyl;
- $R^{17}$ is a hydroxy protecting group;
- $R^7$ is hydrogen, $C_1$-$C_6$ alkyl or an amino acid side chain;
- $R^8$ is hydrogen or $C_{1-6}$ alkyl; and
- L is selected from optionally substituted $C_1$-$C_{20}$ alkylene, $C_3$-$C_8$ cycloalkylene, and optionally substituted $C_1$-$C_{20}$ alkylene wherein one or more of the —CH$_2$— group is independently replaced with $C_3$-$C_8$ cycloalkylene, —O—, —S—, —C(O)—, —N$R^{10}$—, —C(=O)N$R^{10}$—, —N$R^{10}$C(=O)—, —SO$_2$N$R^{10}$—, or —N$R^{10}$SO$_2$—;
- substituted $C_1$-$C_{20}$ alkylene is $C_1$-$C_{20}$ alkylene substituted with 1 to 4-SO$_3$H, —P(O)(OH)$_2$ or $R^{23}$, wherein each $R^{23}$ is independently $C_{1-6}$ alkyl optionally substituted with 1 or 2 substituents independently selected from the group consisting of SH, S—$C_{1-4}$ alkyl, —CON$R^{11}R^{11}$, and —N$R^{11}$Pr;
- FG is independently selected from the group consisting of —N$R^{11}$Pr, —N$R^{11}$COCH$_2$Br, —COO$R^{12}$, —CON$R^{11}R^{11}$, —N$R^{11}$CO$R^{13}$,

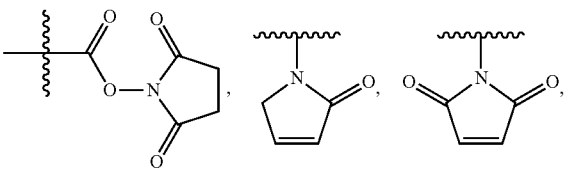

—S—S—$R^{13}$, —Si($R^{13}$)$_3$, alkyl, aryl, cycloalkyl, cycloalkenyl, heteroaryl, and heterocyclic;
- each $R^{10}$ or $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo;
- Pr is an amino protecting group;
- $R^{12}$ is $C_1$-$C_6$ alkyl, or benzyl; and
- each $R^{13}$ is independently selected from the group consisting of alkyl, aryl, cycloalkyl, heteroaryl, and heterocyclic.

In some embodiments, the active ester is $R^{18}$OC(O)-L-FG, wherein $R^{18}$ is halo or —O—$R^{19}$, wherein $R^{19}$ is selected from the group consisting of —CH=CH$_2$, -cyanomethyl, -pyridyl, halo or nitro substituted phenyl (e.g., 4-nitrophenyl, 2,4,6-trichlorophenyl, pentachlorophenyl, pentafluorophenyl), phthalimido, succinimido, N-benxotriazolyl.

In another aspect, provided is a method of preparing a compound of Formula III, or a salt thereof:

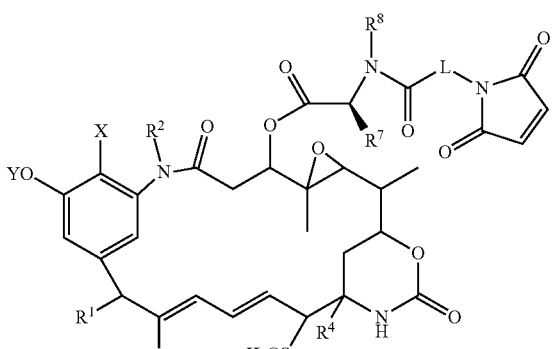

comprising contacting a compound of Formula X:

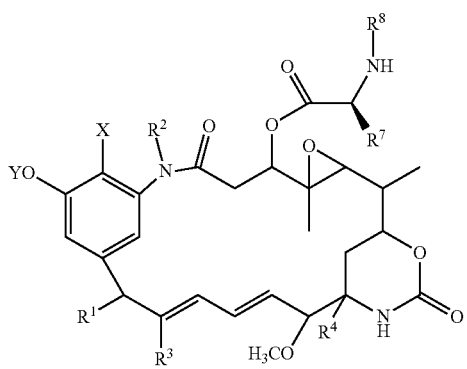

with a carboxylic acid of Formula III-C

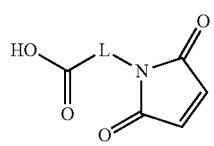

in the presence of a coupling reagent; or
with an active ester of the acid which is a compound of Formula III-F

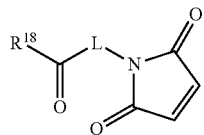

wherein $R^{18}$ is halo or —O—$R^{19}$, wherein $R^{19}$ is selected from the group consisting of —CH=CH$_2$, -cyanomethyl, -pyridyl, halo or nitro substituted phenyl (e.g., 4-nitrophenyl, 2,4,6-trichlorophenyl, pentachlorophenyl, pentafluorophenyl), phthalimido, succinimido, N-benxotriazolyl, to form the compound of Formula III, or a salt thereof;
wherein
  X is hydrogen or halo;
  Y is selected from the group consisting of hydrogen, $C_1$-$C_6$ alkyl, $C_3$-$C_6$ cycloalkyl, and —C(=O)$R^5$;
  $R^1$ is selected from the group consisting of hydrogen, —OH, and —OR$^{17}$;
  $R^2$ is hydrogen or $C_1$-$C_6$ alkyl;
  $R^3$ is methyl, —CH$_2$OH, or —CH$_2$OR$^{17}$;
  $R^4$ is —OH, —OR$^{17}$ or —SH;
  $R^5$ is $C_1$-$C_6$ alkyl or benzyl;
  $R^{17}$ is a hydroxy protecting group;
  $R^7$ is hydrogen, $C_1$-$C_6$ alkyl or an amino acid side chain;
  $R^8$ is hydrogen or $C_{1-6}$ alkyl; and
  L is selected from optionally substituted $C_1$-$C_{20}$ alkylene, $C_3$-$C_8$ cycloalkylene, and optionally substituted $C_1$-$C_{20}$ alkylene wherein one or more of the —CH$_2$— group is independently replaced with $C_3$-$C_8$ cycloalkylene, —O—, —S—, —C(O)—, —NR$^8$—, —C(=O)NR$^8$—, —NR$^8$C(=O)—, —SO$_2$NR$^8$—, or —NR$^8$SO$_2$—;
wherein substituted $C_1$-$C_{20}$ alkylene is $C_1$-$C_{20}$ alkylene substituted with 1 to 4-SO$_3$H, —P(O)(OH)$_2$ or $R^{23}$, wherein each $R^{23}$ is independently $C_{1-6}$ alkyl optionally substituted with 1 or 2 substituents independently selected from the group consisting of SH, S—$C_{1-4}$ alkyl, —CONR$^{11}$R$^{11}$, and —NR$^{11}$Pr.

In another aspect, provided is a method of preparing a compound of Formula XIV,

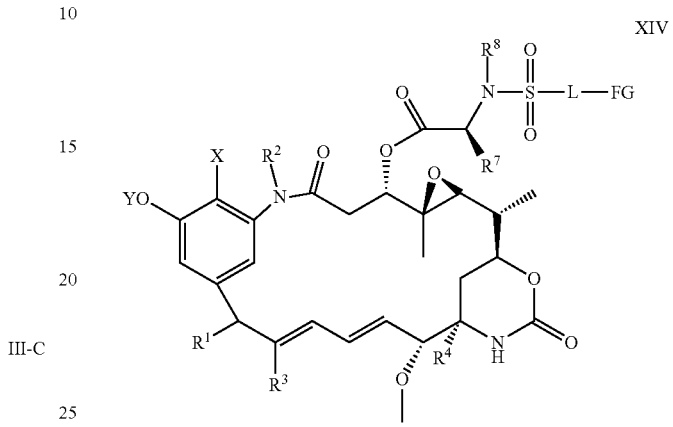

or a salt thereof, comprising contacting a compound of Formula X:

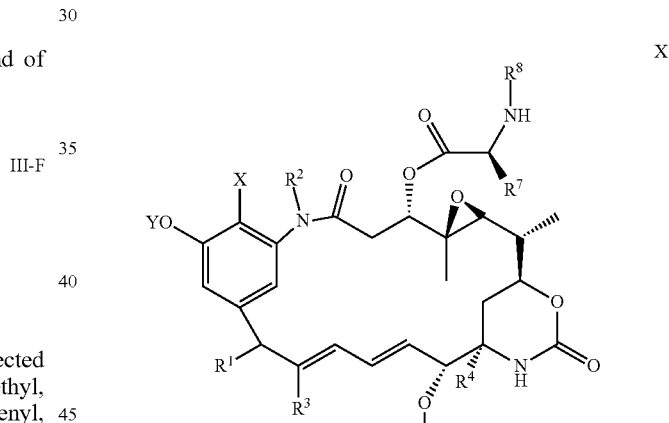

with a sulfonyl chloride of Formula XIV-A

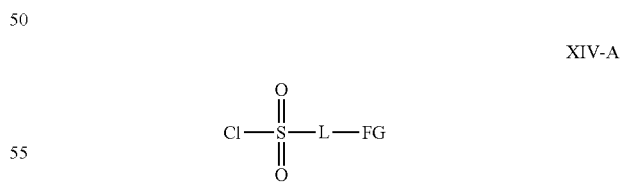

in the presence of a base to form the compound of Formula XIV, or a salt thereof;
wherein
  X is hydrogen or halo;
  Y is selected from the group consisting of hydrogen, $C_1$-$C_6$ alkyl, $C_3$-$C_6$ cycloalkyl, and —C(=O)$R^5$;
  $R^1$ is selected from the group consisting of hydrogen, —OH, and —OR$^{17}$;
  $R^2$ is hydrogen or $C_1$-$C_6$ alkyl;
  $R^3$ is methyl, —CH$_2$OH, or —CH$_2$OR$^{17}$;

$R^4$ is —OH, —OR$^{17}$ or —SH;
$R^5$ is $C_1$-$C_6$ alkyl or benzyl;
$R^{17}$ is a hydroxy protecting group;
$R^7$ is hydrogen, $C_1$-$C_6$ alkyl or an amino acid side chain;
$R^8$ is hydrogen or $C_{1-6}$ alkyl; and
L is selected from optionally substituted $C_1$-$C_{20}$ alkylene, $C_3$-$C_8$ cycloalkylene, and optionally substituted $C_1$-$C_{20}$ alkylene wherein one or more of the —CH$_2$— group is independently replaced with $C_3$-$C_8$ cycloalkylene, —O—, —S—, —C(O)—, —NR$^{10}$—, —C(=O)NR$^{10}$—, —NR$^{10}$C(=O)—, —SO$_2$NR$^{10}$—, or —NR$^{10}$SO$_2$—;
substituted $C_1$-$C_{20}$ alkylene is $C_1$-$C_{20}$ alkylene substituted with 1 to 4-SO$_3$H, —P(O)(OH)$_2$ or R$^{23}$, wherein each R$^{23}$ is independently $C_{1-6}$ alkyl optionally substituted with 1 or 2 substituents independently selected from the group consisting of SH, S—$C_{1-4}$ alkyl, —CONR$^{11}$R$^{11}$, and —NR$^{11}$Pr;
FG is independently selected from the group consisting of —NR$^{11}$Pr, —NR$^{11}$COCH$_2$Br, —COOR$^{12}$, CONR$^{11}$R$^{11}$, —NR$^{11}$COR$^{13}$,

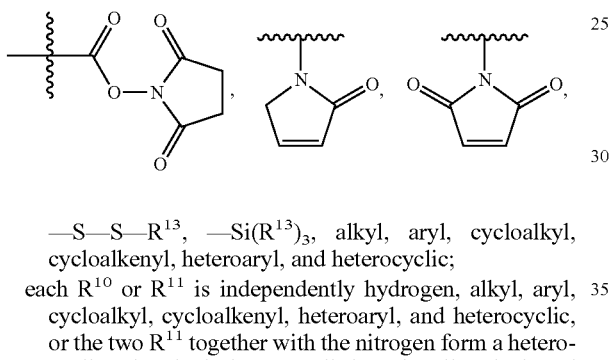

—S—S—R$^{13}$, —Si(R$^{13}$)$_3$, alkyl, aryl, cycloalkyl, cycloalkenyl, heteroaryl, and heterocyclic;
each $R^{10}$ or $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo;
Pr is an amino protecting group;
$R^{12}$ is $C_1$-$C_6$ alkyl, or benzyl; and
each $R^{13}$ is independently selected from the group consisting of alkyl, aryl, cycloalkyl, heteroaryl, and heterocyclic.

In another aspect, provided is a method of preparing a compound of Formula XV, or a salt thereof:

XV

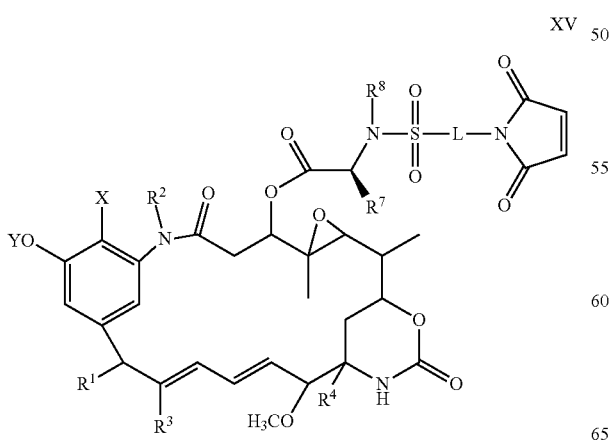

comprising contacting a compound of Formula X:

X

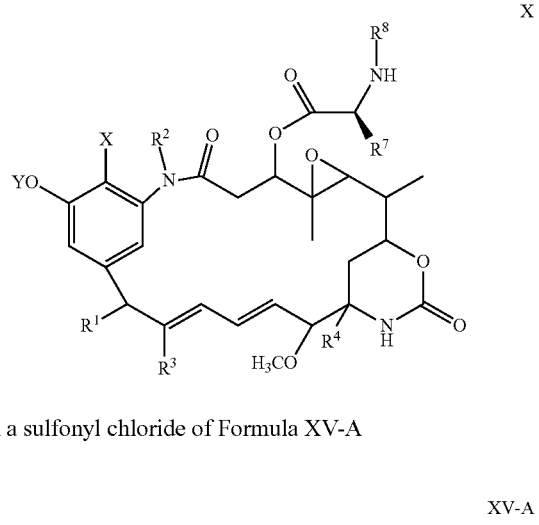

with a sulfonyl chloride of Formula XV-A

XV-A $$Cl-\overset{O}{\underset{O}{S}}-L-N\text{(maleimide)}$$

in the presence of a base to form the compound of Formula XV, or a salt thereof;
wherein
X is hydrogen or halo;
Y is selected from the group consisting of hydrogen, $C_1$-$C_6$ alkyl, $C_3$-$C_6$ cycloalkyl, and —C(=O)R$^5$;
$R^1$ is selected from the group consisting of hydrogen, —OH, and —OR$^{17}$;
$R^2$ is hydrogen or $C_1$-$C_6$ alkyl;
$R^3$ is methyl, —CH$_2$OH, or —CH$_2$OR$^{17}$;
$R^4$ is —OH, —OR$^{17}$ or —SH;
$R^5$ is $C_1$-$C_6$ alkyl or benzyl;
$R^{17}$ is a hydroxy protecting group;
$R^7$ is hydrogen, $C_1$-$C_6$ alkyl or an amino acid side chain;
$R^8$ is hydrogen or $C_{1-6}$ alkyl; and
L is selected from optionally substituted $C_1$-$C_{20}$ alkylene, $C_3$-$C_8$ cycloalkylene, and optionally substituted $C_1$-$C_{20}$ alkylene wherein one or more of the —CH$_2$— group is independently replaced with $C_3$-$C_8$ cycloalkylene, —O—, —S—, —C(O)—, —NR$^8$—, —C(=O)NR$^8$—, —NR$^8$C(=O)—, —SO$_2$NR$^8$—, or —NR$^8$SO$_2$—;
wherein substituted $C_1$-$C_{20}$ alkylene is $C_1$-$C_{20}$ alkylene substituted with 1 to 4-SO$_3$H, —P(O)(OH)$_2$ or R$^{23}$, wherein each R$^{23}$ is independently $C_{1-6}$ alkyl optionally substituted with 1 or 2 substituents independently selected from the group consisting of SH, S—$C_{1-4}$ alkyl, —CONR$^{11}$R$^{11}$, and —NR$^{11}$Pr.

In some embodiments, X is hydrogen. In some embodiments, X is chloro. In some embodiments, Y is hydrogen. In some embodiments, Y is $C_1$-$C_6$ alkyl, for example, methyl. In some embodiments, $R^1$ is hydrogen. In some embodiments, $R^1$ is —OC(=O)R$^5$ or —OR$^5$. In some embodiments, $R^2$ is methyl. In some embodiments, $R^3$ is methyl. In some embodiments, $R^3$ is CH$_2$C(=O)R$^6$, wherein $R^6$ is $C_1$-$C_6$ alkyl, phenyl or benzyl. In some embodiments, $R^4$ is —OH. In some embodiments, $R^7$ is an amino acid side chain. In some embodiments, $R^7$ is methyl. In some embodiments, $R^8$ is methyl.

In some embodiments, L is unsubstituted $C_1$-$C_{20}$ alkylene. In some embodiments, L is substituted $C_1$-$C_{20}$ alkylene. In some embodiments, L is unsubstituted $C_1$-$C_{10}$ alkylene. In some embodiments, L is substituted $C_1$-$C_{10}$ alkylene. In some embodiments, L is —(CH$_2$)$_5$—. In some embodiments, L is unsubstituted $C_1$-$C_{20}$ alkylene wherein one or two of the —CH$_2$— group is independently replaced with $C_3$-$C_8$ cycloalkylene, —O—, —S—, —NR$^8$—, —C(=O)NR$^8$—, —NR$^8$C(=O)—, —SO$_2$NR$^8$—, or —NR$^8$SO$_2$—. In some embodiments, L is substituted $C_1$-$C_{20}$ alkylene wherein one or two of the —CH$_2$— group is independently replaced with $C_3$-$C_8$ cycloalkylene, —O—, —S—, —NR$^8$—, —C(=O)NR$^8$—, —NR$^8$C(=O)—, —SO$_2$NR$^8$—, or —NR$^8$SO$_2$—.

In some embodiments, R is

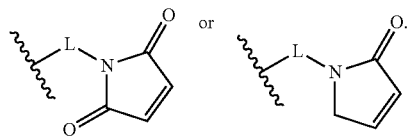

Examples of the use of the N-Me-Ala-MDC are illustrated in Scheme 4 and Examples 12-17.

Scheme 4

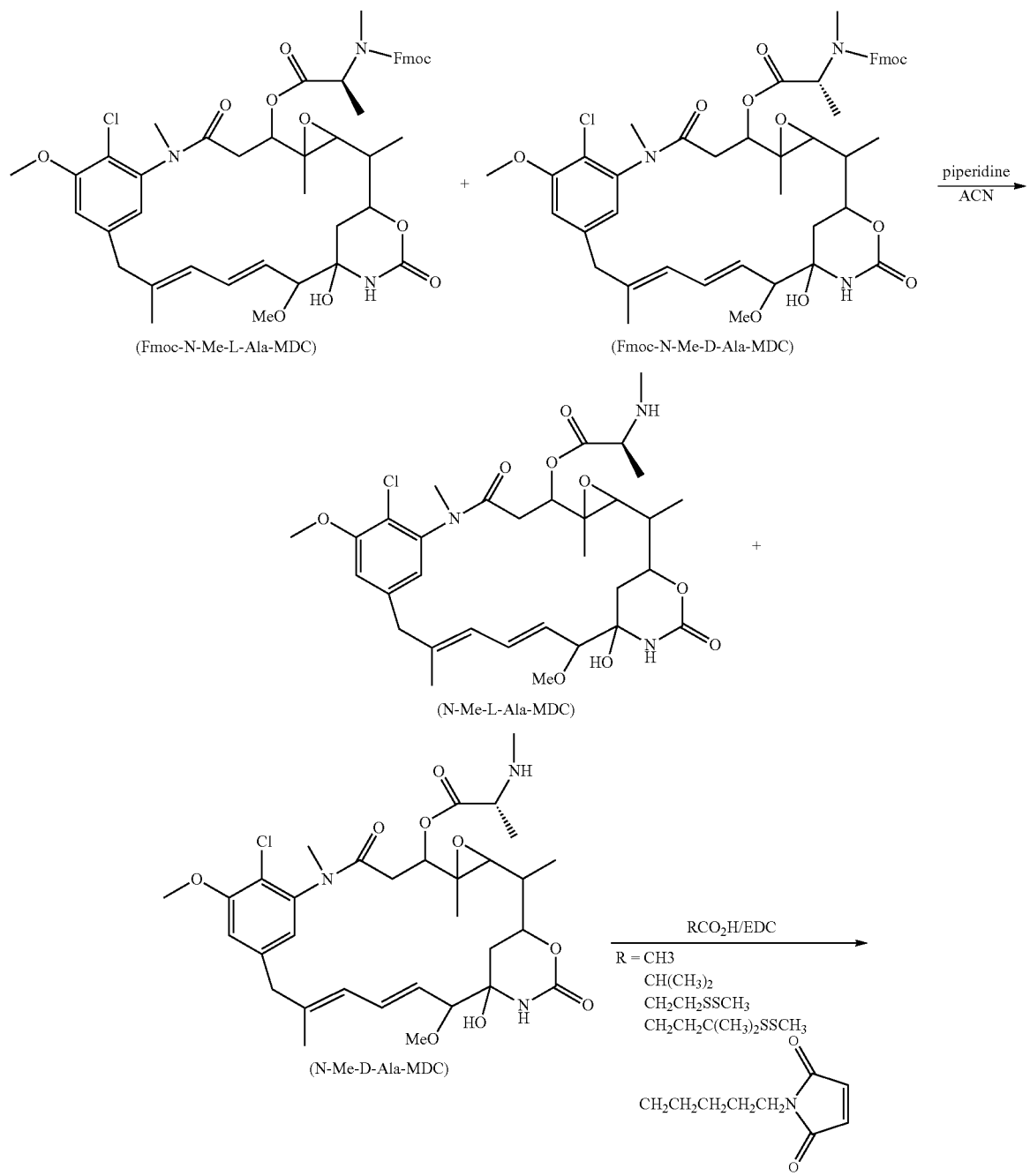

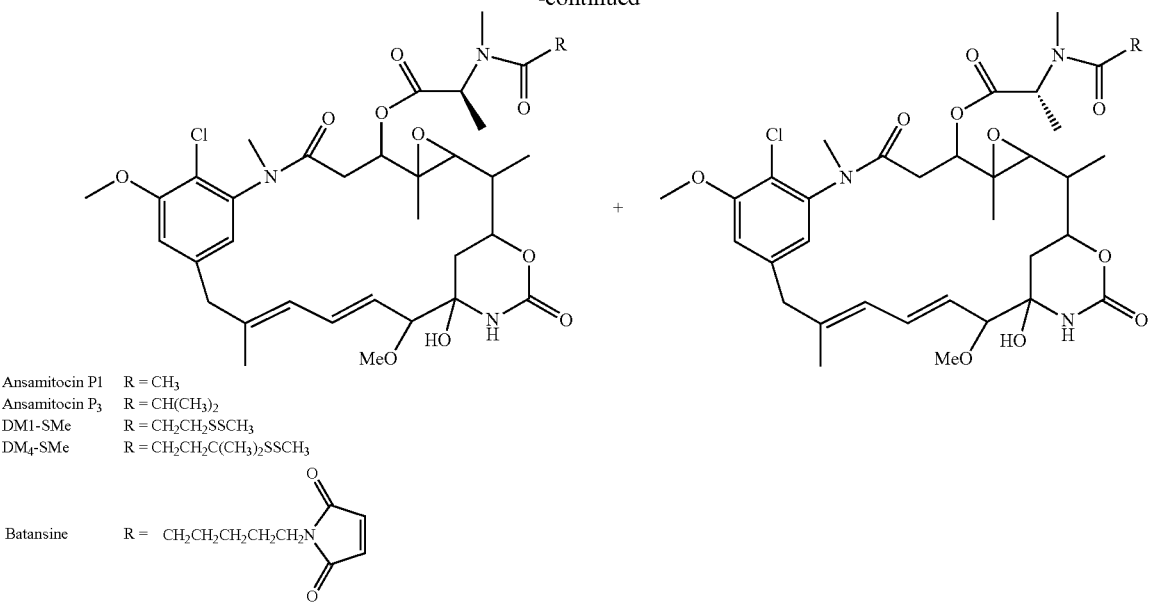

Ansamitocin P1   R = CH₃
Ansamitocin P3   R = CH(CH₃)₂
DM1-SMe          R = CH₂CH₂SSCH₃
DM4-SMe          R = CH₂CH₂C(CH₃)₂SSCH₃

Batansine        R = CH₂CH₂CH₂CH₂CH₂N(maleimide)

In some embodiments, reaction of N-Me-D/L-Ala-MDC with 3-methyldithiopropanoic acid or 3-methyldithiopropanoic 1-hydroxysuccinimide ester gives a mixture of diastereomers of DM1-SMe. These diastereomers can be separated by preparative normal phase cyano-bonded HPLC to give both isomers in good yields.

In some embodiments, reaction of N-Me-D/L-Ala-MDC with 6-maleimidocaproic acid or 6-maleimidocaproic acid 1-hydroxysuccinimide ester gives a mixture of diastereomers of 3AA-MDC. These diastereomers can be separated by chromatography or preparative HPLC to give both isomers in good yields.

In some embodiments, reaction of diastereo pure N-Me-L-Ala-MDC with 3-methyldithiopropanoic acid or 3-methyldithiopropanoic 1-hydroxysuccinimide ester provides a single isomer of desired L-DM1-SMe. This method can also be applied to the preparation of, including but not limited to, L-DM4-SMe by coupling with 4-methyl-4-methyldithiopentanoic acid.

In some embodiments, reaction of diastereo pure N-Me-L-Ala-MDC with 6-maleimidocaproic acid or 6-maleimidocaproic acid 1-hydroxysuccinimide ester provides a single isomer of desired L-3AA-MDC.

General Synthetic Methods

It will be appreciated that where typical or preferred process conditions (i.e., reaction temperatures, times, mole ratios of reactants, solvents, pressures, etc) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley and Sons, 1991), Rodd's *Chemistry of Carbon Compounds*, Volumes 1-5 and Supplementals (Elsevier Science Publishers, 1989), *Organic Reactions*, Volumes 1-40 (John Wiley and Sons, 1991), March's *Advanced Organic Chemistry*, (John Wiley and Sons, 4$^{th}$ Edition), and Larock's *Comprehensive Organic Transformations* (VCH Publishers Inc., 1989).

The various starting materials, intermediates, and compounds described herein, including stereoisomers, may be isolated and purified where appropriate using conventional techniques such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

EXAMPLES

The invention will now be illustrated by reference to non-limiting examples. Unless otherwise stated, all percents, ratios, parts, etc. are by weight.

In the following examples, NMR specetra were recorded on a Bruker AM 400 (400 MHz) spectrometer. Chemical shifts in CDCl₃ are reported in ppm relative to residual CHCl₃ as an internal standard. UV spectra were recorded on a Beckman DU-640 spectrophotometer. Mass spectra were acquired on a ThermoFinnigan LCQ DECA XP+ instrument using electrospray ionization. HPLC was performed using an Agilent HPLC 1100 system equipped with a diode array detector and a Kromasil reverse phase C-18 5 μm, 250×4.6 mm column, eluting with a gradient of acetonitrile:water (50-95%

CH₃CN 0-10 min, 95% CH₃CN 10-15 min, flow rate=1.0 mL/min. Silica gel for flash column chromatography was from Branch of Qiangdao Haiyang Chemical Co., Ltd. Maytansinol was prepared from ansamitocin P-3 (which in turn was obtained from the fermentation of the microorganism *Actinosynnema pretiosum*) as previously described (Widdison, et al. (2006) J. Med. Chem. 49: 4392-4408). Dichloromethane was dried by distillation over calcium hydride. Dimethylformamide was dried by distillation over calcium hydride under reduced pressure. All other solvents used are reagent grade or HPLC grade.

The examples below as well as throughout the application, the following abbreviations have the following meanings. If not defined, the terms have their generally accepted meanings.

ACN=acetonitrile
Ala=alanine
aq.=aqueous
brs=broad singlet
calc.=calculated
d=doublet
DCM=dichloromethane
dd=double doublet
DMAP=dimethylaminopyridine
DMF=dimethylformamide
DMSO=dimethylsulfoxide
Et=ethanol
EtOAc=ethyl acetate
g=gram
h=hour
HCl=hydrochloric acid
HPLC=high-pressure liquid chromatography
Hz=hertz
J=coupling constant
LC-MS=liquid chromatography mass spectroscopy
m=multiplet
MDC=maytansinol
Me=methyl
MeOH=methanol
MHz=megahertz
min=minute
mL=milliliter
mm=millimeter
m.p.=melting point
OTf=triflate (trifluoromethanesulfonate)
N=normal
r.t.=room temperature
Rt=retention time
s=singlet
t=triplet
TLC=thin layer chromatography
μm=micrometer Example 1

Esterification of Maytansinol with Acetic Acid (Ansamitocin P1)

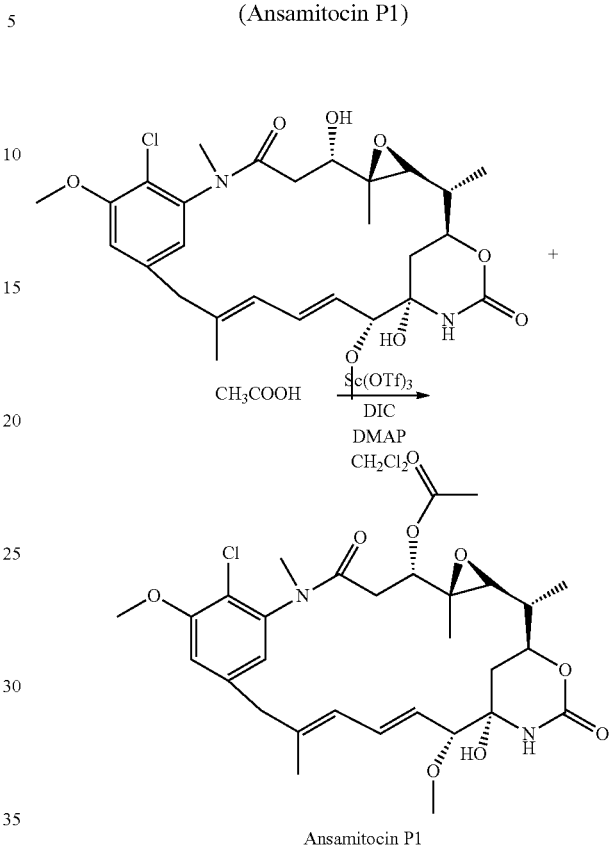

Ansamitocin P1

A mixture of maytansinol (6.00 mg, 0.01062 mmol), acetic acid (12.75 mg, 0.2124 mmol), Sc(OTf)₃ (3.14 mg, 0.00637 mmol) and DMAP (3.89 mg, 0.03186 mmol) in CH₂Cl₂ (1 mL) was stirred for 0.5 h at −8° C. DIC (29.49 mg, 0.2337 mmol) was added dropwise. The mixture was stirred till completion, quenched with diluted HCl, extracted with CH₂Cl₂. The organic layer was washed with aq. NaHCO₃, brine, and dried over anhydrous Na₂SO₄. The solvent was removed under reduced pressure. Chromatography (silica gel, CH₂Cl₂/MeOH 30:1) gave the desired product ansamitocin P1. LC-MS (M+Na⁺) calc.: 629.2. found: 629.3.

Example 2

Esterification of Maytansinol with Isobutyric Acid (Ansamitocin P3)

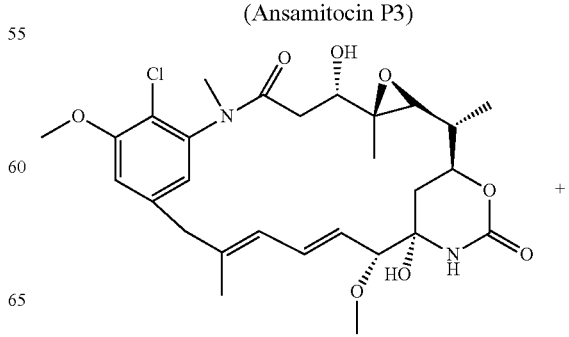

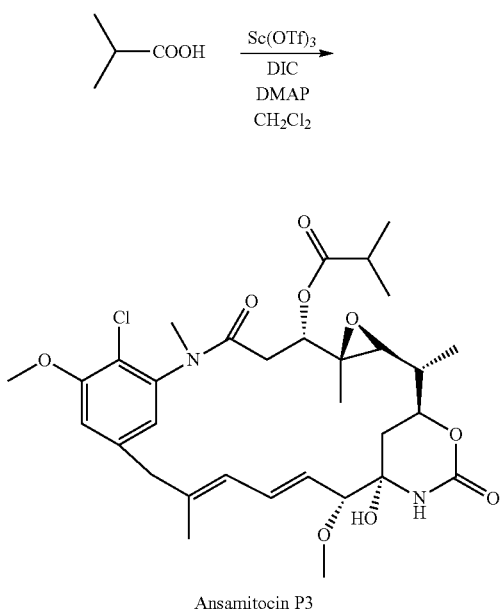

Ansamitocin P3

A mixture of maytansinol (6.00 mg, 0.01062 mmol), isobutyric acid (23.60 mg, 0.2124 mmol), Sc(OTf)$_3$ (3.14 mg, 0.00637 mmol) and DMAP (3.89 mg, 0.03186 mmol) in CH$_2$Cl$_2$ (1 mL) was stirred for 0.5 h at −8° C. DIC (29.49 mg, 0.2337 mmol) was added dropwise. The mixture was stirred till completion, quenched with diluted HCl, and extracted with CH$_2$Cl$_2$. The organic layer was washed with aq. NaHCO$_3$, brine, and dried over anhydrous Na$_2$SO$_4$. The solvent was removed under reduced pressure. Chromatography (silica gel, CH$_2$Cl$_2$/MeOH 30:1) gave the desired product ansamitocin P3. LC-MS (M+Na$^+$) calc.: 657.3. found: 657.4.

Example 3

Esterification of Maytansinol with 6-Oxo-6-(2-trimethylsilyl)ethoxy)hexanoic Acid

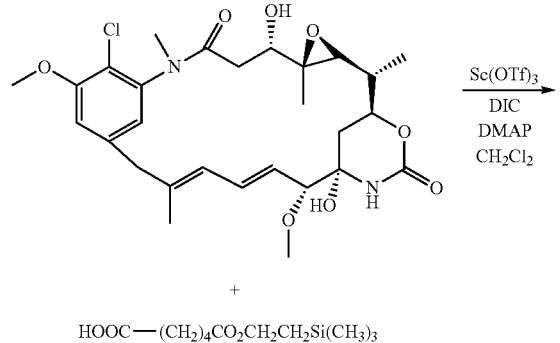

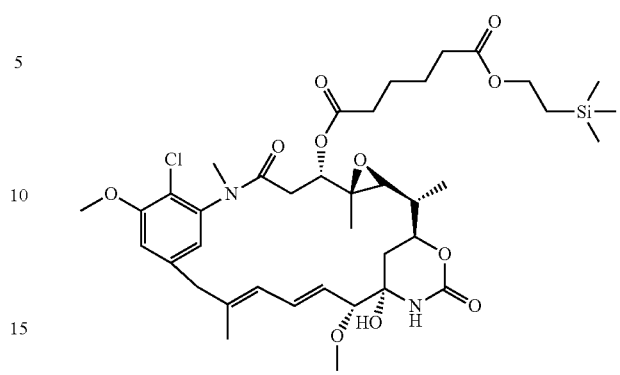

A mixture of maytansinol (6.00 mg, 0.01062 mmol), 6-oxo-6-(2-trimethylsilyl)ethoxy)hexanoic acid (52.27 mg, 0.2124 mmol), Sc(OTf)$_3$ (3.14 mg, 0.00637 mmol) and DMAP (3.89 mg, 0.03186 mmol) in CH$_2$Cl$_2$ (1 mL) was stirred for 0.5 h at −8° C. DIC (29.49 mg, 0.2337 mmol) was added dropwise. The mixture was stirred till completion, quenched with diluted HCl, and extracted with CH$_2$Cl$_2$. The organic layer was washed with aq. NaHCO$_3$, brine, and dried over anhydrous Na$_2$SO$_4$. The solvent was removed under reduced pressure. Chromatography (silica gel, CH$_2$Cl$_2$/MeOH 30:1) gave the desired product. LC-MS (M+Na$^+$) calc.: 815.3. found: 815.4.

Example 4

Esterification of Maytansinol with N-acetyl-N-methyl-L-alanine (Maytansine)

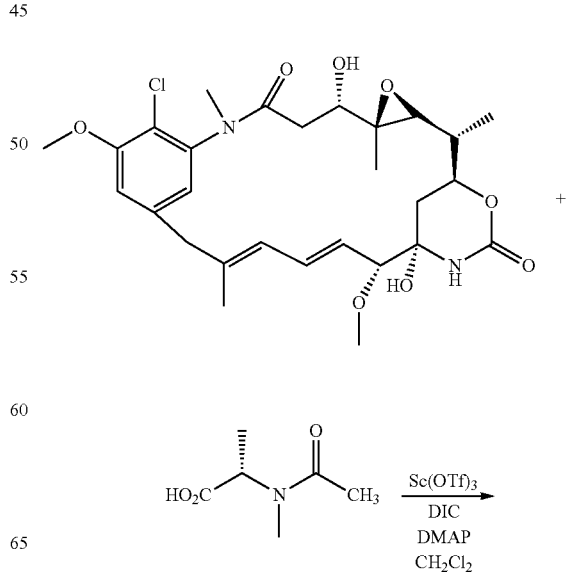

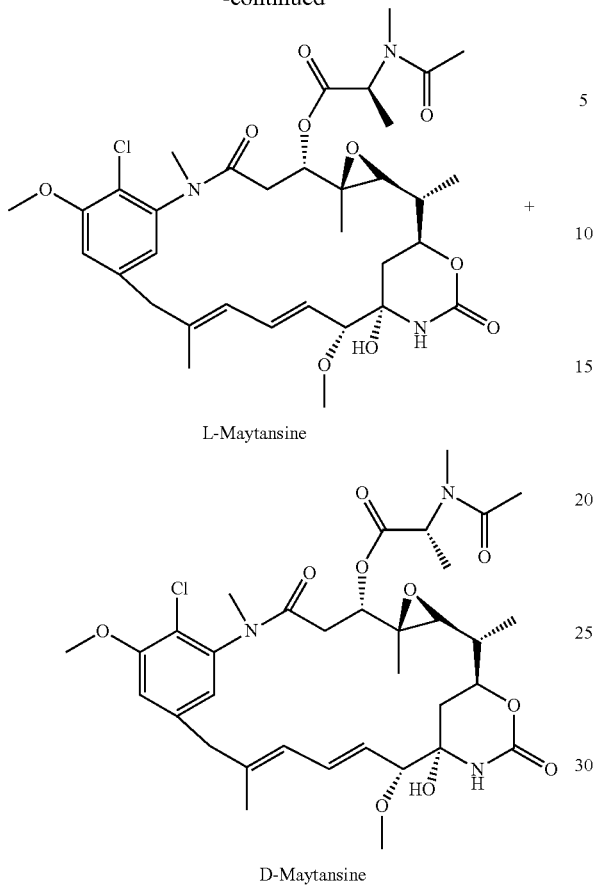

L-Maytansine

D-Maytansine

A mixture of maytansinol (6.00 mg, 0.01062 mmol), N-acetyl-N-methyl-L-alanine (30.84 mg, 0.2124 mmol), Sc(OTf)$_3$ (3.14 mg, 0.00637 mmol) and DMAP (3.89 mg, 0.03186 mmol) in CH$_2$Cl$_2$ (1 mL) was stirred for 0.5 h at −8° C. DIC (29.49 mg, 0.2337 mmol) was added dropwise. The mixture was stirred till completion, quenched with diluted HCl, and extracted with CH$_2$Cl$_2$. The organic layer was washed with aq. NaHCO$_3$, brine, and dried over anhydrous Na$_2$SO$_4$. The solvent was removed under reduced pressure. Chromatography (silica gel, CH$_2$Cl$_2$/MeOH 30:1) gave the desired product. LC-MS (M+Na$^+$) calc.: 714.3. found: 714.4.

Example 5

Esterification of Maytansinol with N-methyl-N-[(3-methyldithio)-1-oxopropyl]-L-alanine (DM1-SMe)

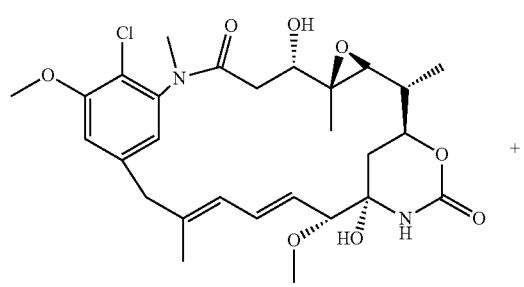

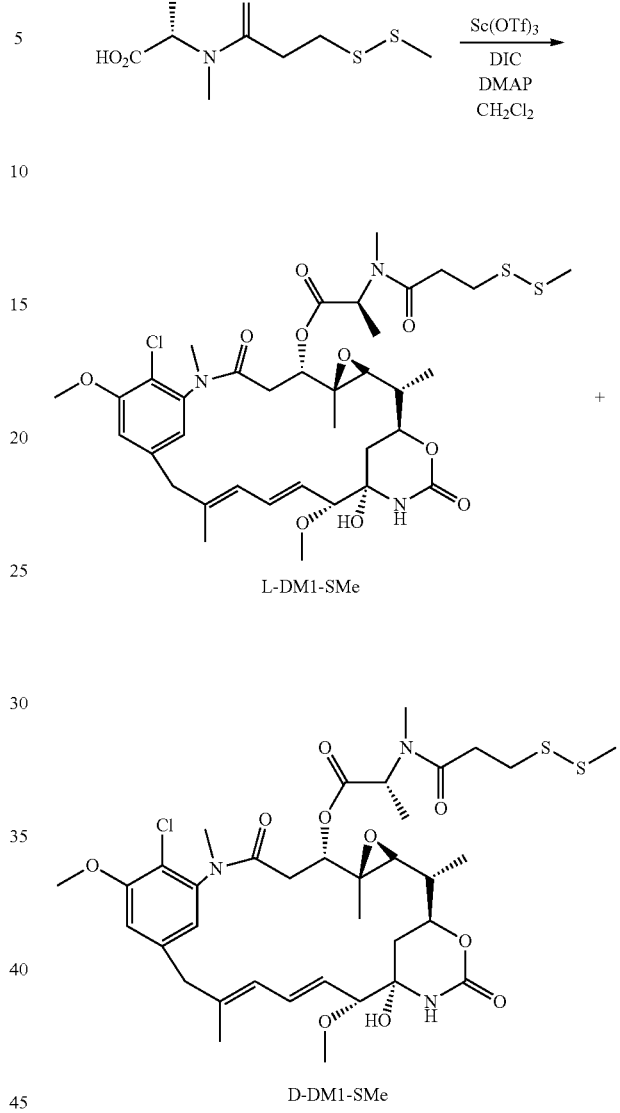

L-DM1-SMe

D-DM1-SMe

A mixture of maytansinol (0.685 g, 1.212 mmol), N-methyl-N-[(3-methyldithio)-1-oxopropyl]-L-alanine (5.750 g, 24.24 mmol), Sc(OTf)$_3$ (0.358 g, 0.727 mmol) and DMAP (0.444 g, 3.637 mmol) in CH$_2$Cl$_2$ (100 mL) was stirred for 0.5 h at −8° C. DIC (3.365 g, 26.66 mmol) was added dropwised. The mixture was stirred till completion, filtered to recover the Sc(OTf)$_3$, quenched with diluted HCl, and extracted with CH$_2$Cl$_2$. The organic layer was washed with aq. NaHCO$_3$ and brine, dried over anhydrous Na$_2$SO$_4$. The solvent was removed under reduced pressure. Chromatography (silica gel: CH$_2$Cl$_2$/MeOH 30:1) gave the crude product. Further purification by preparative HPLC on a YMC C-18 column (250×20 mm, S 10 μm) gave white solid as desired product. LC-MS (M+Na$^+$) calc.: 806.3. found: 806.3.

Example 6

Esterification of Maytansinol with N-methyl-N-[4-methyl-(4-methyldithio)-1-oxopentyl]-L-alanine (DM4-SMe)

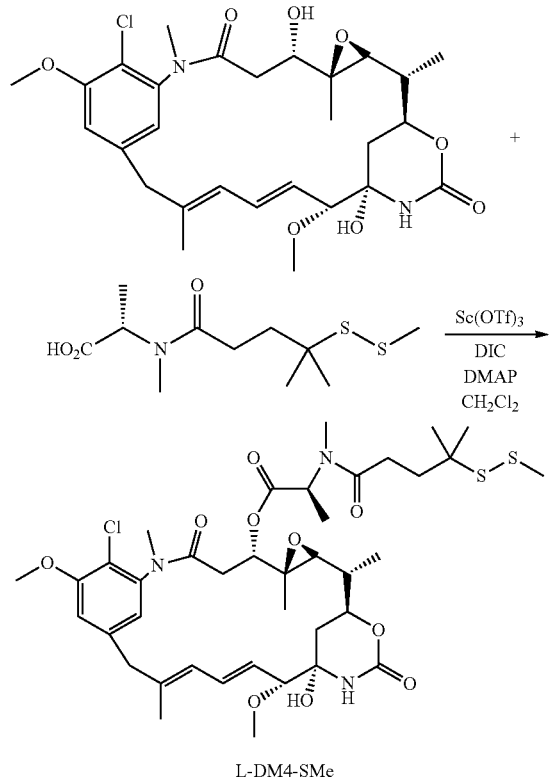

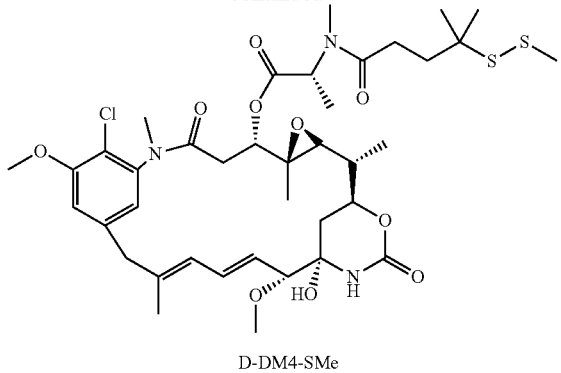

A mixture of maytansinol (0.114 g, 0.202 mmol), N-methyl-N-[4-methyl-(4-methyldithio)-1-oxopropyl]-L-alanine (1.129 g, 4.040 mmol), Sc(OTf)$_3$ (0.0597 g, 0.121 mmol) and DMAP (0.074 g, 0.606 mmol) in CH$_2$Cl$_2$ (15 mL) was stirred for 0.5 h at −8° C. DIC (0.561 g, 4.443 mmol) was added dropwised. The mixture was stirred till completion, filtered to recover the Sc(OTf)$_3$, quenched with diluted HCl, and extracted with CH$_2$Cl$_2$. The organic layer was washed with aq. NaHCO$_3$ and brine, and dried over anhydrous Na$_2$SO$_4$. The solvent was removed under reduced pressure. Chromatography (silica gel: CH$_2$Cl$_2$/MeOH 30:1) gave the crude product. Further purification by preparative HPLC on a YMC C-18 column (250×20 mm, S 10 μm) gave white solid as the desired product. LC-MS (M+Na$^+$) calc.: 848.3. found: 848.4.

Example 7

Esterification of Maytansinol with N-methyl-N-[1,6-di-oxo-6-(2-trimethylsilyl)ethoxy)hexyl]-L-alanine

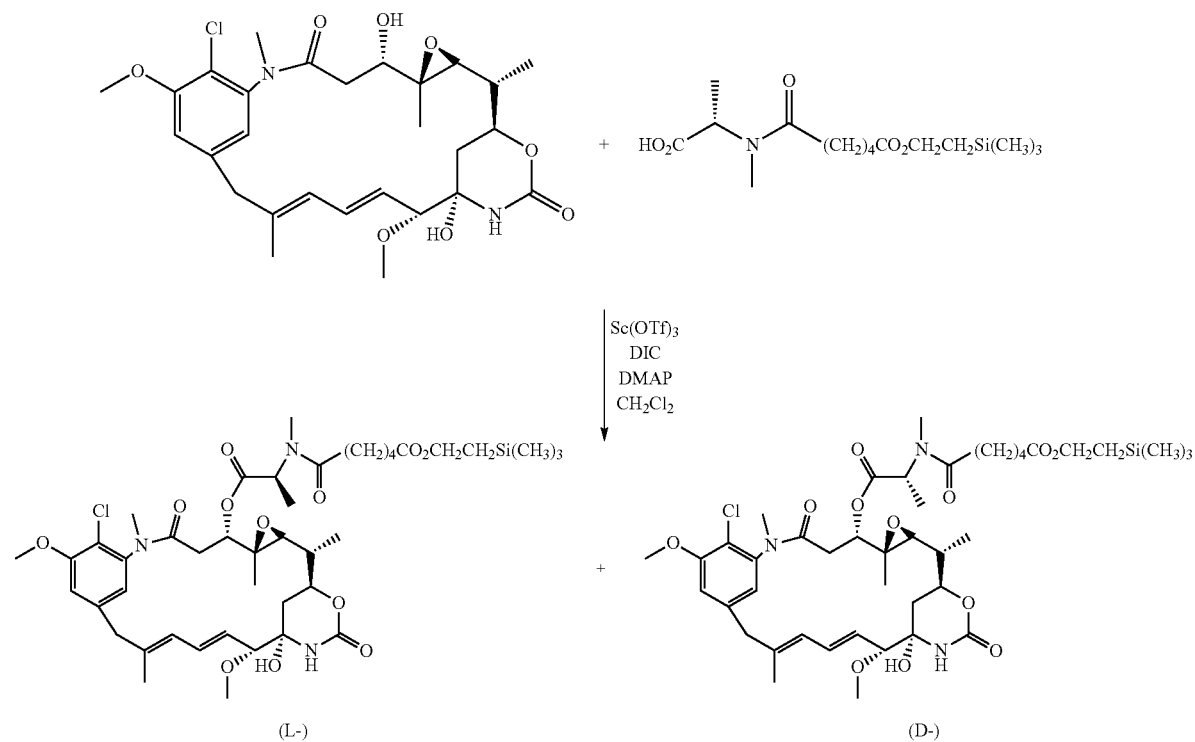

A mixture of maytansinol (0.114 g, 0.202 mmol), N-methyl-N-[1,6-di-oxo-6-(2-trimethylsilyl)ethoxy)hexyl]-L-alanine (1.339 g, 4.040 mmol), Sc(OTf)$_3$ (0.0597 g, 0.121 mmol) and DMAP (0.074 g, 0.606 mmol) in CH$_2$Cl$_2$ (15 mL) was stirred for 0.5 h at −8° C. DIC (0.561 g, 4.443 mmol) was added dropwised. The mixture was stirred till completion, filtered to recover the Sc(OTf)$_3$, quenched with diluted HCl, and extracted with CH$_2$Cl$_2$. The organic layer was washed with aq. NaHCO$_3$ and brine, and dried over anhydrous Na$_2$SO$_4$. The solvent was removed under reduced pressure. Chromatography (silica gel: CH$_2$Cl$_2$/MeOH 50:1) gave the crude product. Further purification by preparative HPLC on a YMC C-18 column (250×20 mm, S 10 μm) gave white solid as desired product. LC-MS (M+Na$^+$) calc.: 900.4. found: 900.5.

Example 8

Esterification of Maytansinol with N-acetyl-5-thiomethyl-cysteine

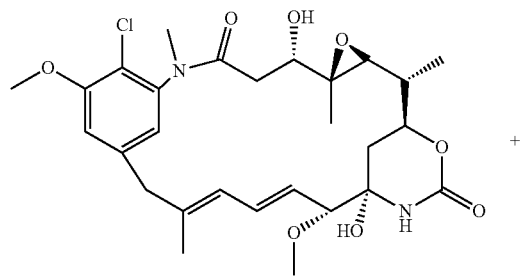

+

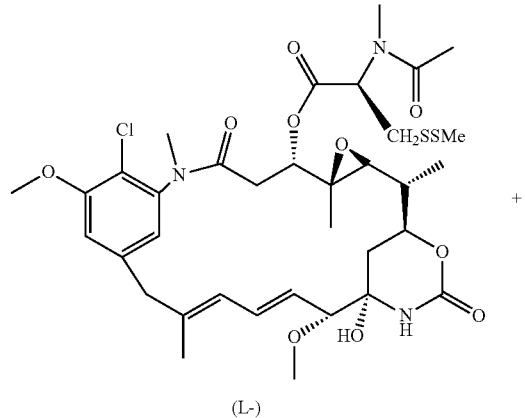

(L-)

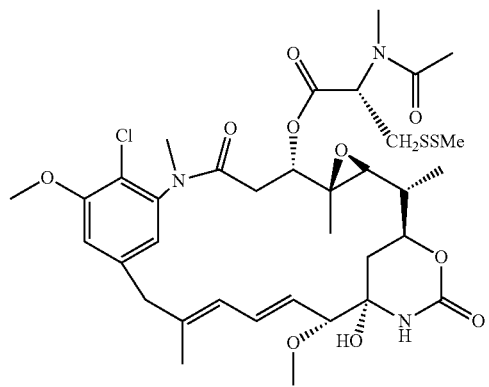

(D-)

A mixture of maytansinol (6.00 mg, 0.01062 mmol), N-acetyl-5-thiomethyl-cysteine (47.43 mg, 0.2124 mmol), Sc(OTf)$_3$ (3.14 mg, 0.00637 mmol) and DMAP (3.89 mg, 0.03186 mmol) in CH$_2$Cl$_2$ (1 mL) was stirred for 0.5 h at −8° C. DIC (29.49 mg, 0.2337 mmol) was added dropwise. The mixture was stirred till completion, quenched with diluted HCl, and extracted with CH$_2$Cl$_2$. The organic layer was washed with aq. NaHCO$_3$, brine, and dried over anhydrous Na$_2$SO$_4$. The solvent was removed under reduced pressure. Chromatography (silica gel, CH$_2$Cl$_2$/MeOH 30:1) gave the desired product. LC-MS (M+Na$^+$) calc.: 792.2. found: 792.3.

Example 9

Esterification of Maytansinol with N-acetyl-5-thiomethyl-methionine

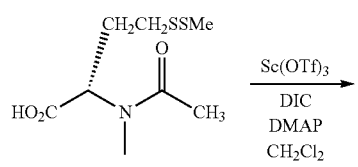

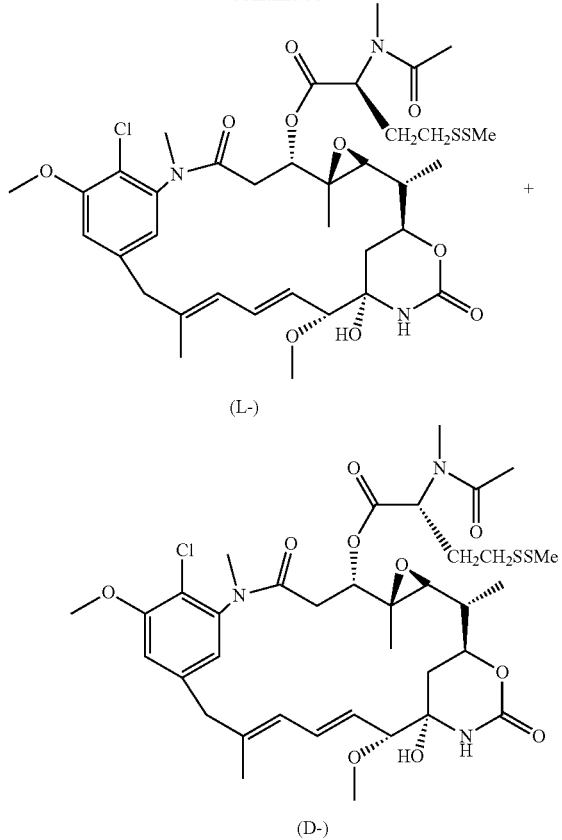

(L-)

(D-)

A mixture of maytansinol (6.00 mg, 0.01062 mmol), N-acetyl-5-thiomethyl-methionine (50.40 mg, 0.2124 mmol), Sc(OTf)$_3$ (3.14 mg, 0.00637 mmol) and DMAP (3.89 mg, 0.03186 mmol) in CH$_2$Cl$_2$ (1 mL) was stirred for 0.5 h at −8° C. DIC (29.49 mg, 0.2337 mmol) was added dropwise. The mixture was stirred till completion, quenched with diluted HCl, and extracted with CH$_2$Cl$_2$. The organic layer was washed with aq. NaHCO$_3$, brine, and dried over anhydrous Na$_2$SO$_4$. The solvent was removed under reduced pressure. Chromatography (silica gel, CH$_2$Cl$_2$/MeOH 30:1) gave the desired product. LC-MS (M+Na$^+$) calc.: 806.3. found: 806.4.

Example 10

Esterification of Maytansinol with Fmoc-N-methyl-L-alanine (Fmoc-N-Me-D/L-Ala-MDC)

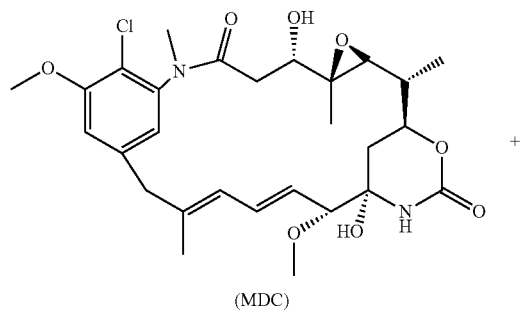

(MDC)

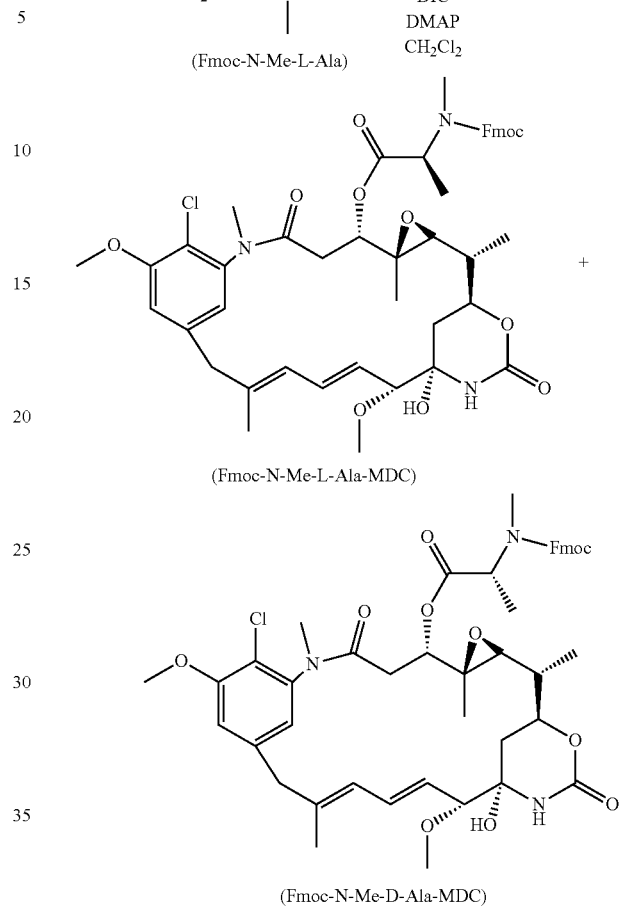

(Fmoc-N-Me-L-Ala)

(Fmoc-N-Me-L-Ala-MDC)

(Fmoc-N-Me-D-Ala-MDC)

A mixture of maytansinol (0.600 g, 1.062 mmol), Fmoc-N-Me-L-Ala (6.911 g, 21.24 mmol), Sc(OTf)$_3$ (0.314 g, 0.637 mmol) and DMAP (0.389 g, 3.186 mmol) in CH$_2$Cl$_2$ (100 mL) was stirred for 0.5 h at −8° C. DIC (2.949 g, 23.37 mmol) was added dropwise, stirred for 0.5 h, warmed to r.t. slowly, filtered to recover the Lewis acid catalyst, the filtrate was quenched with diluted HCl and extracted with CH$_2$Cl$_2$. The combined organic phase was washed with NaHCO$_3$ aq, brine, dried over anhydrous Na$_2$SO$_4$. The solvent was removed under reduced pressure. Chromatography (silica gel, CH$_2$Cl$_2$/MeOH 30:1) gave the desired product as a mixture of diastereomer Fmoc-N-Me-D/L-Ala-MDC: white solid (0.8385 g, 90.5%). Further column chromatography (silica gel, CH$_2$Cl$_2$/MeOH 100:1 to 20:1) gave two fractions as pure diastereomer. The higher Rf fraction was determined to be the D-aminoacyl ester diastereomer (Fmoc-N-Me-D-Ala-MDC), while the lower Rf fraction was the desired L-aminoacyl ester (Fmoc-N-Me-L-Ala-MDC). Fmoc-N-Me-L-Ala-MDC: white solid (0.4262 g, 46.0% yield), $^1$H NMR (400 MHz, CDCl$_3$): δ0.77 (3H, s), 1.22-1.32 (6H, m), 1.40-1.48 (1H, m), 1.63 (3H, s), 2.13 (1H, dd, J=14.4, 2.8 Hz), 2.53 (1H, dd, J=14.4, 10.8 Hz), 2.64 (3H, s), 2.88 (3H, s), 3.00 (1H, d, J=9.6 Hz), 3.07 (1H, d, J=12.4 Hz), 3.35 (3H, s), 3.48 (1H, d, J=8.8 Hz), 3.59 (1H, d, J=11.2 Hz), 3.97 (3H, s), 4.13-4.19 (1H, m), 4.15 (1H, s), 4.24 (1H, t, J=10.8 Hz), 4.72-4.77 (2H, m), 5.03 (1H, q, J=6.8 Hz), 5.65 (1H, dd, J=15.2, 9.2 Hz), 6.29 (1H, br), 6.41 (1H, dd, J=15.2, 11.2 Hz), 6.52 (1H, d, J=1.2 Hz), 6.70 (1H, d, J=10.8 Hz), 6.79 (1H, d, J=1.2 Hz), 7.33 (1H, t, J=7.6 Hz), 7.36 (1H, t, J=7.6 Hz), 7.39 (1H, d, J=7.6 Hz), 7.49 (1H, d, J=7.6 Hz), 7.70 (1H, d, J=7.6 Hz), 7.72 (1H, d, J=7.6 Hz). LC-MS (M+Na⁺) calc.: 894.3. found: 894.3. Fmoc-N-Me-D-Ala-MDC: white solid (0.3993 g, 43.1% yield), ¹H NMR (400 MHz, CDCl₃): δ0.84 (3H, s), 1.22-1.27 (3H, m), 1.40-1.48 (1H, m), 1.51 (3H, d, J=7.6 Hz), 1.67 (3H, s), 2.20 (1H, dd, J=14.4, 2.8 Hz), 2.63 (1H, dd, J=14.4, 12.4 Hz), 2.85 (1H, d, J=9.6 Hz), 2.96 (3H, s), 3.17 (3H, s), 3.20 (1H, s), 3.24 (3H, s), 3.40 (1H, d, J=9.2 Hz), 3.51 (1H, d, J=12.8 Hz), 3.99 (3H, s), 4.20-4.28 (2H, m), 4.38-4.43 (2H, m), 4.80-4.98 (2H, m), 5.80 (1H, dd, J=15.2, 11.2 Hz), 6.18 (1H, s), 6.25 (1H, d, J=10.8 Hz), 6.40 (1H, dd, J=15.2, 11.2 Hz), 6.79 (1H, d, J=1.6 Hz), 6.84 (1H, d, J=1.6 Hz), 7.32 (2H, t, J=7.6 Hz), 7.41 (2H, t, J=7.6 Hz), 7.61 (2H, d, J=7.6 Hz), 7.77 (2H, d, J=7.6 Hz). LC-MS (M+Na⁺) calc.: 894.3. found: 894.3.

Example 11

Deprotection of Fmoc-N-Me-D/L-Ala-MDC(N-Me-D/L-Ala-MDC)

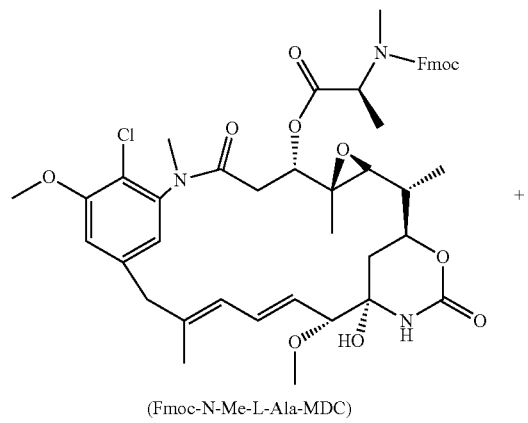

(Fmoc-N-Me-L-Ala-MDC)

+

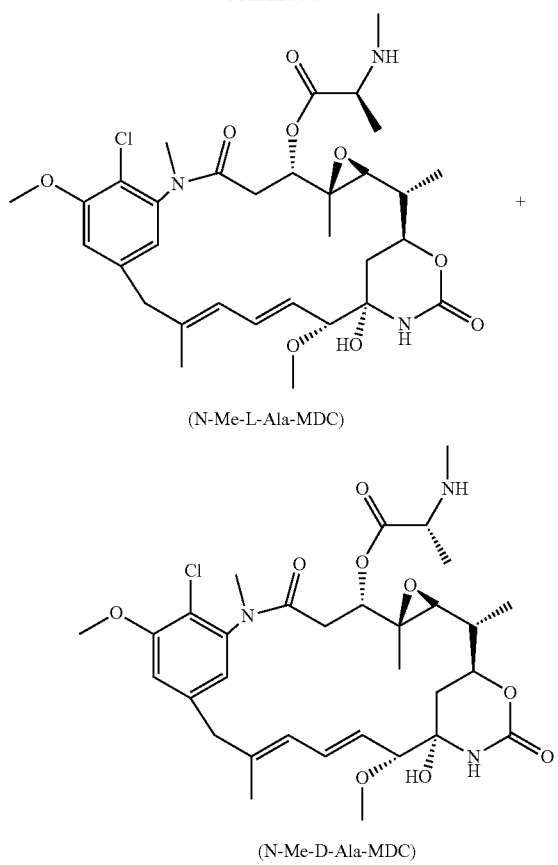

(N-Me-L-Ala-MDC)

(N-Me-D-Ala-MDC)

Into Fmoc-N-Me-D/L-Ala-MDC (0.463 g, 0.5307 mmol) in ACN (200 mL) was added piperidine (0.865 g, 10.15 mmol). The mixture was stirred at r.t. for 4 h, quenched with water and extracted with CH₂Cl₂. The combined organic phase was washed with brine and dried over Na₂SO₄. The solvent was removed under reduced pressure to give the crude product, which was used in the next step without further purification. LC-MS (M+H⁺) calc.: 650.3. found: 650.3. Rt: 3.96 min.

Deprotection of Fmoc-N-Me-L-Ala-MDC(N-Me-L-Ala-MDC)

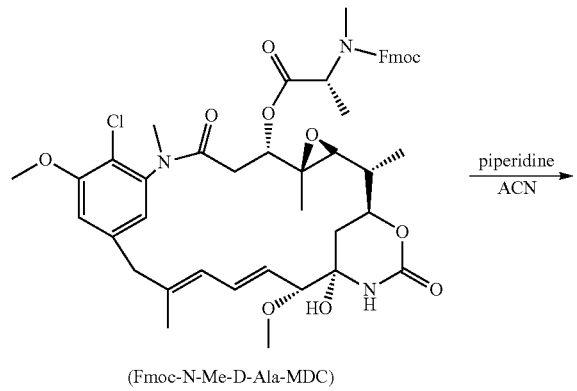

(Fmoc-N-Me-D-Ala-MDC)

piperidine / ACN →

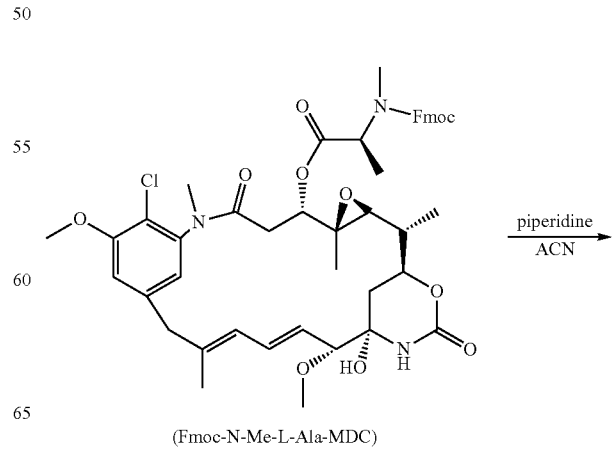

(Fmoc-N-Me-L-Ala-MDC)

piperidine / ACN →

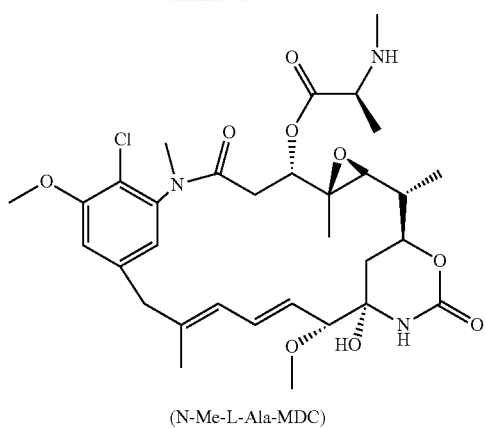

(N-Me-L-Ala-MDC)

Into Fmoc-N-Me-L-Ala-MDC (0.463 g, 0.5307 mmol) in ACN (200 mL) was added piperidine (0.865 g, 10.15 mmol). The mixture was stirred at r.t. for 4 h, quenched with water and extracted with $CH_2Cl_2$. The combined organic phase was washed with brine and dried over $Na_2SO_4$. The solvent was removed under reduced pressure to give the crude product, which was used in the next step without further purification. LC-MS (M+H$^+$) calc.: 650.3. found: 650.3. Rt: 3.96 min.

Example 12

Condensation of N-Me-D/L-Ala-MDC with 3-methyldithiopropanoic acid (L-DM1-SMe and D-DM1-SMe)

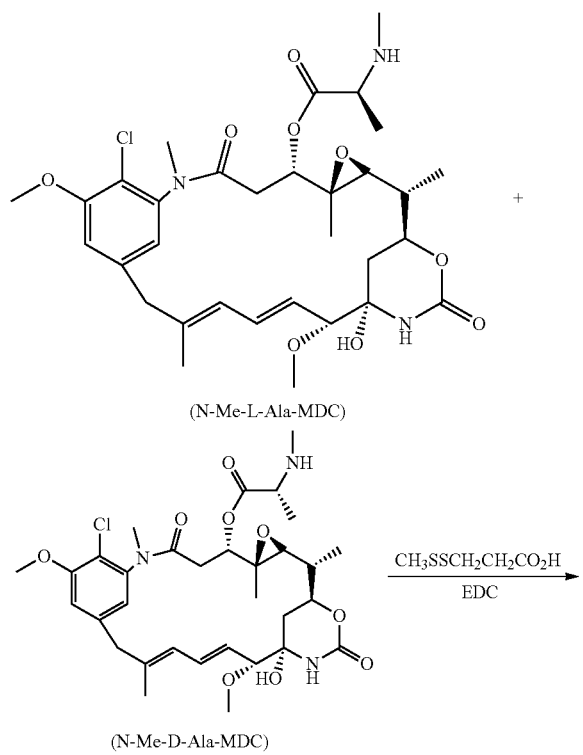

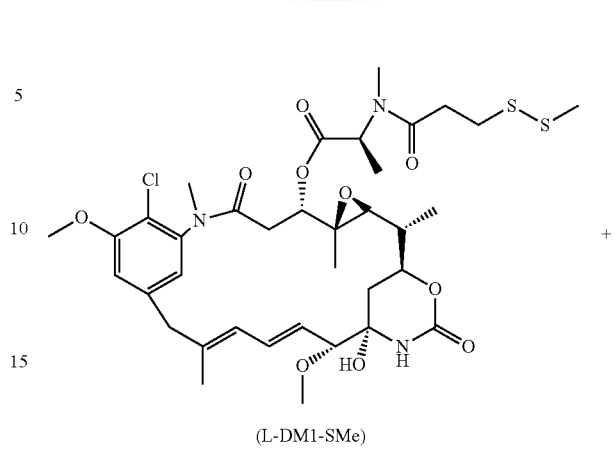

(L-DM1-SMe)

(D-DM1-SMe)

Into the above prepared N-Me-D/L-Ala-MDC (0.02293 mmol) and 3-methyldithiopropanoic acid (0.0140 g, 0.09172 mmol) in DMF (2 mL) at 0° C. was added EDC (0.0176 g, 0.09172 mmol). The mixture was stirred at r.t. overnight, quenched with water, extracted with EtOAc, washed with brine, and dried over $Na_2SO_4$. The solvent was removed under reduced pressure. Column chromatography (silica gel, $CH_2Cl_2$/MeOH 30:1) gave the crude product. Further purification by preparative HPLC on a YMC C-18 column (250×20 mm, S 10 μm) gave the product in a white solid as inseparable diastereomers (0.0172 mg, 74.8%). The higher Rt fraction was determined to be the D-aminoacyl ester diastereomer (D-DM1-SMe, 41.4%), while the lower Rt fraction was the desired L-aminoacyl ester (L-DM1-SMe, 58.6%). L-DM1-SMe: white solid (10.1 mg, 43.8% yield), $^1$H NMR (400 MHz, CDCl$_3$): δ 0.84 (3H, s), 1.11-1.23 (1H, m), 1.31 (3H, d, J=6.1 Hz), 1.35 (3H, d, J=7.2 Hz), 1.40-1.52 (1H, m), 1.68 (3H, s), 1.97 (1H, d, J=9.0 Hz), 2.23 (1H, dd, J=12.8, 15.4 Hz), 2.31 (3H, s), 2.65 (1H, dd, J=12.8, 15.4 Hz), 2.73-2.86 (2H, m), 2.90 (3H, s), 2.92-3.03 (2H, m), 3.10 (1H, d, J=8.8 Hz), 3.14 (1H, d, J=12.8 Hz), 3.28 (3H, s), 3.34 (3H, s), 3.54 (1H, d, J=9.4 Hz), 3.72 (1H, d, J=12.8 Hz), 4.02 (3H, s), 4.31 (1H, t, J=11.2 Hz), 4.76 (1H, dd, J=3.0, 12.8 Hz), 5.45 (1H, q, J=6.8 Hz), 5.65 (1H, dd, J=15.2, 9.2 Hz), 6.25 (1H, s), 6.47 (1H, dd, J=15.2, 11.2 Hz), 6.64 (1H, s), 6.65 (2H, s), 6.72 (1H, d, J=11.2 Hz), 6.82 (1H, s). LC-MS (M+Na⁺) calc.: 806.3. found: 806.3. Rt: 7.80 min. D-DM1-SMe: white solid (7.1 mg, 31.0% yield), ¹H NMR (400 MHz, CDCl₃): δ 0.84 (3H, s), 1.11-1.23 (1H, m), 1.22-1.29 (3H, m), 1.49 (3H, d, J=7.2 Hz), 1.68 (3H, s), 2.23 (1H, dd, J=3.0, 14.4 Hz), 2.40 (3H, s), 2.65 (1H, dd, J=12.8, 14.4 Hz), 2.79-2.84 (3H, m), 2.92-3.00 (2H, m), 3.04 (3H, s), 3.15 (3H, s), 3.33 (3H, s), 3.44 (1H, d, J=9.4 Hz), 3.50 (1H, d, J=12.8 Hz), 4.02 (3H, s), 4.31 (1H, m), 4.90 (1H, dd, J=3.0, 12.8 Hz), 5.17 (1H, q, J=6.8 Hz), 5.88 (1H, dd, J=15.2, 9.2 Hz), 6.22-6.26 (2H, m), 6.47 (1H, dd, J=15.2, 11.2 Hz), 6.78 (1H, d, J=1.6 Hz), 6.82 (1H, d, J=1.6 Hz). LC-MS (M+Na⁺) calc.: 806.3. found: 806.3. Rt: 8.01 min.

Example 13

Condensation of N-Me-L-Ala-MDC with 3-methyldithiopropanoic acid (L-DM1-SMe)

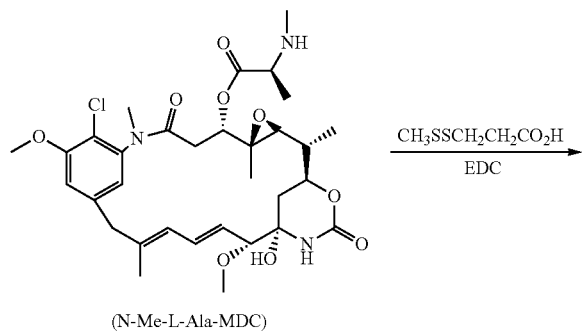

(N-Me-L-Ala-MDC)

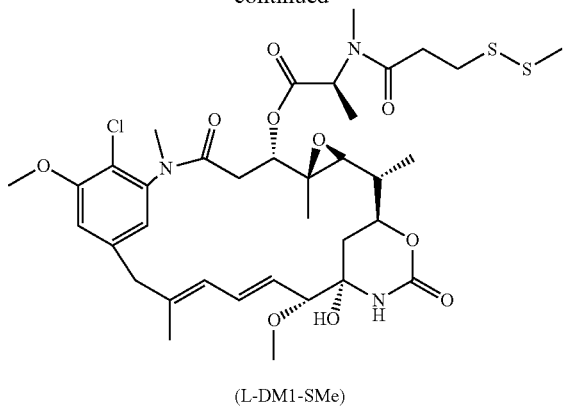

(L-DM1-SMe)

Into above prepared N-Me-L-Ala-MDC (0.5307 mmol) and 3-methyldithiopropanoic acid (0.323 g, 2.123 mmol) in DMF (25 mL) under 0° C. was added EDC (0.407 g, 2.123 mmol). The mixture was stirred at r.t. overnight, quenched with water, and extracted with EA. The organic phase was washed with brine and dried over Na₂SO₄. The solvent was removed under reduced pressure. Chromatography (silica gel: CH₂Cl₂/MeOH 30:1) gave the crude product. Further purification by preparative HPLC on a YMC C-18 column (250×20 mm, S 10 μm) gave the desired L-DM1-SMe: white solid (0.280 g, 67.3% overall yield over two steps), ¹H NMR (400 MHz, CDCl₃): δ 0.79 (3H, s), 1.19-1.23 (1H, m), 1.25 (3H, d, J=7.2 Hz), 1.30 (3H, d, J=7.2 Hz), 1.38-1.52 (1H, m), 1.55 (1H, d, J=12.8 Hz), 1.63 (3H, s), 2.16 (1H, dd, J=2.8, 14.4 Hz), 2.25 (3H, s), 2.59 (1H, dd, J=12.8, 15.4 Hz), 2.63-2.84 (2H, m), 2.85 (3H, s), 2.87-3.00 (2H, m), 3.03 (1H, d, J=8.8 Hz), 3.14 (1H, d, J=13.2 Hz), 3.22 (3H, s), 3.36 (3H, s), 3.51 (1H, d, J=7.6 Hz), 3.67 (1H, d, J=12.8 Hz), 3.97 (3H, s), 4.29 (1H, t, J=6.8 Hz), 4.76 (1H, dd, J=2.8, 12.0 Hz), 5.40 (1H, q, J=6.8 Hz), 5.65 (1H, dd, J=15.4, 9.2 Hz), 6.28 (1H, s), 6.42 (1H, dd, J=15.2, 11.2 Hz), 6.63 (1H, d, J=1.6 Hz), 6.71 (1H, d, J=11.2 Hz), 6.81 (1H, d, J=1.6 Hz). LC-MS (M+Na⁺) calc.: 806.3. found: 806.3. Rt: 7.80 min.

Example 14

Condensation of N-Me-D/L-Ala-MDC with 4-methyl-4-(methyldithio)pentanoic acid (L-DM4-SMe and D-DM4-SMe)

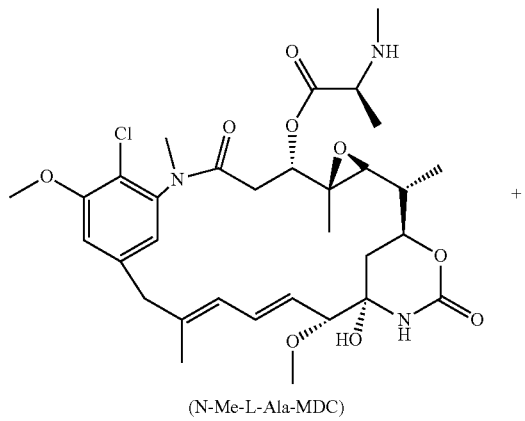

(N-Me-L-Ala-MDC)

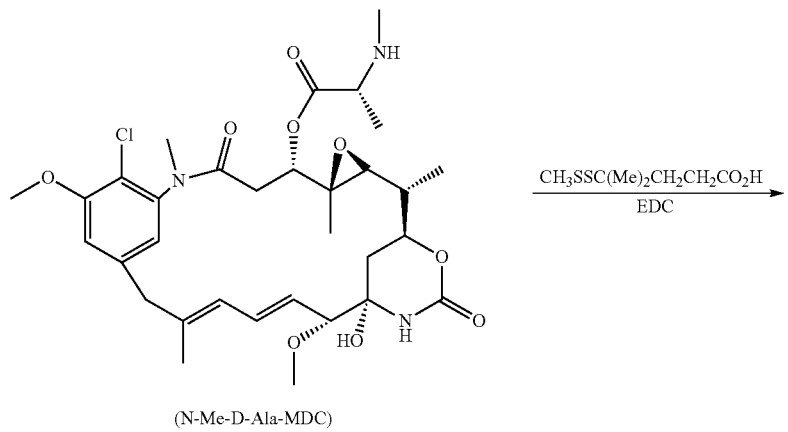

(N-Me-D-Ala-MDC)

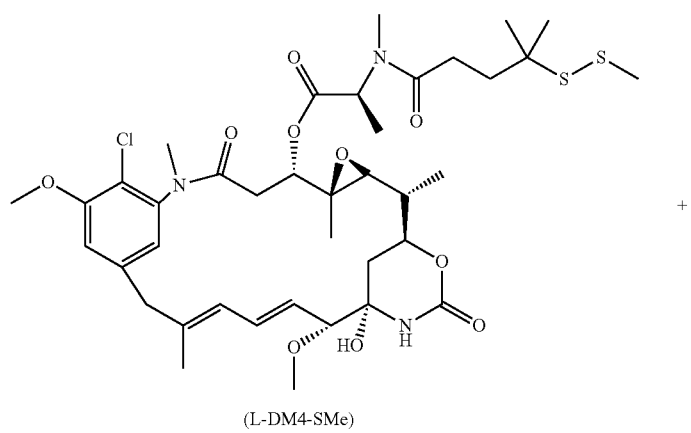

(L-DM4-SMe)

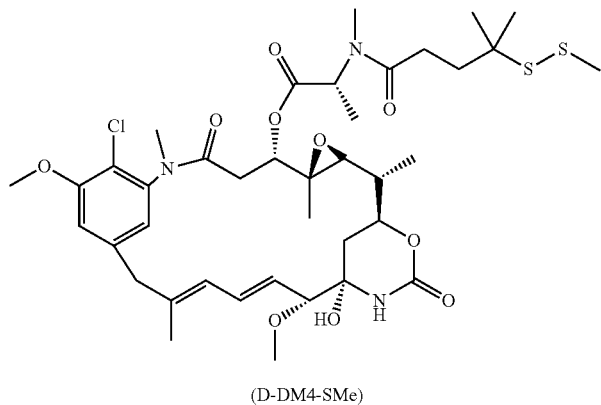

(D-DM4-SMe)

Into above prepared N-Me-D/L-Ala-MDC (0.02293 mmol) and 4-methyl-4-(methyldithio)pentanoic acid (0.0178 g, 0.09172 mmol) in DMF (2 mL) under 0° C. was added EDC (0.0176 g, 0.09172 mmol). The mixture was stirred at r.t. overnight, quenched with water, and extracted with EA. The organic phase was washed with brine, dried over $Na_2SO_4$. The solvent was removed under reduced pressure. Column chromatography (silica gel, $CH_2Cl_2$/MeOH 30:1) gave the crude product. Further purification by preparative HPLC on a YMC C-18 column (250×20 mm, S 10 μm) gave white solid as inseparable diastereomer. LC-MS (M+Na$^+$) calc.: 848.4. found: 848.4.

Example 15

Condensation of N-Me-L-Ala-MDC with 4-methyl-4-(methyldithio)pentanoic acid (L-DM4-SMe)

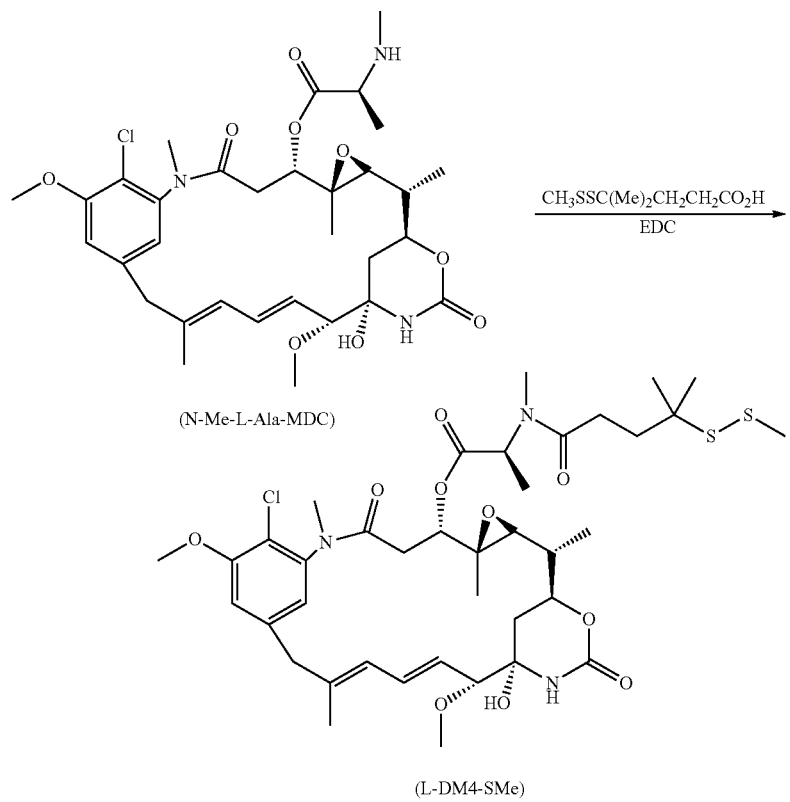

Into above prepared N-Me-L-Ala-MDC (0.5307 mmol) and 4-methyl-4-(methyldithio)pentanoic acid (0.412 g, 2.123 mmol) in DMF (25 mL) under 0° C. was added EDC (0.407 g, 2.123 mmol). The mixture was stirred at r.t. overnight, quenched with water, extracted with EtOAc, washed with brine, dried over $Na_2SO_4$. The solvent was removed under reduced pressure. Column chromatography (silica gel, $CH_2Cl_2$/MeOH 30:1) gave the crude product. Further purification by preparative HPLC on a YMC C-18 column (250×20 mm, S 10 μm) gave the desired product as white solid. LC-MS (M+Na$^+$) calc.: 848.4. found: 848.4.

Example 16

Condensation of N-Me-D/L-Ala-MDC with MA-ACP (L-3-AA-MDC and D-3AA-MDC)

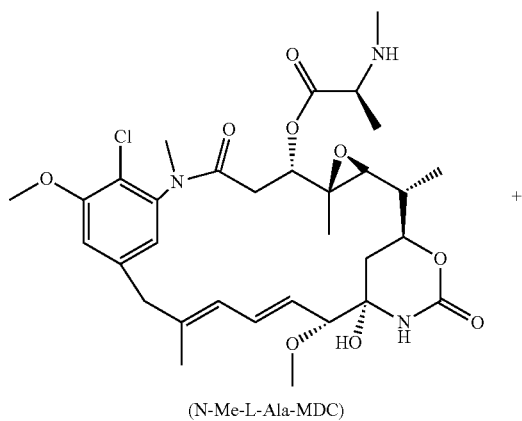

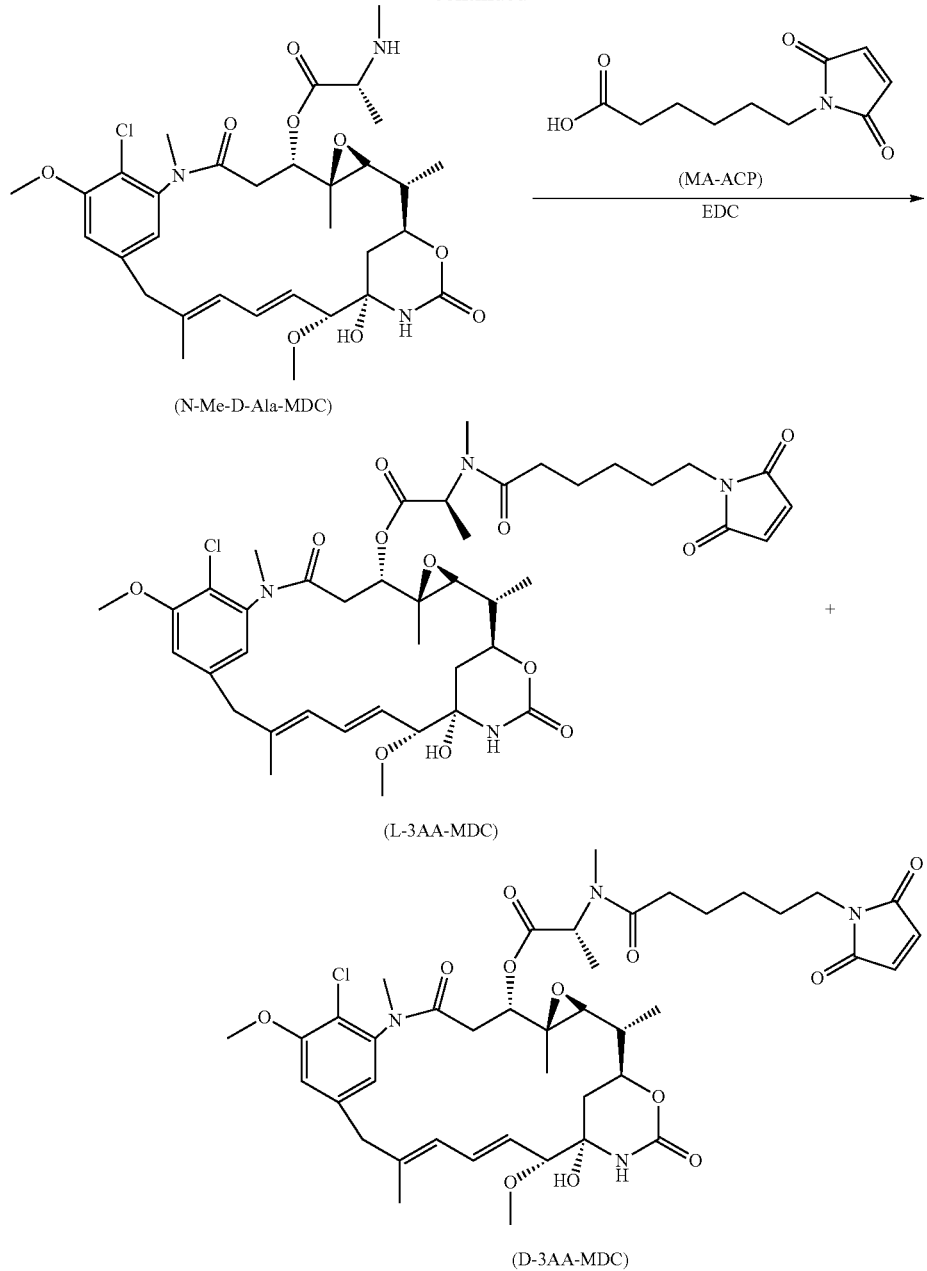

Into above prepared N-Me-D/L-Ala-MDC (0.5307 mmol) and MA-ACP (0.448 g, 2.123 mmol) in DMF (25 mL) under 0° C. was added EDC (0.407 g, 2.123 mmol). The mixture was stirred at r.t. overnight, quenched with water, extracted with EA, washed with brine, dried over $Na_2SO_4$. The solvent was removed under reduced pressure. Chromatography (silica gel: $CH_2Cl_2$/MeOH 30:1) gave the crude product. Further purification by preparative HPLC on a YMC C-18 column, 250×20 mm, S 10 μm) gave two fractions (Rt=6.59 min and 6.98 min) as white solid. The higher Rt fraction was determined to be the D-aminoacyl ester diastereomer (D-3AA-MDC, 45.2%), while the lower Rt fraction was the desired L-aminoacyl ester (L-3AA-MDC, 54.8%). L-3AA-MDC: white solid (0.1364 g, 30.5% overall yield over two steps), $^1$H NMR (400 MHz, $CDCl_3$): δ0.79 (3H, s), 1.17-1.32 (3H, m), 1.27 (3H, s), 1.29 (3H, s), 1.40-1.76 (7H, m), 2.12-2.23 (2H, m), 2.31-2.45 (1H, m), 2.59 (1H, t, J=12.8 Hz), 2.82 (3H, s), 3.01 (1H, d, J=9.6 Hz), 3.10 (1H, d, J=8.8 Hz), 3.17 (3H, s), 3.34 (3H, s), 3.42 (2H, t, J=6.8 Hz), 3.48 (2H, d, J=6.8 Hz), 3.62 (1H, d, J=12.8 Hz), 3.97 (3H, s), 4.27 (1H, t, J=11.2 Hz), 4.76 (1H, d, J=11.6 Hz), 5.36 (1H, q, J=6.8 Hz), 5.65 (1H, dd, J=15.2, 9.2 Hz), 6.25 (1H, s), 6.41 (1H, dd, J=15.2, 11.2 Hz), 6.64 (1H, s), 6.65 (2H, s), 6.72 (1H, d, J=11.2 Hz), 6.82 (1H, s). LC-MS (M+Na$^+$) calc.: 865.3. found: 865.3. Rt: 6.59 min. D-3AA-MDC: white solid (0.1128 g, 25.2% overall yield over two steps), $^1$H NMR (400 MHz, $CDCl_3$): δ0.86 (3H, s), 1.22-1.38 (4H, m), 1.25 (3H, d, J=9.2 Hz), 1.38-1.45 (1H, m), 1.48 (3H, d, J=7.6 Hz), 1.56-1.70 (4H, m), 1.68 (3H, s), 1.75 (1H, d, J=13.6 Hz), 2.19 (1H, dd, J=14.4, 2.8 Hz), 2.28-2.36 (2H, m), 2.65 (1H, dd, J=14.2, 12.0 Hz), 2.80 (1H, d, J=9.6 Hz), 3.01 (3H, s), 3.19 (1H, d, J=13.2 Hz), 3.32 (3H, s), 3.42 (1H, d, J=9.6 Hz), 3.47-3.54 (3H, m), 3.98 (3H, s), 4.29 (1H, t, J=10.4 Hz), 4.88 (1H, dd, J=11.8, 3.2 Hz), 5.07 (1H, q, J=7.6 Hz), 5.84 (1H, dd, J=15.2, 9.2 Hz), 6.23 (1H, d, J=11.2 Hz), 6.27 (1H, s), 6.41 (1H, dd, J=15.2, 11.2 Hz), 6.69 (2H, s), 6.79 (1H, d, J=1.2 Hz), 6.84 (1H, d, J=1.2 Hz). LC-MS (M+Na⁺) calc.: 865.3. found: 865.3. Rt: 6.98 min.

Example 17

Condensation of N-Me-L-Ala-MDC with MA-ACP (L-3AA-MDC)

(silica gel: CH$_2$Cl$_2$/MeOH 30:1) gave the crude product. Further purification by preparative HPLC on a YMC C-18 column, 250×20 mm, S 10 μm) gave the desired L-3AA-MDC: white solid (0.280 g, 62.6% overall yield over two steps), ¹H NMR (400 MHz, CDCl$_3$): δ0.79 (3H, s), 1.17-1.32 (3H, m), 1.27 (3H, s), 1.29 (3H, s), 1.40-1.76 (7H, m), 2.12-2.23 (2H, m), 2.31-2.45 (1H, m), 2.59 (1H, t, J=12.8 Hz), 2.82 (3H, s), 3.01 (1H, d, J=9.6 Hz), 3.10 (1H, d, J=8.8 Hz), 3.17 (3H, s), 3.34 (3H, s), 3.42 (2H, t, J=6.8 Hz), 3.48 (2H, d, J=6.8 Hz), 3.62 (1H, d, J=12.8 Hz), 3.97 (3H, s), 4.27 (1H, t, J=11.2 Hz), 4.76 (1H, d, J=11.6 Hz), 5.36 (1H, q, J=6.8 Hz), 5.65 (1H, dd, J=15.2, 9.2 Hz), 6.25 (1H, s), 6.41 (1H, dd, J=15.2, 11.2 Hz),

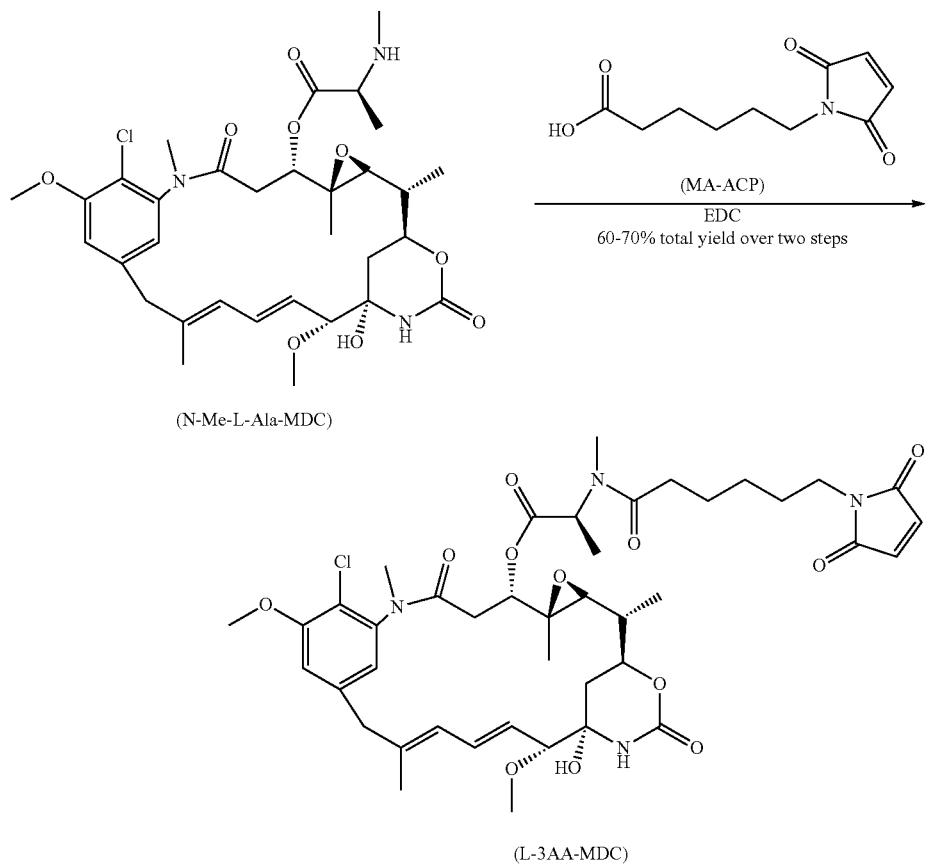

Into above prepared N-Me-L-Ala-MDC (0.5307 mmol) and MA-ACP (0.448 g, 2.123 mmol) in DMF (25 mL) under 0° C. was added EDC (0.407 g, 2.123 mmol). The mixture was stirred at r.t. overnight, quenched with water, extracted with EA, washed with brine, dried over Na$_2$SO$_4$. The solvent was removed under reduced pressure. Chromatography 6.64 (1H, s), 6.65 (2H, s), 6.72 (1H, d, J=11.2 Hz), 6.82 (1H, s). LC-MS (M+Na⁺) calc.: 865.3. found: 865.3. Rt: 6.59 min.

Example 18

Preparation of D-3AA-MDC and L-3AA-MDC

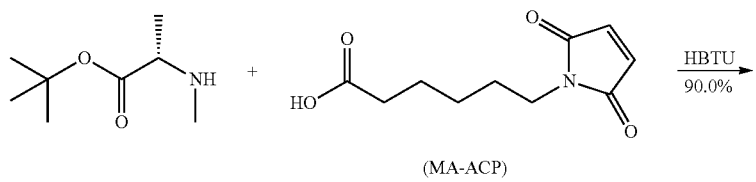

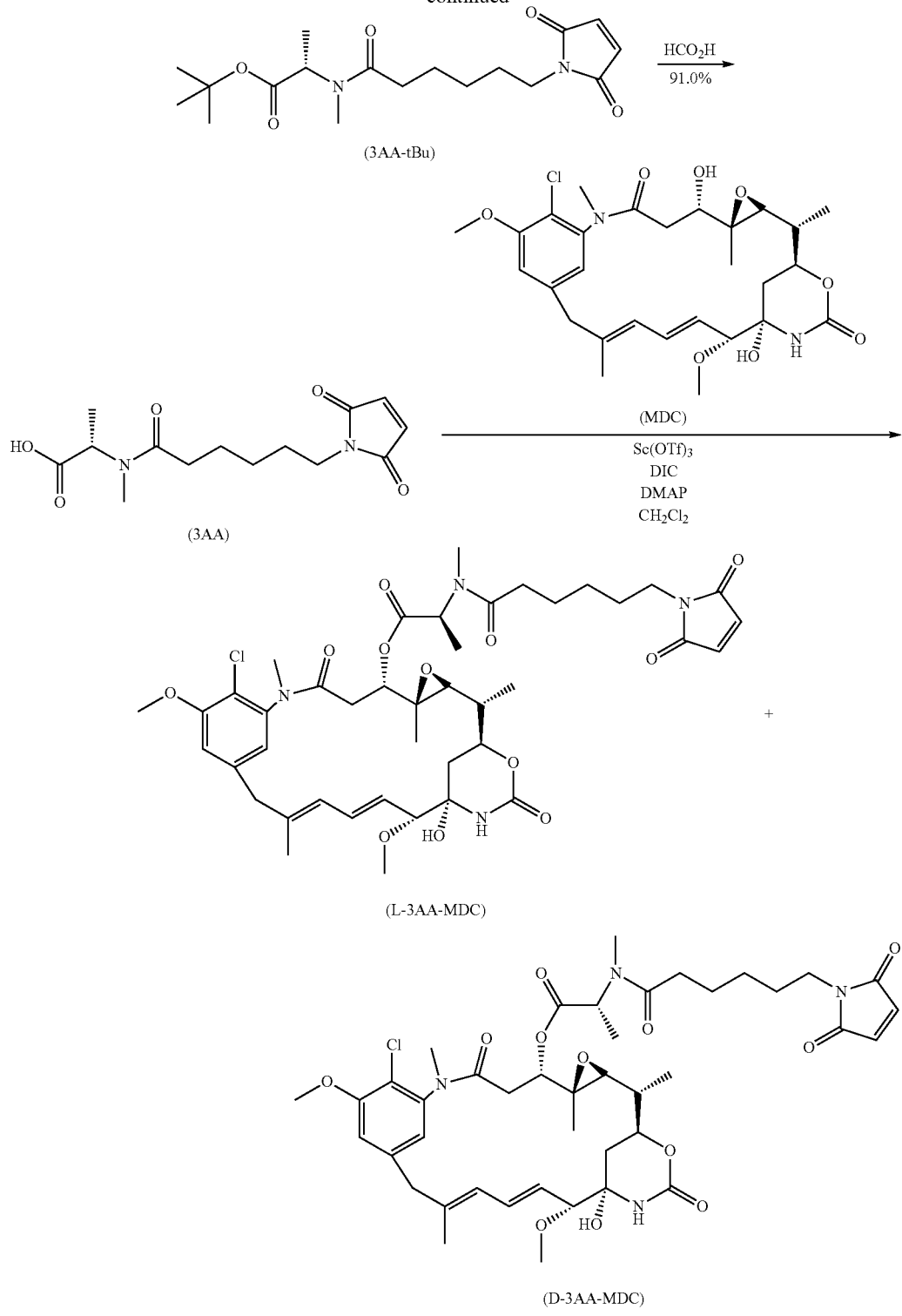

Step 1:

Into MA-ACP (1.0 g, 4.80 mmol) and t-Bu-N-Me-L-Ala (0.83 g, 5.28 mmol) in DMF (15 mL) was added HBTU (3.60 g, 9.60 mmol) and DIEA (1.84 g, 14.2 mmol). The mixture was stirred at r.t. for 5 h, quenched with water, and extracted with EtOAc. The organic phase was washed with brine, and dried over $Na_2SO_4$. The solvent was removed under reduced pressure. Chromatography (Silica gel, PE/EA 3:1) gave the product as an oil (1.52 g, 90.0%). $^1$H NMR (400 MHz, $CDCl_3$), δ 1.31-1.34 (4H, m), 1.43 (9H, s), 1.44 (3H, d, J=1.6 Hz), 1.66-1.69 (4H, m), 2.29-2.33 (2H, m), 2.90 (3H, s), 3.49-3.52 (2H, m), 5.13-5.18 (1H, m), 6.67 (2H, s). LC-MS (M+H$^+$) calc.: 353.2. found: 353.2. Rt: 6.61 min.

Step 2: Deprotection of t-Bu ester of 3AA-tBu (3AA)

Into 3AA-tBu (1.52 g, 4.313 mmol) was added formic acid (15 mL). The mixture was stirred overnight. The solvent was removed under reduced pressure. Chromatography (silica gel, CH$_2$Cl$_2$/MeOH 200:1) gave the product was colorless oil (1.16 g, 91.0%). $^1$H NMR (400 MHz, CDCl$_3$), δ 1.30-1.43 (4H, m), 1.49 (3H, d, J=7.2 Hz), 1.58-1.70 (4H, m), 2.33-2.38 (2H, m), 2.96 (3H, s), 3.50-3.54 (2H, m), 5.07-5.13 (1H, m), 6.68 (2H, s). LC-MS (M+H$^+$) calc.: 297.1. found: 297.1. Rt: 3.83 min.

Step 3: Esterification of Maytansinol with 3AA (L-3AA-MDC and D-3AA-MDC)

A mixture of maytansinol, 3AA (3-20 molar equiv.), Sc(OTf)$_3$ (0.6 molar equiv.) and DMAP (3.0 molar equiv.) in CH$_2$Cl$_2$ is stirred for 0.5 h at −8° C. DIC (1.1 molar equiv of 3AA) is added dropwise. The mixture is stirred for a few hours, quenched with diluted HCl and extracted with CH$_2$Cl$_2$. The combined organic phase is washed with aq. NaHCO$_3$, brine, and dried over anhydrous Na$_2$SO$_4$. The solvent is removed under reduced pressure. The product can be purified by column chromatography and preparative HPLC on a YMC C-18 column (250×20 mm, S 10 μm).

Example 19

The following compounds can be prepared using a method similar to those described herein:

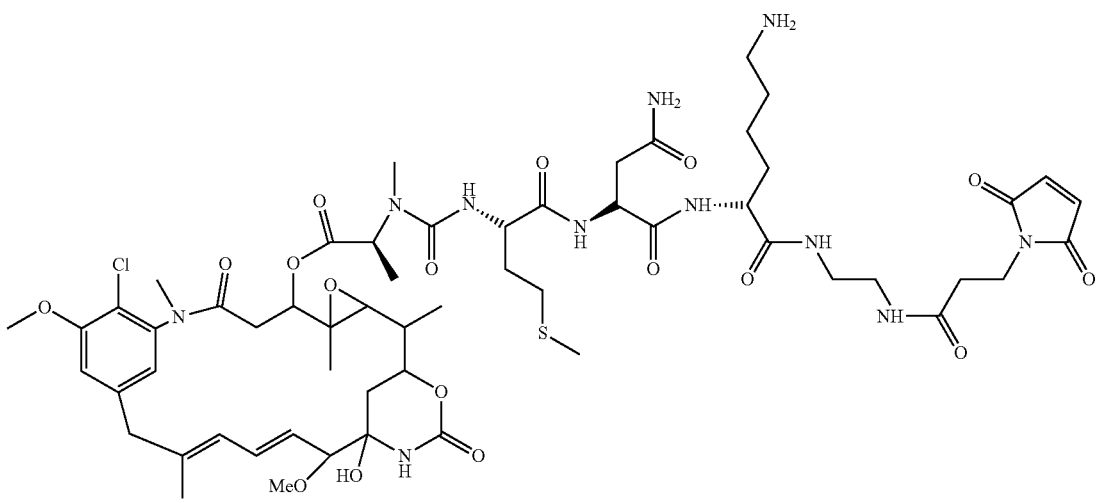

Maleimido-Pro-EDA-D-Lys-L-Asn-L-Met-Maytansine

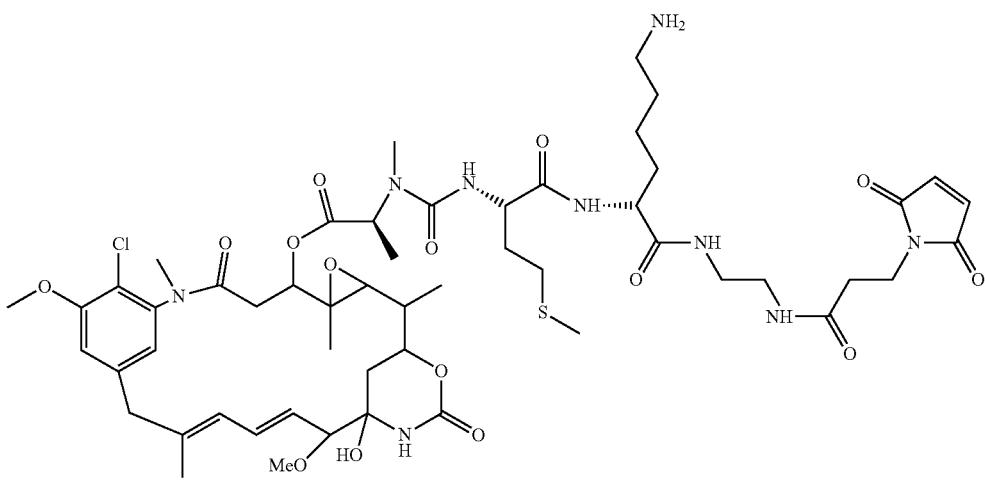

Maleimido-Pro-EDA-D-Lys-L-Met-Maytansine

-continued
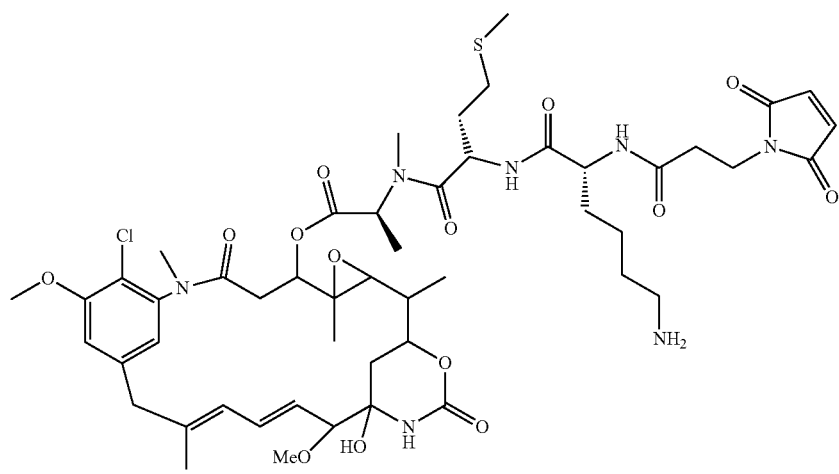
Maleimido-Pro-D-Lys-L-Met-Maytansine
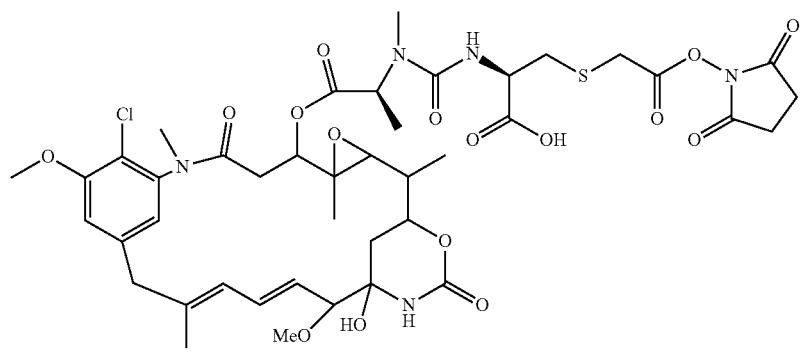
Su-Ac-L-Cys-Maytansine
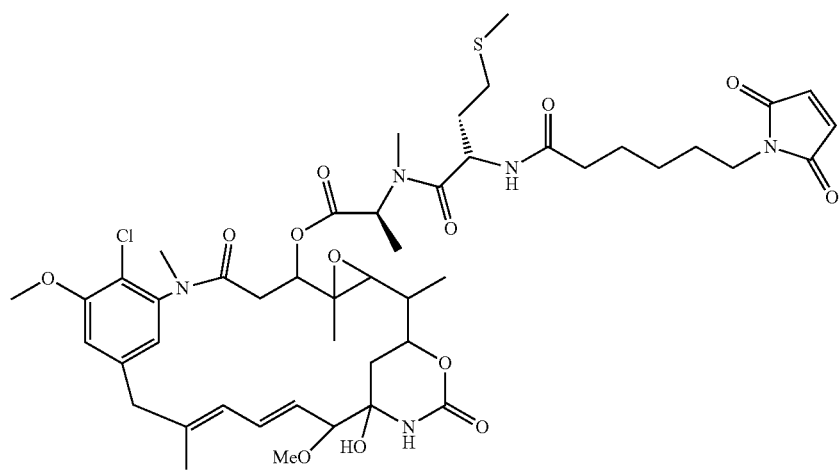
Maleimido-Cap-L-Met-Maytansine

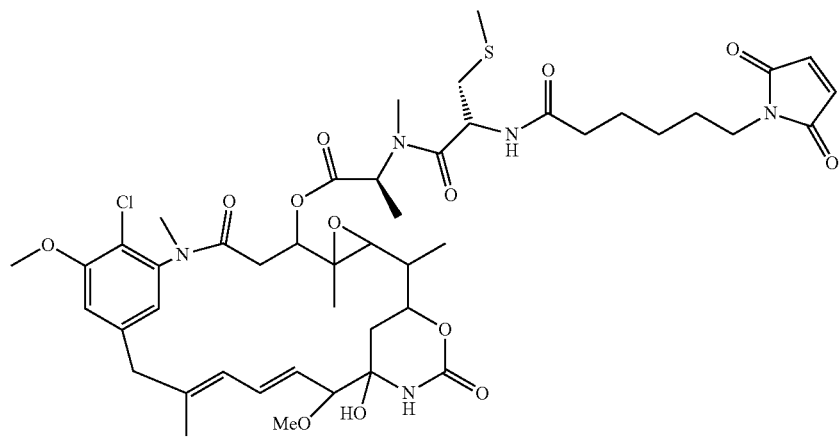
Maleimido-Cap-S-Me-L-Cys-Maytansine
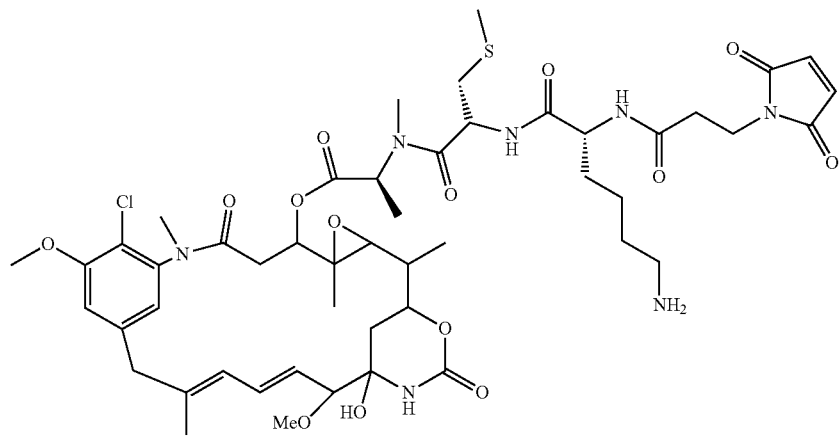
Maleimido-Pro-D-Lys-S-Me-L-Cys-Maytansine
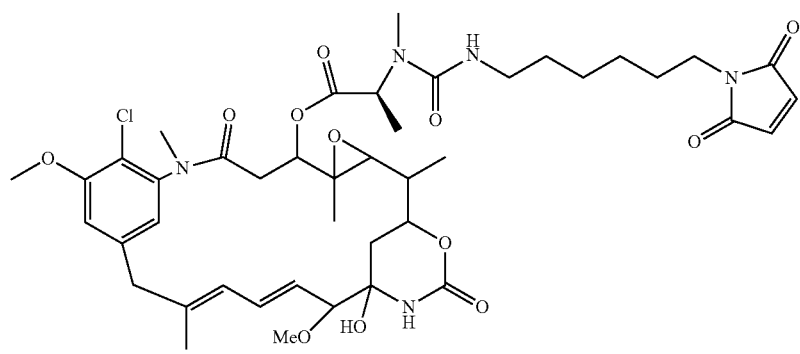
Maleimido-HDA-Maytansine

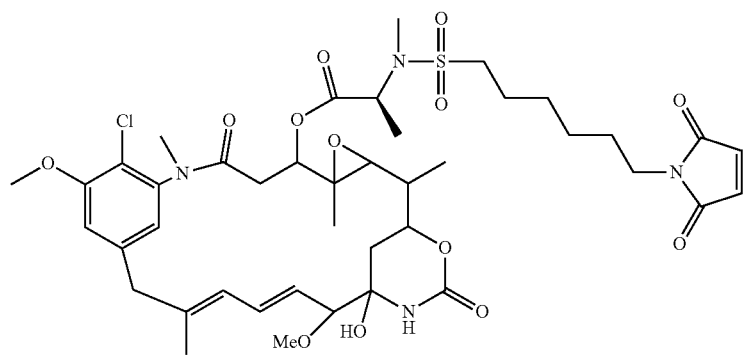
Maleimido-HDA-SO$_2$-Maytansine
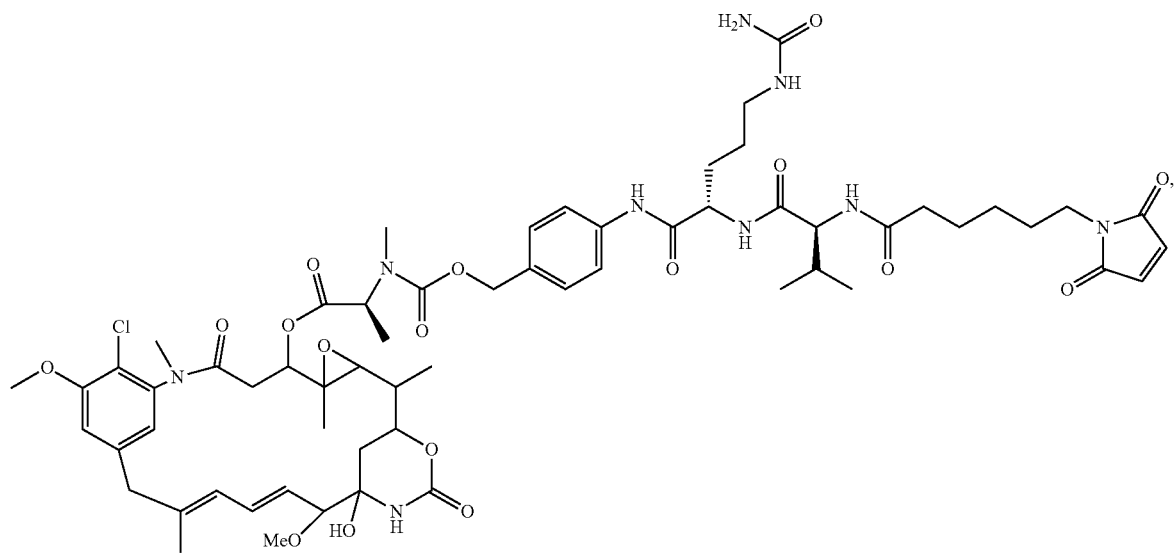
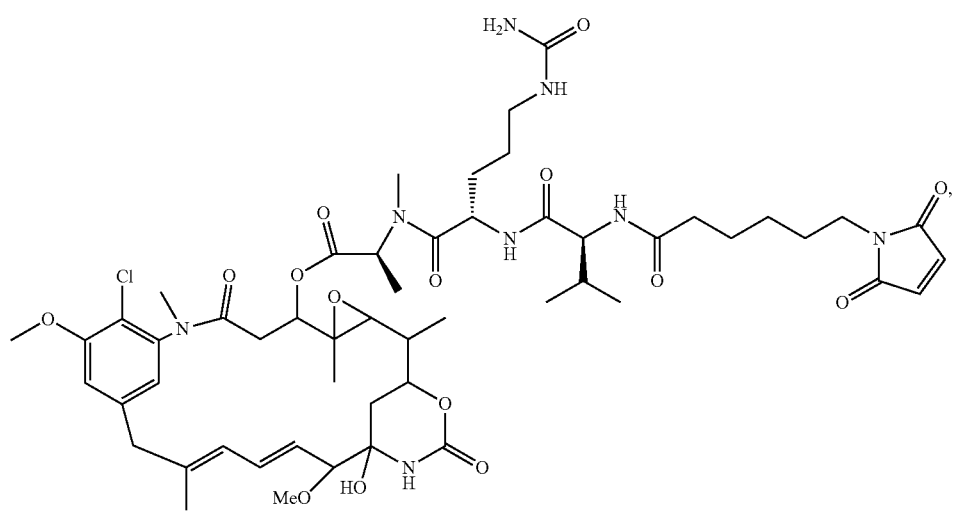

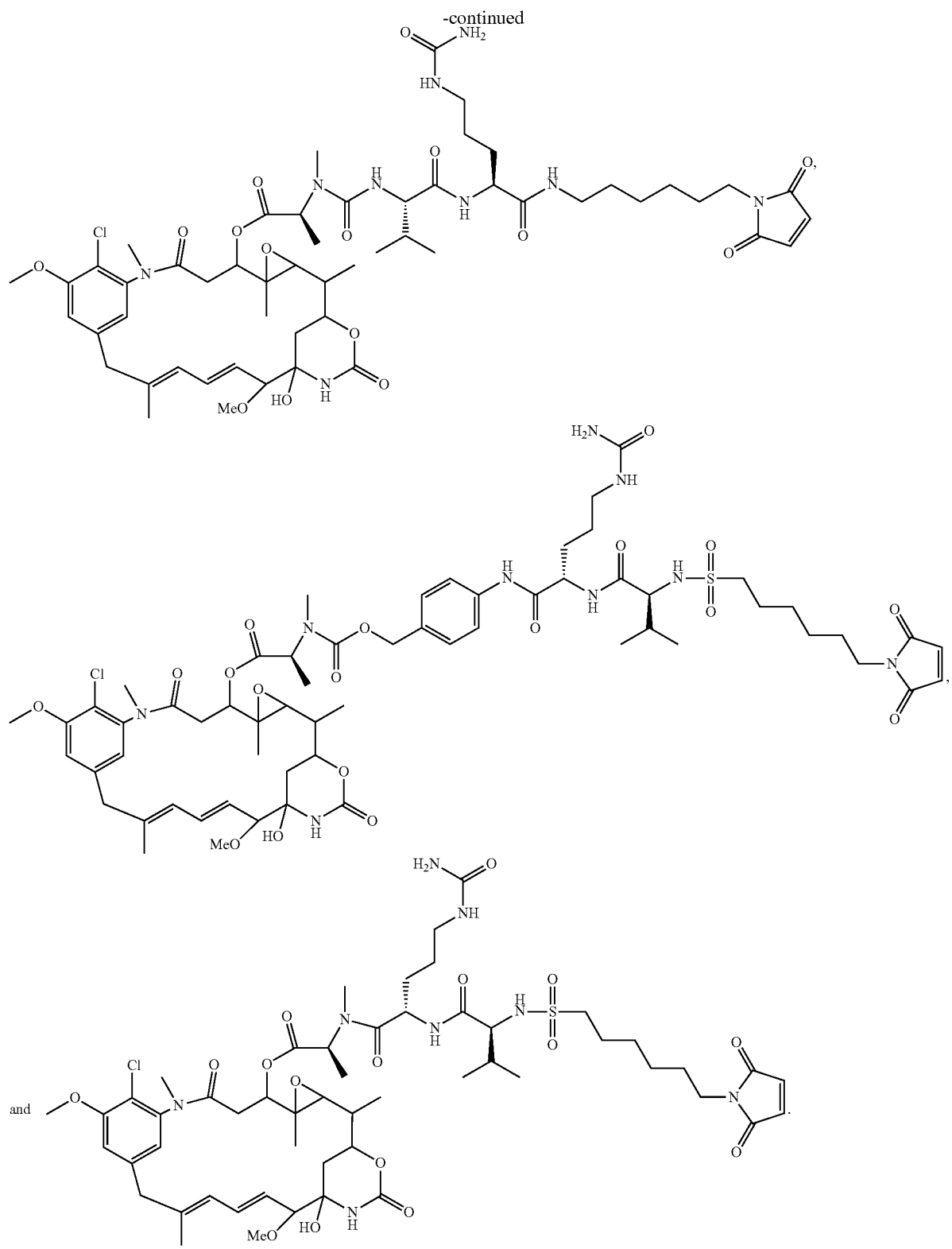

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

All references cited herein are incorporated by reference in their entirety and for all purposes to the same extent as if each individual publication or patent or patent application was specifically and individually indicted to be incorporated by reference in its entirety for all purposes.

What is claimed is:

1. A method of preparing a compound of Formula I or a salt thereof:

I comprising contacting a compound of Formula I-A:

I-A with a carboxylic acid of the formula R—COOH in the presence of a coupling reagent, a rare earth metal-based or trifluoromethanesulfonate-based Lewis acid catalyst and a base to form the compound of Formula I, or a salt thereof;

wherein

X is hydrogen or halo;

Y is selected from the group consisting of hydrogen, $C_1$-$C_6$ alkyl, $C_3$-$C_6$ cycloalkyl, and —C(=O)$R^5$;

$R^1$ is selected from the group consisting of hydrogen, — and —O$R^{17}$;

$R^2$ is hydrogen or $C_1$-$C_6$ alkyl;

$R^3$ is methyl, —CH$_2$OH, or —CH$_2$O$R^{17}$;

$R^4$ is —OH, —O$R^{17}$ or —SH;

$R^5$ is $C_1$-$C_6$ alkyl or benzyl;

$R^{17}$ is a hydroxy protecting group;

R is selected from the group consisting of alkyl, aryl, cycloalkyl, cycloalkenyl, heteroaryl, and heterocyclic, wherein the alkyl, aryl, cycloalkyl, cycloalkenyl, heteroaryl, or heterocyclic is optionally substituted with one to three $R^{10}$, or is L is selected from optionally substituted $C_1$-$C_{20}$ alkylene, $C_3$-$C_8$ cycloalkylene, and optionally substituted $C_1$-$C_{20}$ alkylene wherein one or more of the —CH$_2$— group is independently replaced with $C_3$-$C_8$ cycloalkylene, —O—, —S—, —C(O)—, —NR$^8$—, —C(=O)NR$^8$—, —NR$^8$C(=O)—, —SO$_2$NR$^8$—, or —NR$^8$SO$_2$—;

substituted $C_1$-$C_{20}$ alkylene is $C_1$-$C_{20}$ alkylene substituted with 1 to 4 —SO$_3$H, —P(O)(OH)$_2$ or $R^{23}$, wherein each $R^{23}$ is independently $C_{1-6}$ alkyl optionally substituted with 1 or 2 substituents independently selected from the group consisting of SH, S—$C_{1-4}$ alkyl, —CONR$^{11}$R$^{11}$, and —NR$^{11}$Pr;

$R^7$ is hydrogen, $C_1$-$C_6$ alkyl or an amino acid side chain;

$R^8$ is hydrogen or $C_{1-6}$ alkyl;

each $R^{10}$ is independently selected from the group consisting of —NR$^{11}$Pr, —NR$^{11}$COCH$_2$Br, —COOR$^{12}$, —CONR$^{11}$R$^{11}$, —NR$^{11}$COR$^{13}$, —S—S—$R^{13}$, —Si($R^{13}$)$_3$, alkyl, aryl, cycloalkyl, cycloalkenyl, heteroaryl, and heterocyclic;

each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo;

Pr is an amino protecting group;

$R^{12}$ is $C_1$-$C_6$ alkyl, or benzyl; and each $R^{13}$ is independently selected from the group consisting of alkyl, aryl, cycloalkyl, heteroaryl, and heterocyclic.

2. The method of claim 1, wherein the compound of Formula I is the isomer and
the compound of Formula I-A is the isomer

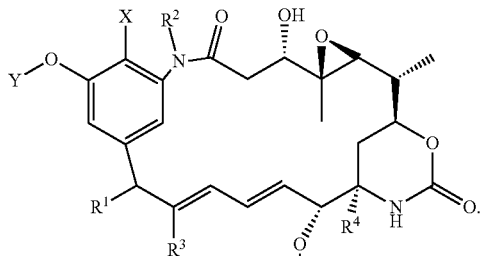

3. The method of claim 1, wherein the compound of formula I is:

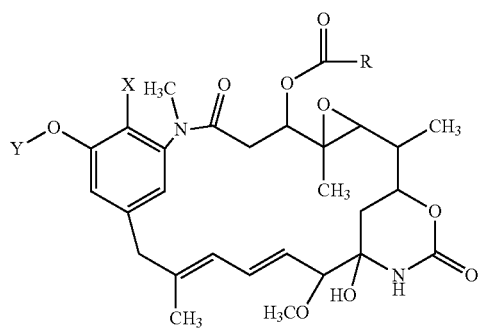

and the compound of formula I-A is:

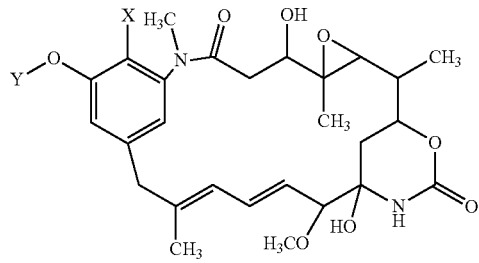

wherein X is hydrogen or Cl, Y is hydrogen or methyl, and R is as defined in claim 1.

4. The method of claim 3, wherein the compound of formula I is the isomer:

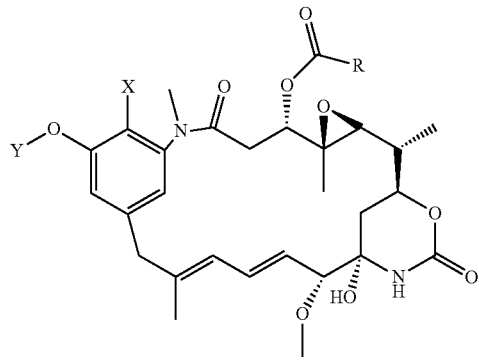

and the compound of formula I-A is the isomer:

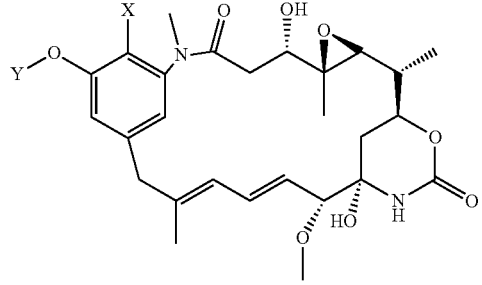

wherein X is hydrogen or Cl, Y is hydrogen or methyl, and R is as defined in claim 1.

5. The method of claim 1, wherein the compound of formula I is:

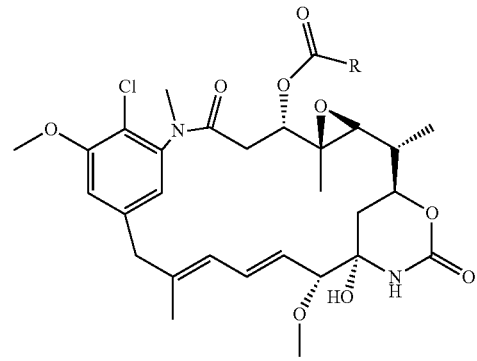

and the compound of formula I-A is:

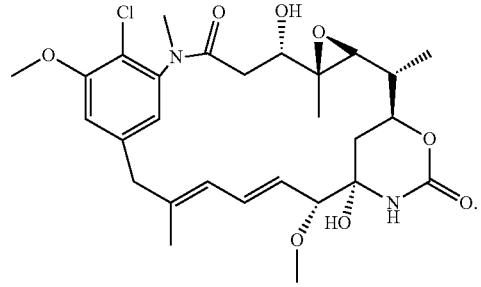

6. A method of preparing a compound of Formula II, or a salt thereof:

comprising contacting a compound of Formula II-A:

with a carboxylic acid of the formula R—COOH in the presence of a coupling reagent, a rare earth metal-based or trifluoromethanesulfonate-based Lewis acid catalyst and a base to form the compound of Formula II, or a salt thereof;
wherein
X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, and —$OR^{17}$;
$R^2$ is hydrogen or $C_1$-$C_6$ alkyl;
$R^3$ is methyl, —$CH_2OH$, or $CH_2OR^{17}$;
$R^4$ is —OH, —$OR^{17}$ or —SH;
$R^5$ is $C_1$-$C_6$ alkyl or benzyl;
$R^{17}$ is a hydroxy protecting group;
R is selected from the group consisting of alkyl, aryl, cycloalkyl, cycloalkenyl, heteroaryl, and heterocyclic, wherein the alkyl, aryl, cycloalkyl, cycloalkenyl, heteroaryl, or heterocyclic is optionally substituted with one to three $R^{10}$, or is L is selected from optionally substituted $C_1$-$C_{20}$ alkylene, $C_3$-$C_8$ cycloalkylene, and optionally substituted $C_1$-$C_{20}$ alkylene wherein one or more of the —$CH_2$— group is independently replaced with $C_3$-$C_8$ cycloalkylene, —O—, —S—, —C(O)—, —$NR^8$—, —C(=O)$NR^8$—, —$NR^8$C(=O)—, —$SO_2NR^8$—, or —$NR^8SO_2$—;

wherein substituted $C_1$-$C_{20}$ alkylene is $C_1$-$C_{20}$ alkylene substituted with 1 to 4 —$SO_3H$, —P(O)(OH)$_2$ or $R^{23}$, wherein each $R^{23}$ is independently $C_{1-6}$ alkyl optionally substituted with 1 or 2 substituents independently selected from the group consisting of SH, S—$C_{1-4}$ alkyl, —$CONR^{11}R^{11}$, and —$NR^{11}Pr$;

$R^7$ is hydrogen, $C_1$-$C_6$ alkyl or an amino acid side chain;
$R^8$ is hydrogen or $C_{1-6}$ alkyl;
each $R^{10}$ is independently selected from the group consisting of —$NR^{11}Pr$, —$NR^{11}COCH_2Br$, —$COOR^{12}$, —$CONR^{11}R^{11}$, —$NR^{11}COR^{13}$, —S—S—$R^{13}$, —Si($R^{13}$)$_3$, alkyl, aryl, cycloalkyl, cycloalkenyl, heteroaryl, and heterocyclic;

each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo;

Pr is an amino protecting group;
$R^{12}$ is $C_1$-$C_6$ alkyl, or benzyl; and
each $R^{13}$ is independently selected from the group consisting of alkyl, aryl, cycloalkyl, heteroaryl, and heterocyclic.

7. The method of claim 6, wherein the compound of Formula II is and
the compound of Formula II-A is

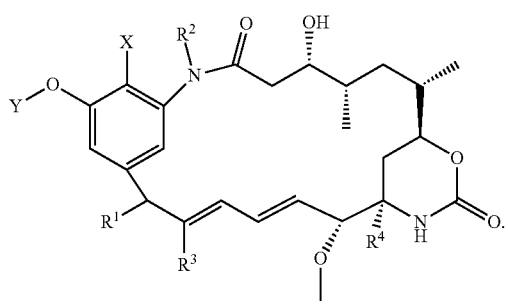

8. The method of claim 1, wherein R—COOH is

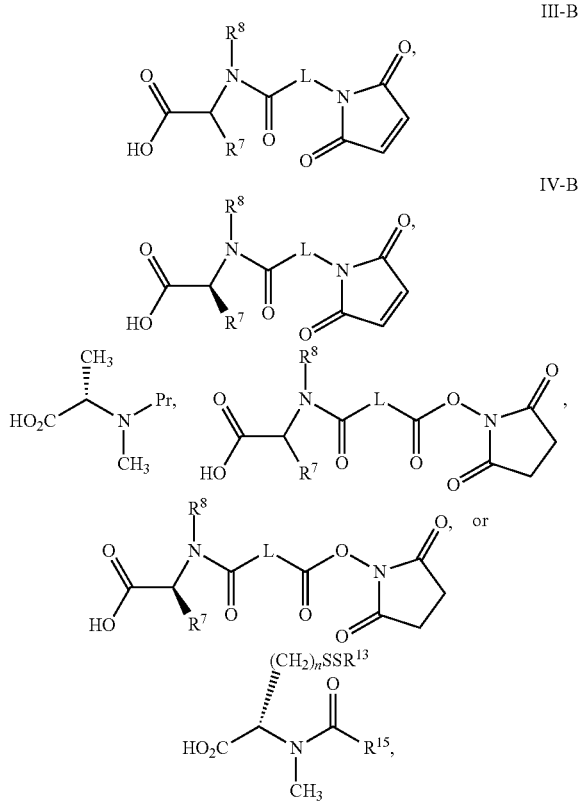

wherein
$R^7$ is hydrogen, $C_1$-$C_6$ alkyl or an amino acid side chain;
$R^8$ is hydrogen or $C_{1-6}$ alkyl;
$R^{13}$ is $C_1$-$C_6$ alkyl or heteroaryl;
$R^{15}$ is $C_1$-$C_6$ alkyl, or aryl;
n is 1 or 2; and
L is selected from optionally substituted $C_1$-$C_{20}$ alkylene, $C_3$-$C_8$ cycloalkylene, optionally substituted $C_1$-$C_{20}$ alkylene wherein one or more of the —$CH_2$— group is independently replaced with $C_3$-$C_8$ cycloalkylene, —O—, —S—, —C(O)—, —$NR^8$—, —C(=O)$NR^8$—, —$NR^8$C(=O)—, —$SO_2NR^8$—, or —$NR^8SO_2$—; wherein substituted $C_1$-$C_{20}$ alkylene is $C_1$-$C_{20}$ alkylene substituted with 1 to 4 —$SO_3H$, —P(O)(OH)$_2$ or $R^{23}$, wherein each $R^{23}$ is independently $C_{1-6}$ alkyl optionally substituted with 1 or 2 substituents independently selected from the group consisting of SH, S—$C_{1-4}$ alkyl, —$CONR^{11}R^{11}$, and —$NR^{11}$Pr.

9. The method of claim 1, wherein R—COOH is $CH_3COOH$, $(CH_3)_2CHCOOH$, $(CH_3)_3Si(CH_2)_2OC(=O)(CH_2)_4COOH$,

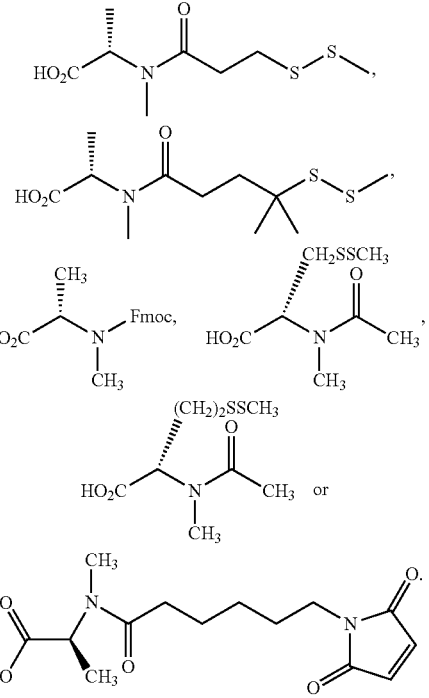

10. The method of claim 1, wherein R—COOH is an amino acid or amino acid derivative wherein the amino group is protected by a Pr group.

11. The method of claim 1, wherein R—COOH is N-methyl-L-alanine, L-cysteine or L-methionine, wherein the amino group is protected by a Pr group.

12. A method of preparing a compound of Formula III, or a salt thereof:

III

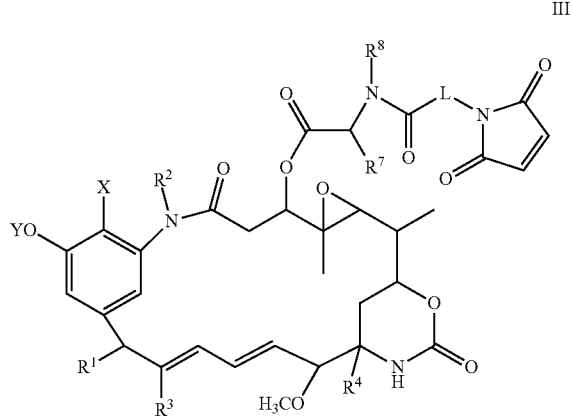

comprising contacting a compound of Formula III-A:

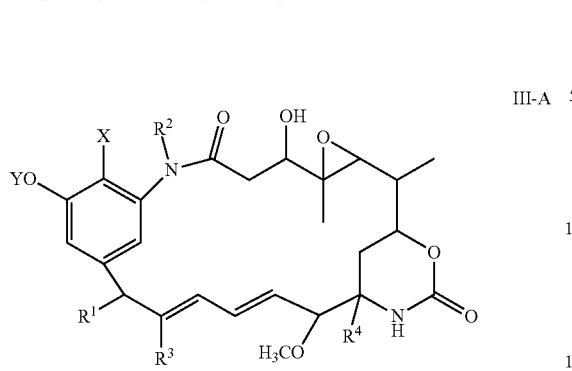

III-A with a carboxylic acid of Formula III-B

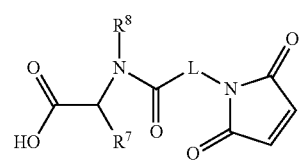

III-B in the presence of a coupling reagent, a rare earth metal-based or trifluoromethanesulfonate-based Lewis acid catalyst and a base to form the compound of Formula III, or a salt thereof;

wherein

X is hydrogen or halo;

Y is selected from the group consisting of hydrogen, $C_1$-$C_6$ alkyl, $C_3$-$C_6$ cycloalkyl, and —C(=O)$R^5$;

$R^1$ is selected from the group consisting of hydrogen, —OH, and —O$R^{17}$;

$R^2$ is hydrogen or $C_1$-$C_6$ alkyl;

$R^3$ is methyl, —CH$_2$OH, or CH$_2$O$R^{17}$;

$R^4$ is —OH, —O$R^{17}$ or —SH;

$R^5$ is $C_1$-$C_6$ alkyl or benzyl;

$R^{17}$ is a hydroxy protecting group;

$R^7$ is hydrogen, $C_1$-$C_6$ alkyl or an amino acid side chain;

$R^8$ is hydrogen or $C_{1-6}$ alkyl; and

L is selected from optionally substituted $C_1$-$C_{20}$ alkylene, $C_3$-$C_8$ cycloalkylene, and optionally substituted $C_1$-$C_{20}$ alkylene wherein one or more of the —CH$_2$— group is independently replaced with $C_3$-$C_8$ cycloalkylene, —O—, —S—, —C(O)—, —N$R^8$—, —C(=O)N$R^8$—, —N$R^8$C(=O)—, —SO$_2$N$R^8$—, or —N$R^8$SO$_2$—; wherein substituted $C_1$-$C_{20}$ alkylene is $C_1$-$C_{20}$ alkylene substituted with 1 to 4 —SO$_3$H, —P(O)(OH)$_2$ or $R^{23}$, wherein each $R^{23}$ is independently $C_{1-6}$ alkyl optionally substituted with 1 or 2 substituents independently selected from the group consisting of SH, S—$C_{1-4}$ alkyl, —CON$R^{11}R^{11}$, and —N$R^{11}$Pr.

13. The method of claim 12, wherein the compound of Formula III is the isomer:

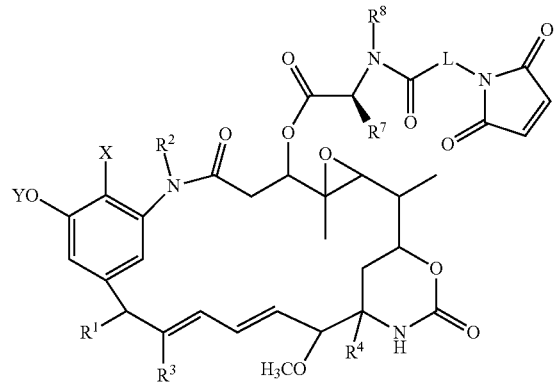

and the carboxylic acid of Formula III-B is the isomer IV-B:

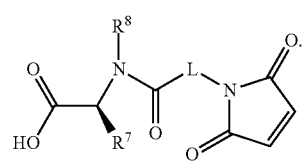

IV-B

14. The method of claim 12, wherein the compound of Formula III is the isomer:

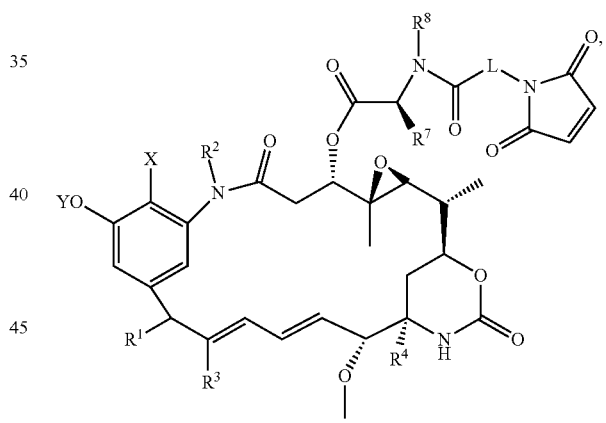

the compound of formula III-A is the isomer:

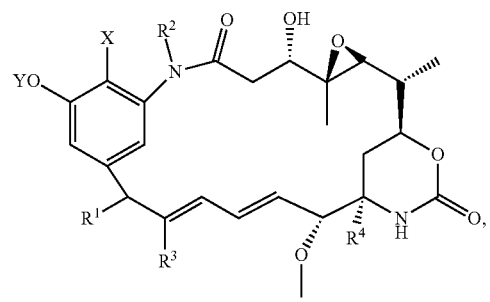

and the carboxylic acid of Formula III-B is the isomer IV-B:

IV-B
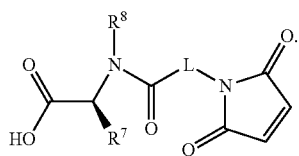

and the carboxylic acid is of Formula IV-B

IV-B
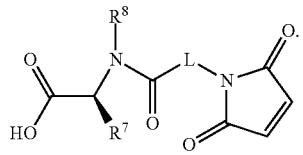

15. The method of claim 12, wherein the compound of Formula III is a compound of Formula V, or a salt thereof:

16. The method of claim 15, wherein the compound of Formula V is the isomer:

V
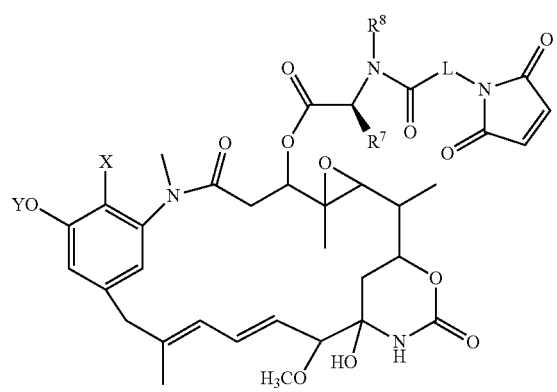

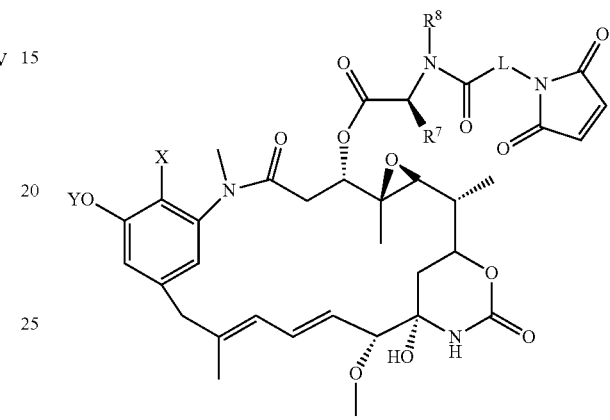

the compound of Formula III-A is a compound of Formula V-A:

and
the compound of Formula V-A is the isomer:

V-A
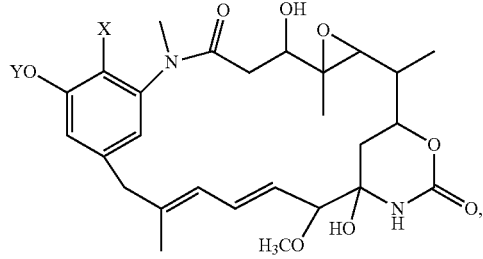

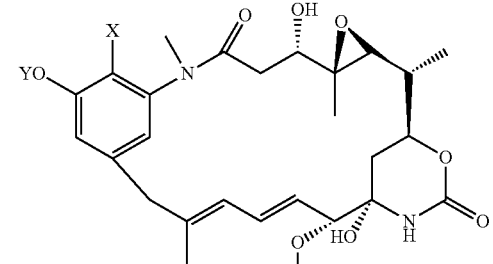

17. The method of claim 12, wherein the compound of Formula III is a compound of Formula VII, or a salt thereof:

VII
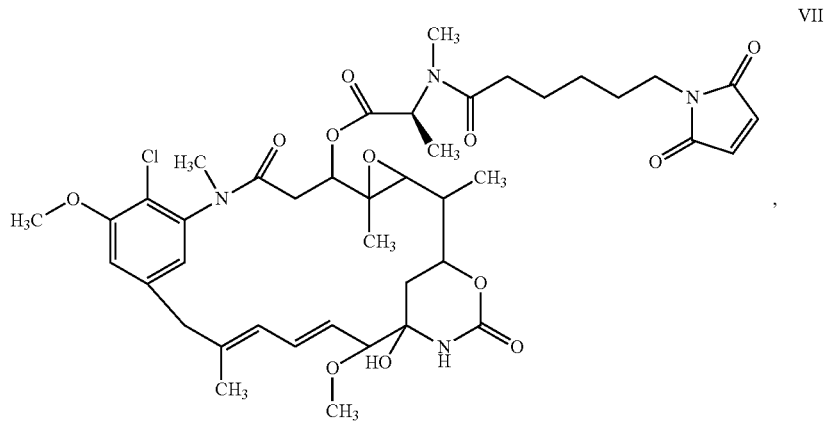 [SMILES: COc1cc2cc(c1Cl)N(C)C(=O)CC(OC(=O)[C@H](C)N(C)C(=O)CCCCCN1C(=O)C=CC1=O)C1(C)OC1C(C)C1CC(O)(NC(=O)O1)C(OC)/C=C/C=C(\C)C2]

the compound of Formula III-A is a compound of Formula VII-A:

VII-A

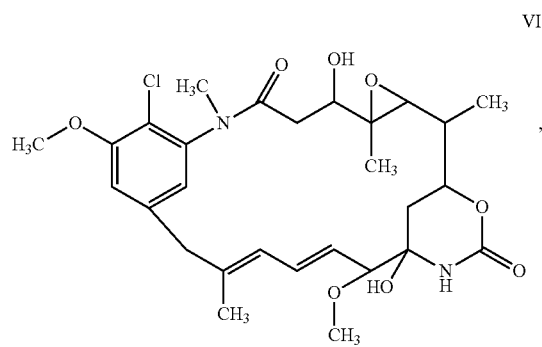

and the carboxylic acid is of Formula VII-B

VII-B

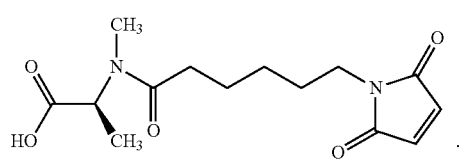

18. The method of claim 17, wherein the compound of Formula VII is the isomer:

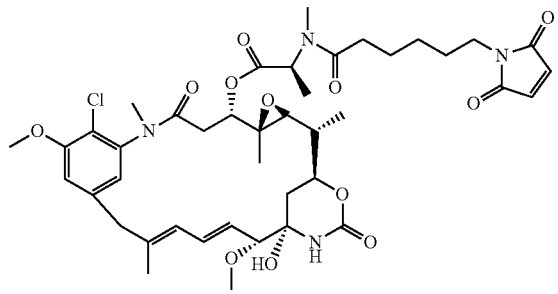

and the compound of formula VII-A is the isomer:

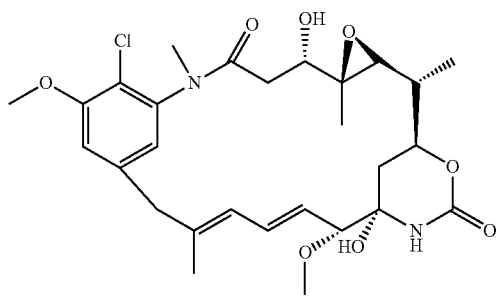

19. The method for preparing a compound of Formula IV, or a salt thereof:

IV

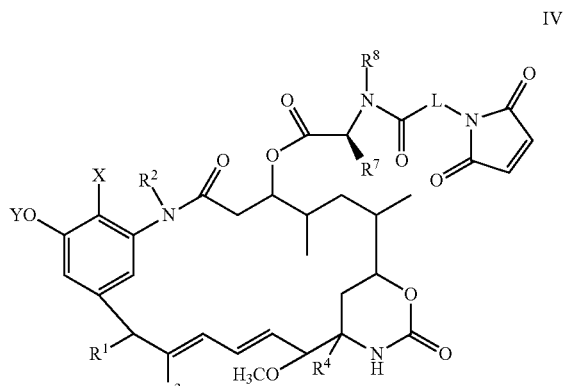

comprising contacting a compound of Formula IV-A:

IV-A

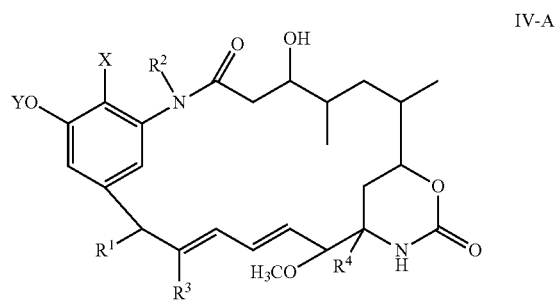

with a carboxylic acid of the formula IV-B

IV-B

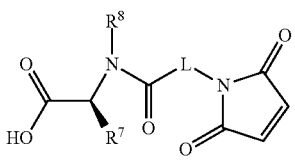

in the presence of a coupling reagent, a rare earth metal-based or trifluoromethanesulfonate-based Lewis acid catalyst and a base to form the compound of Formula IV, or a salt thereof;
wherein
X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, and —O$R^{17}$;
$R^2$ is hydrogen or $C_1$-$C_6$ alkyl;
$R^3$ is methyl, —CH$_2$OH, or CH$_2$O$R^{17}$;
$R^4$ is —OH, —O$R^{17}$ or —SH;
$R^5$ is $C_1$-$C_6$ alkyl or benzyl;
$R^{17}$ is a hydroxy protecting group;
$R^7$ is hydrogen, $C_1$-$C_6$ alkyl or an amino acid side chain;
$R^8$ is hydrogen or $C_{1-6}$ alkyl; and
L is selected from optionally substituted $C_1$-$C_{20}$ alkylene, $C_3$-$C_8$ cycloalkylene, and optionally substituted $C_1$-$C_{20}$ alkylene wherein one or more of the —CH$_2$— group is independently replaced with $C_3$-$C_8$ cycloalkylene, —O—, —S—, —C(O)—, —NR$^8$—, —C(=O)NR$^8$—, —NR$^8$C(=O)—, —SO$_2$NR$^8$—, or —NR$^8$SO$_2$—; wherein substituted $C_1$-$C_{20}$ alkylene is $C_1$-$C_{20}$ alkylene substituted with 1 to 4 —SO$_3$H, —P(O)(OH)$_2$ or R$^{23}$, wherein each R$^{23}$ is independently $C_{1-6}$ alkyl optionally substituted with 1 or 2 substituents independently selected from the group consisting of SH, S—$C_{1-4}$ alkyl, —CONR$^{11}$R$^{11}$, —NR$^{11}$Pr.

20. The method of claim 19, wherein the compound of Formula IV is the isomer:

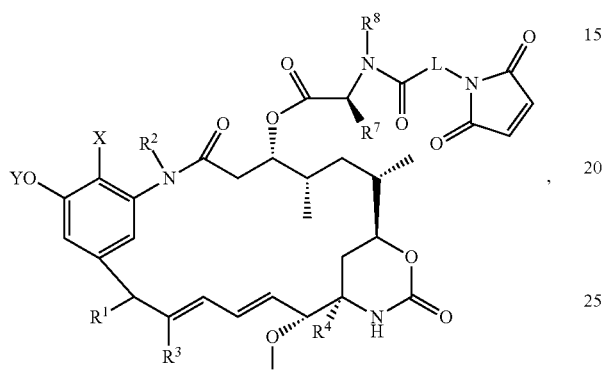

the compound of formula IV-A is the isomer:

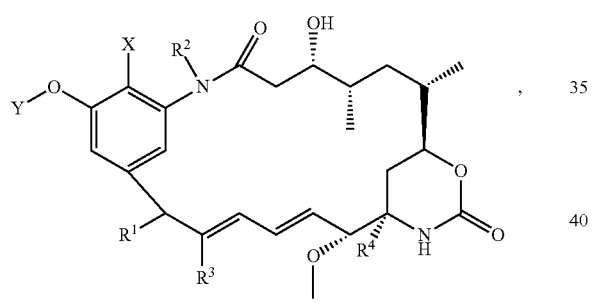

and the carboxylic acid of the formula III-B is the isomer IV-B:

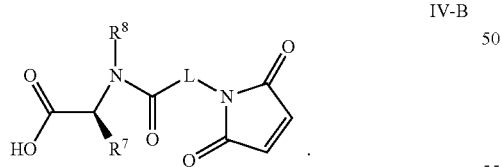

21. The method of claim 1, wherein X is halo.
22. The method of claim 1, wherein Y is $C_1$-$C_6$ alkyl.
23. The method of claim 1, wherein R$^1$ is hydrogen and R$^2$ is hydrogen or methyl.
24. The method of claim 1, wherein R$^3$ is methyl.
25. The method of claim 1, wherein R$^4$ is —OH.
26. The method of claim 1, wherein L is $C_1$-$C_{20}$ alkylene.
27. The method of claim 1 or 6, wherein the Lewis acid catalyst is a lanthanide compound.
28. The method of claim 1 or 6, wherein the Lewis acid catalyst is a trifluoromethanesulfonate (triflate) compound.
29. The method of claim 1 or 6, wherein the Lewis acid catalyst is a lanthanide trifluoromethanesulfonate (lanthanide triflate or Ln(OTf)$_3$).
30. The method of claim 1 or 6, wherein the Lewis acid catalyst is scandium triflate (Sc(OTf)$_3$).
31. The method of claim 1 or 6, wherein the base is 4-dialkylaminopyridine.
32. The method of claim 1 or 6, wherein the coupling reagent is dicyclohexylcarbodiimide, diisopropylcarbodiimide, or 1-ethyl-3-(3-dimethylaminopropyl)-dicarbodiimide.

33. A method of preparing a compound of Formula X

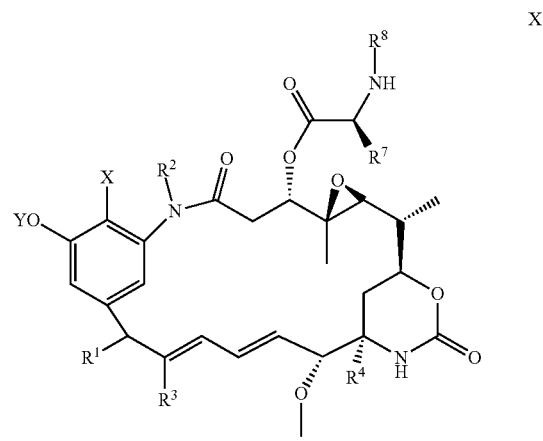

comprising deprotection of a compound of Formula X-A:

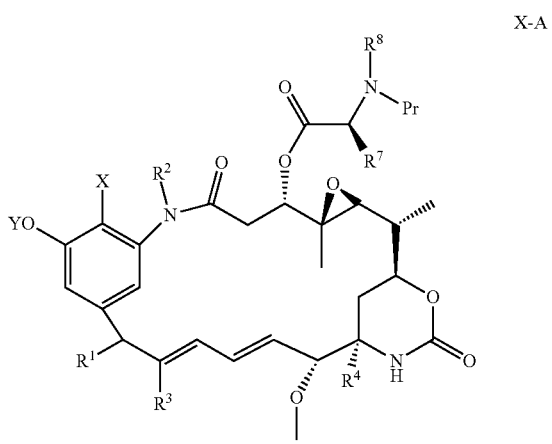

wherein
X is hydrogen or halo;
Y is selected from the group consisting of hydrogen, $C_1$-$C_6$ alkyl, $C_3$-$C_6$ cycloalkyl, and —C(=O)R$^5$;
R$^1$ is selected from the group consisting of hydrogen, —OH, and —OR$^{17}$;
R$^2$ is hydrogen or $C_1$-$C_6$ alkyl;
R$^3$ is methyl, —CH$_2$OH, or —CH$_2$OR$^{17}$;
R$^4$ is —OH, —OR$^{17}$ or —SH;
R$^5$ is $C_1$-$C_6$ alkyl or benzyl;
R$^{17}$ is a hydroxy protecting group;
R$^7$ is hydrogen, $C_1$-$C_6$ alkyl or an amino acid side chain;
R$^8$ is hydrogen or $C_{1-6}$ alkyl; and
Pr is Fmoc.

34. A method of preparing a compound of Formula XI, or a salt thereof:

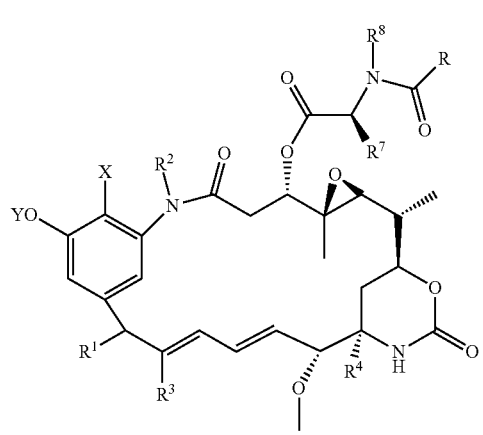

XI or a salt thereof,
comprising contacting a compound of Formula X:

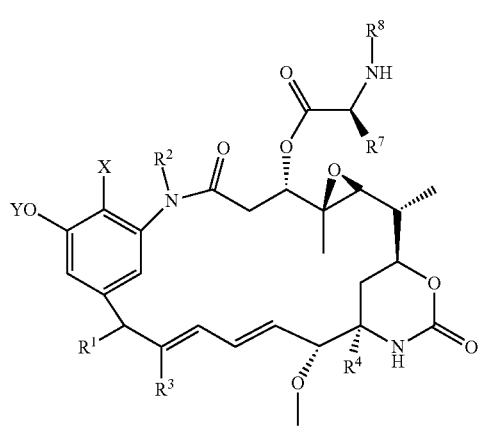

X with a carboxylic acid of Formula III-G

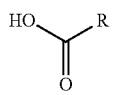

III-G in the presence of a coupling reagent or directly with its active ester to form the compound of Formula XI, or a salt thereof;
wherein
X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, and —OR$^{17}$;
$R^2$ is hydrogen or $C_1$-$C_6$ alkyl;
$R^3$ is methyl, —CH$_2$OH, or —CH$_2$OR$^{17}$;
$R^4$ is —OH, —OR$^{17}$ or —SH;
$R^5$ is $C_1$-$C_6$ alkyl or benzyl;
$R^{17}$ is a hydroxy protecting group;
$R^7$ is hydrogen, $C_1$-$C_6$ alkyl or an amino acid side chain;
$R^8$ is hydrogen or $C_{1-6}$ alkyl; and
R is hydrogen, alkyl, aryl, cycloalkyl, cycloalkenyl, heteroaryl.

35. A method of preparing a compound of Formula XII:

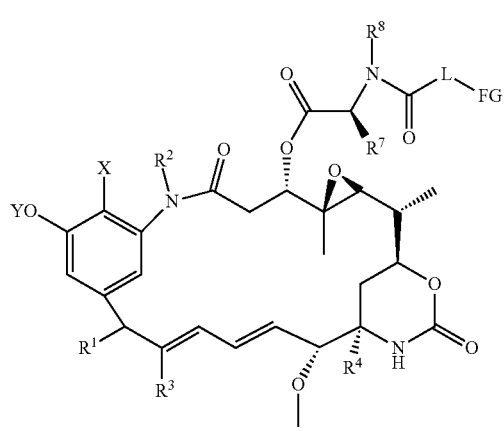

XII or a salt thereof,
comprising contacting a compound of Formula X:

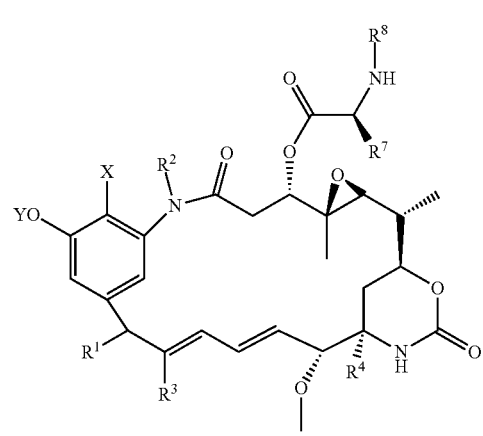

X with a carboxylic acid of Formula III-H

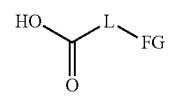

III-H in the presence of a coupling reagent or directly with its active ester to form the compound of Formula XII, or a salt thereof;
wherein
X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, and —OR$^{17}$;
$R^2$ is hydrogen or $C_1$-$C_6$ alkyl;
$R^3$ is methyl, —CH$_2$OH, or —CH$_2$OR$^{17}$;
$R^4$ is —OH, —OR$^{17}$ or —SH;
$R^5$ is $C_1$-$C_6$ alkyl or benzyl;
$R^{17}$ is a hydroxy protecting group;
$R^7$ is hydrogen, $C_1$-$C_6$ alkyl or an amino acid side chain;
$R^8$ is hydrogen or $C_{1-6}$ alkyl; and L is selected from optionally substituted $C_1$-$C_{20}$ alkylene, $C_3$-$C_8$ cycloalkylene, and optionally substituted $C_1$-$C_{20}$ alkylene wherein one or more of the —$CH_2$— group is independently replaced with $C_3$-$C_8$ cycloalkylene, —O—, —S—, —$NR^{10}$—, —C(=O)$NR^{10}$—, —$NR^{10}$C(=O)—, —$SO_2NR^{10}$—, or —$NR^{10}SO_2$—;

substituted $C_1$-$C_{20}$ alkylene is $C_1$-$C_{20}$ alkylene substituted with 1 to 4 —$SO_3H$, —P(O)(OH)$_2$ or $R^{23}$, wherein each $R^{23}$ is independently $C_{1-6}$ alkyl optionally substituted with 1 or 2 substituents independently selected from the group consisting of SH, S—$C_{1-4}$ alkyl, —$CONR^{11}R^{11}$, and —$NR^{11}Pr$;

FG is independently selected from the group consisting of —$NR^{11}Pr$, —$NR^{11}COCH_2Br$, —$COOR^{12}$, —$CONR^{11}R^{11}$, —$NR^{11}COR^{13}$,

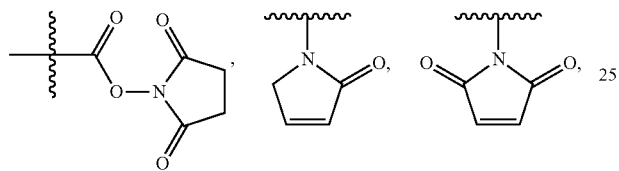

—S—S—$R^{13}$, —Si($R^{13}$)$_3$, alkyl, aryl, cycloalkyl, cycloalkenyl, heteroaryl, and heterocyclic;

each $R^{10}$ or $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo;

Pr is an amino protecting group;

$R^{12}$ is $C_1$-$C_6$ alkyl, or benzyl; and each $R^{13}$ is independently selected from the group consisting of alkyl, aryl, cycloalkyl, heteroaryl, and heterocyclic.

36. A method of preparing a compound of Formula IIIa, or a salt thereof:

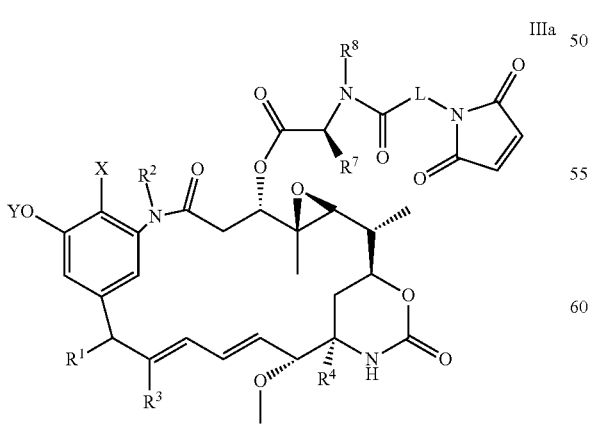

comprising contacting a compound of Formula X:

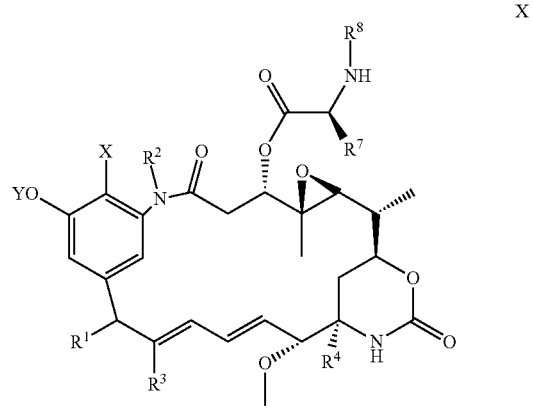

with a carboxylic acid of Formula III-C

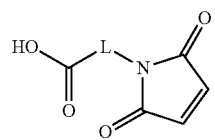

in the presence of a coupling reagent or directly with its active ester to form the compound of Formula III, or a salt thereof;

wherein

X is hydrogen or halo;

Y is selected from the group consisting of hydrogen, $C_1$-$C_6$ alkyl, $C_3$-$C_6$ cycloalkyl, and —C(=O)$R^5$;

$R^1$ is selected from the group consisting of hydrogen, —OH, and —$OR^{17}$;

$R^2$ is hydrogen or $C_1$-$C_6$ alkyl;

$R^3$ is methyl, —$CH_2OH$, or —$CH_2OR^{17}$;

$R^4$ is —OH, —$OR^{17}$ or —SH;

$R^5$ is $C_1$-$C_6$ alkyl or benzyl;

$R^{17}$ is a hydroxy protecting group;

$R^7$ is hydrogen, $C_1$-$C_6$ alkyl or an amino acid side chain;

$R^8$ is hydrogen or $C_{1-6}$ alkyl; and

L is selected from optionally substituted $C_1$-$C_{20}$ alkylene, $C_3$-$C_8$ cycloalkylene, and optionally substituted $C_1$-$C_{20}$ alkylene wherein one or more of the —$CH_2$— group is independently replaced with $C_3$-$C_8$ cycloalkylene, —O—, —S—, —C(O)—, —$NR^8$—, —C(=O)$NR^8$—, —$NR^8$C(=O)—, —$SO_2NR^8$—, or —$NR^8SO_2$—; wherein substituted $C_1$-$C_{20}$ alkylene is $C_1$-$C_{20}$ alkylene substituted with 1 to 4 —$SO_3H$, —P(O)(OH)$_2$ or $R^{23}$, wherein each $R^{23}$ is independently $C_{1-6}$ alkyl optionally substituted with 1 or 2 substituents independently selected from the group consisting of SH, S—$C_{1-4}$ alkyl, —$CONR^{11}R^{11}$, and —$NR^{11}Pr$.

37. The method of claim 36, wherein the compound of Formula III is:

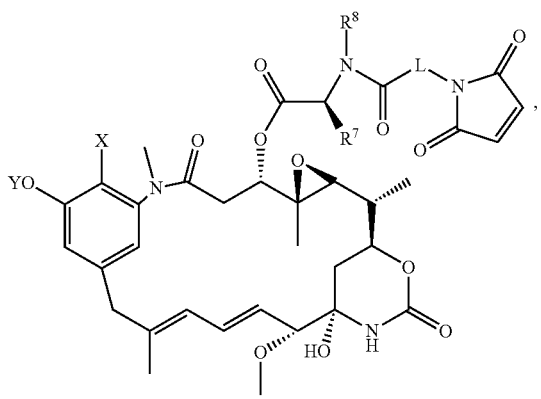

the compound of Formula X is:

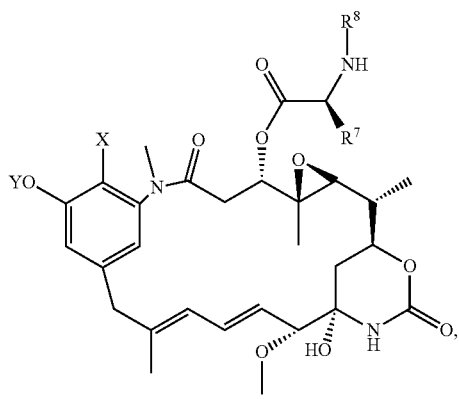

and
the carboxylic acid of Formula III-C is:

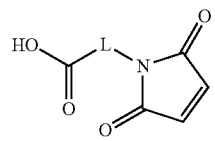

wherein
  X is H or Cl;
  Y is H or methyl;
  $R^7$ is hydrogen, $C_1$-$C_6$ alkyl or an amino acid side chain;
  $R^8$ is hydrogen or $C_{1-6}$ alkyl; and
  L is selected from optionally substituted $C_1$-$C_{20}$ alkylene, $C_3$-$C_8$ cycloalkylene, and optionally substituted $C_1$-$C_{20}$ alkylene wherein one or more of the —$CH_2$— group is independently replaced with $C_3$-$C_8$ cycloalkylene, —O—, —S—, —C(O)—, —$NR^8$—, —C(=O)$NR^8$—, —$NR^8$C(=O)—, —$SO_2NR^8$—, or —$NR^8SO_2$—; wherein substituted $C_1$-$C_{20}$ alkylene is $C_1$-$C_{20}$ alkylene substituted with 1 to 4 —$SO_3H$, —P(O)(OH)$_2$ or $R^{23}$, wherein each $R^{23}$ is independently $C_{1-6}$ alkyl optionally substituted with 1 or 2 substituents independently selected from the group consisting of SH, S—$C_{1-4}$ alkyl, —$CONR^{11}R^{11}$, and —$NR^{11}Pr$.

38. The method of claim 36, wherein the compound of Formula III is:

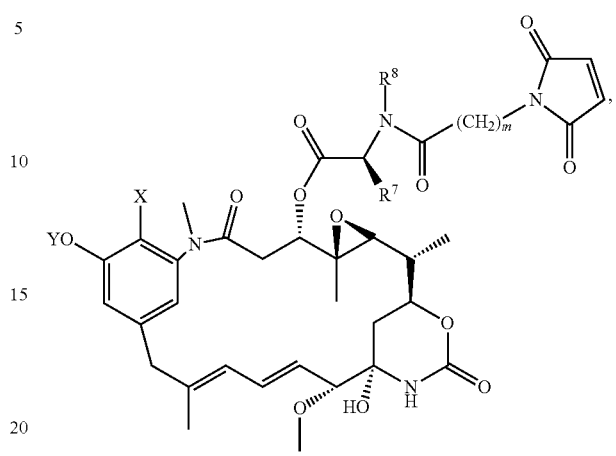

the compound of Formula X is:

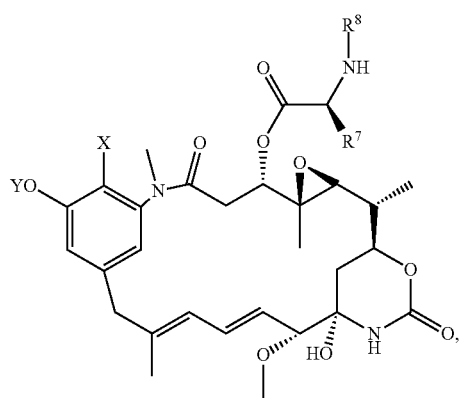

and
the carboxylic acid of Formula III-C is:

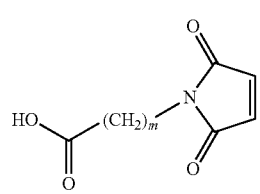

wherein
  X is H or Cl;
  Y is H or methyl;
  $R^7$ is hydrogen, $C_1$-$C_6$ alkyl or an amino acid side chain;
  $R^8$ is hydrogen or $C_{1-6}$ alkyl; and
  m is an integer of 1 to 20.

39. The method of claim 36, wherein the compound of Formula III is:

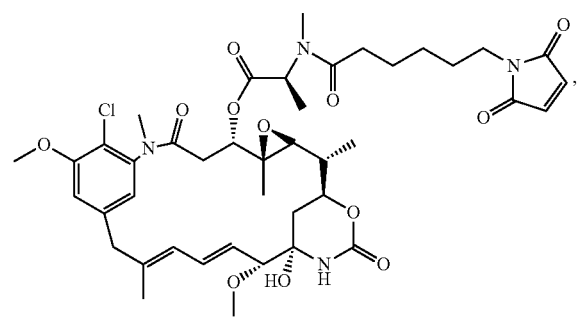

the compound of Formula X is:

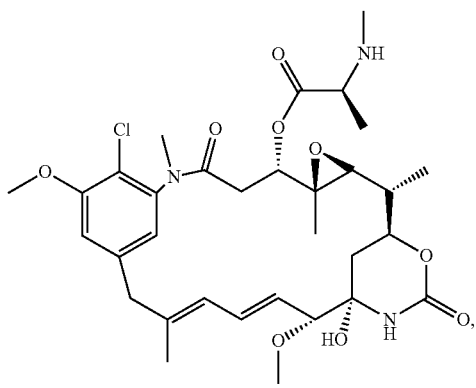

and
the carboxylic acid of Formula III-C is:

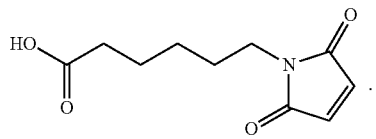 [SMILES: O=C(O)CCCCCN1C(=O)C=CC1=O]

40. A method of preparing a compound of Formula XIV:

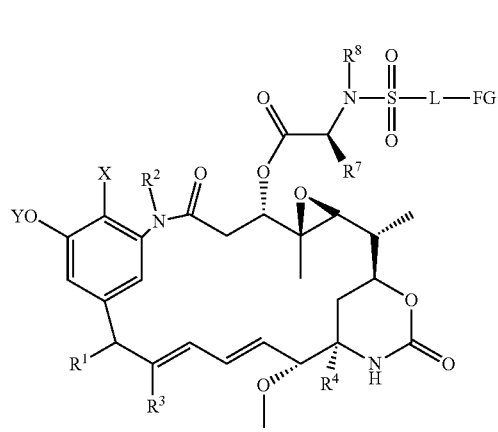

or a salt thereof, comprising contacting a compound of Formula X:

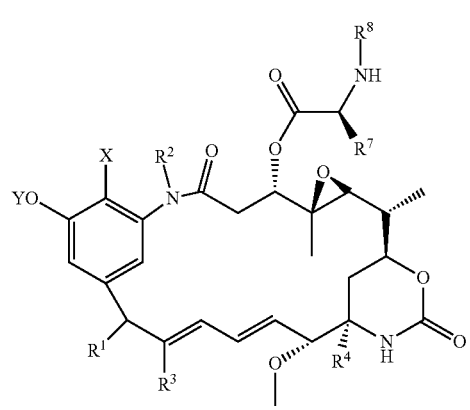

with a sulfonyl chloride of Formula XIV-A

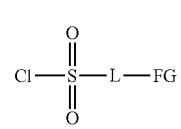

in the presence of a base to form the compound of Formula XIV, or a salt thereof;
wherein
X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, and —OR$^{17}$;
$R^2$ is hydrogen or $C_1$-$C_6$ alkyl;
$R^3$ is methyl, —CH$_2$OH, or —CH$_2$OR$^{17}$;
$R^4$ is —OH, —OR$^{17}$ or —SH;
$R^5$ is $C_1$-$C_6$ alkyl or benzyl;
$R^{17}$ is a hydroxy protecting group;
$R^7$ is hydrogen, $C_1$-$C_6$ alkyl or an amino acid side chain;
$R^8$ is hydrogen or $C_{1-6}$ alkyl; and
L is selected from optionally substituted $C_1$-$C_{20}$ alkylene, $C_3$-$C_8$ cycloalkylene, and optionally substituted $C_1$-$C_{20}$ alkylene wherein one or more of the —CH$_2$— group is independently replaced with $C_3$-$C_8$ cycloalkylene, —O—, —S—, —NR$^{10}$—, —C(=O)NR$^{10}$—, —NR$^{10}$C(=O)—, —SO$_2$NR$^{10}$—, or —NR$^{10}$SO$_2$—;
substituted $C_1$-$C_{20}$ alkylene is $C_1$-$C_{20}$ alkylene substituted with 1 to 4 —SO$_3$H, —P(O)(OH)$_2$ or R$^{23}$, wherein each R$^{23}$ is independently $C_{1-6}$ alkyl optionally substituted with 1 or 2 substituents independently selected from the group consisting of SH, S—$C_{1-4}$ alkyl, —CONR$^{11}$R$^{11}$, and —NR$^{11}$Pr;
FG is independently selected from the group consisting of —NR$^{11}$Pr, —NR$^{11}$COCH$_2$Br, —COOR$^{12}$, —CONR$^{11}$R$^{11}$, —NR$^{11}$COR$^{13}$,

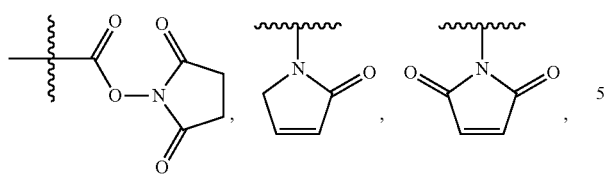

—S—S—R$^{13}$, —Si(R$^{13}$)$_3$, alkyl, aryl, cycloalkyl, cycloalkenyl, heteroaryl, and heterocyclic;

each R$^{10}$ or R$^{11}$ is independently hydrogen, alkyl, aryl, cycloalkyl, cycloalkenyl, heteroaryl, and heterocyclic, or the two R$^{11}$ together with the nitrogen form a heterocyclic, wherein the heterocyclic is optionally substituted with one or two oxo;

Pr is an amino protecting group;

R$^{12}$ is C$_1$-C$_6$ alkyl, or benzyl; and each R$^{13}$ is independently selected from the group consisting of alkyl, aryl, cycloalkyl, heteroaryl, and heterocyclic.

41. A method of preparing a compound of Formula XV, or a salt thereof:

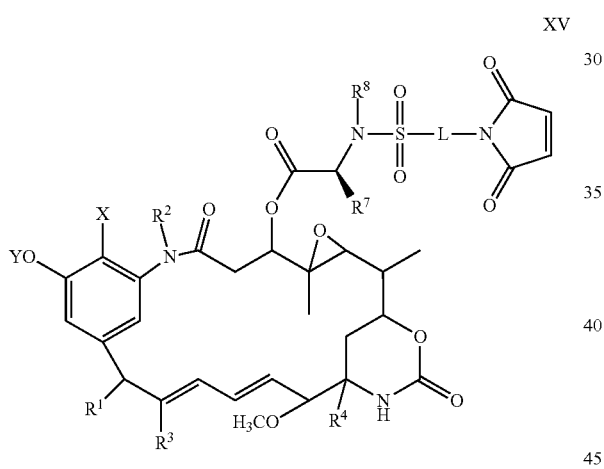

comprising contacting a compound of Formula X:

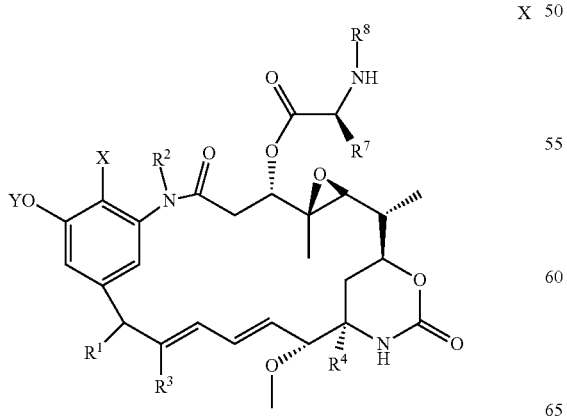

with a sulfonyl chloride of Formula XV-A

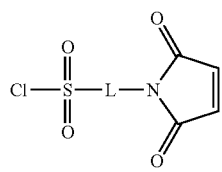

in the presence of a base to form the compound of Formula XV, or a salt thereof;

wherein

X is hydrogen or halo;

Y is selected from the group consisting of hydrogen, C$_1$-C$_6$ alkyl, C$_3$-C$_6$ cycloalkyl, and —C(=O)R$^5$;

R$^1$ is selected from the group consisting of hydrogen, —OH, and —OR$^{17}$;

R$^2$ is hydrogen or C$_1$-C$_6$ alkyl;

R$^3$ is methyl, —CH$_2$OH, or —CH$_2$OR$^{17}$;

R$^4$ is —OH, —OR$^{17}$ or —SH;

R$^5$ is C$_1$-C$_6$ alkyl or benzyl;

R$^{17}$ is a hydroxy protecting group;

R$^7$ is hydrogen, C$_1$-C$_6$ alkyl or an amino acid side chain;

R$^8$ is hydrogen or C$_{1-6}$ alkyl; and

L is selected from optionally substituted C$_1$-C$_{20}$ alkylene, C$_3$-C$_8$ cycloalkylene, and optionally substituted C$_1$-C$_{20}$ alkylene wherein one or more of the —CH$_2$— group is independently replaced with C$_3$-C$_8$ cycloalkylene, —O—, —S—, —C(O)—, —NR$^8$—, —C(=O)NR$^8$—, —NR$^8$C(=O)—, —SO$_2$NR$^8$—, or —NR$^8$SO$_2$—; wherein substituted C$_1$-C$_{20}$ alkylene is C$_1$-C$_{20}$ alkylene substituted with 1 to 4 —SO$_3$H, —P(O)(OH)$_2$ or R$^{23}$, wherein each R$^{23}$ is independently C$_{1-6}$ alkyl optionally substituted with 1 or 2 substituents independently selected from the group consisting of SH, S—C$_{1-4}$ alkyl, —CONR$^{11}$R$^{11}$, and —NR$^{11}$Pr.

42. The method of claim 41, wherein the compound of Formula XV is:

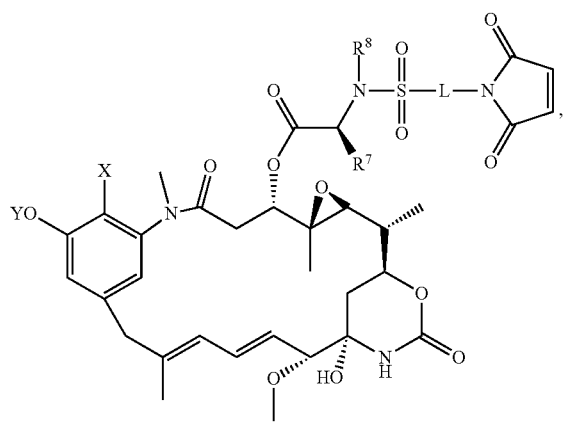

the compound of Formula X is:

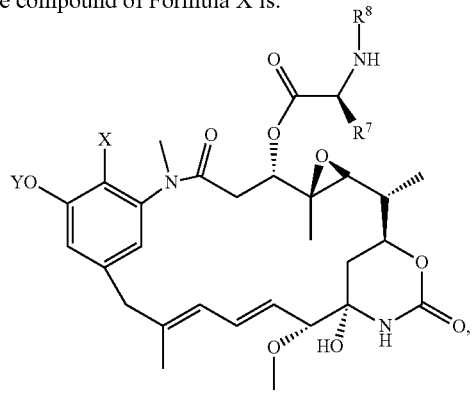

and
the sulfonyl chloride of Formula XV-A is:

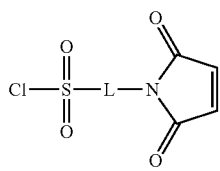

wherein
  X is H or Cl;
  Y is H or methyl;
  $R^7$ is hydrogen, $C_1$-$C_6$ alkyl or an amino acid side chain;
  $R^8$ is hydrogen or $C_{1-6}$ alkyl; and
  L is selected from optionally substituted $C_1$-$C_{20}$ alkylene, $C_3$-$C_8$ cycloalkylene, and optionally substituted $C_1$-$C_{20}$ alkylene wherein one or more of the —$CH_2$— group is independently replaced with $C_3$-$C_8$ cycloalkylene, —O—, —S—, —C(O)—, —$NR^8$—, —C(=O)$NR^8$—, —$NR^8$C(=O)—, —$SO_2NR^8$—, or —$NR^8SO_2$—; wherein substituted $C_1$-$C_{20}$ alkylene is $C_1$-$C_{20}$ alkylene substituted with 1 to 4 —$SO_3H$, —$P(O)(OH)_2$ or $R^{23}$, wherein each $R^{23}$ is independently $C_{1-6}$ alkyl optionally substituted with 1 or 2 substituents independently selected from the group consisting of SH, S—$C_{1-4}$ alkyl, —$CONR^{11}R^{11}$, and —$NR^{11}Pr$.

43. The method of claim 41, wherein the compound of Formula XV is:

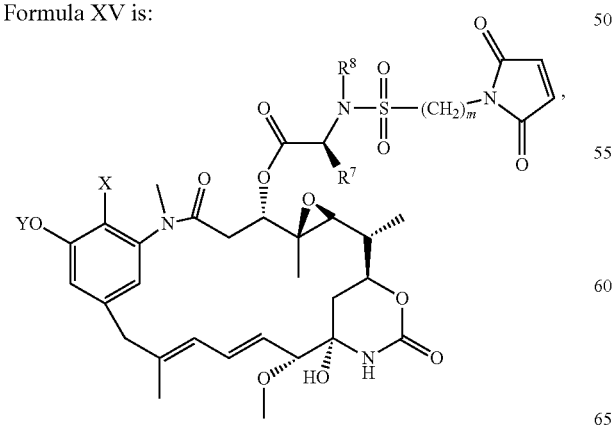

the compound of Formula X is:

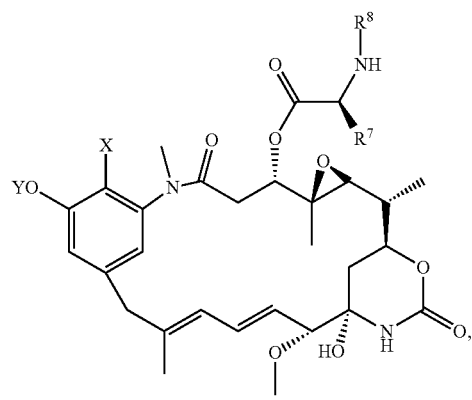

and
the sulfonyl chloride of Formula XV-A is:

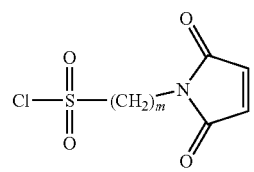

wherein
  X is H or Cl;
  Y is H or methyl;
  $R^7$ is hydrogen, $C_1$-$C_6$ alkyl or an amino acid side chain;
  $R^8$ is hydrogen or $C_{1-6}$ alkyl; and
  m is an integer of 1 to 20.

44. The method of claim 41, wherein the compound of Formula XV is:

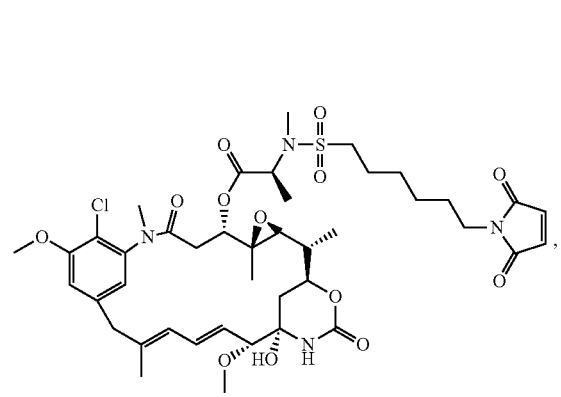

the compound of Formula X is:
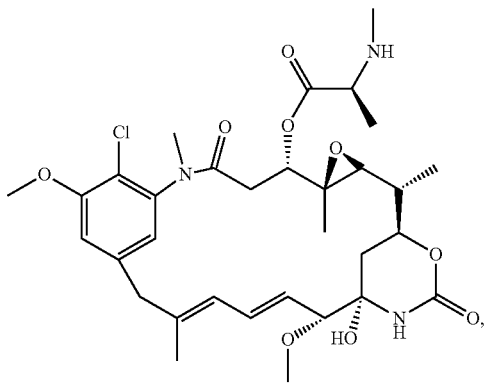
and
the sulfonyl chloride of Formula XV-A is:
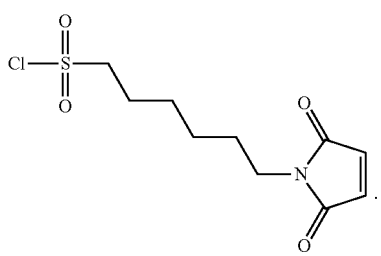 [SMILES: O=C1C=CC(=O)N1CCCCCCS(=O)(=O)Cl]
* * * * *